US009493569B2

(12) United States Patent
Igawa et al.

(10) Patent No.: US 9,493,569 B2
(45) Date of Patent: Nov. 15, 2016

(54) STRUCTURAL ISOMERS OF SC(FV)2

(75) Inventors: Tomoyuki Igawa, Shizuoka (JP);
Hiroyuki Tsunoda, Shizuoka (JP);
Akiko Koga, Tokyo (JP); Yasufumi Kikuchi, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 118 days.

(21) Appl. No.: 11/910,117

(22) PCT Filed: Mar. 31, 2006

(86) PCT No.: PCT/JP2006/306800
§ 371 (c)(1),
(2), (4) Date: Sep. 28, 2007

(87) PCT Pub. No.: WO2006/106903
PCT Pub. Date: Oct. 12, 2006

(65) Prior Publication Data
US 2009/0297501 A1   Dec. 3, 2009

(30) Foreign Application Priority Data

Mar. 31, 2005 (JP) ................. 2005-101711
Dec. 28, 2005 (JP) ................. 2005-378467

(51) Int. Cl.
C07K 16/00     (2006.01)
C12P 21/08     (2006.01)
A61K 39/00     (2006.01)
A61K 51/10     (2006.01)
C07K 16/28     (2006.01)

(52) U.S. Cl.
CPC ..... *C07K 16/2866* (2013.01); *C07K 2317/622* (2013.01); *C07K 2317/626* (2013.01); *C07K 2317/75* (2013.01)

(58) Field of Classification Search
None
See application file for complete search history.

(56) References Cited

U.S. PATENT DOCUMENTS

| 4,946,778 A | 8/1990 | Ladner et al. |
| 5,073,627 A | 12/1991 | Curtis et al. |
| 5,077,216 A | 12/1991 | Morganelli et al. |
| 5,223,241 A | 6/1993 | Isobe et al. |
| 5,516,672 A | 5/1996 | Yamasaki et al. |
| 5,618,920 A | 4/1997 | Robinson et al. |
| 5,747,654 A | 5/1998 | Pastan et al. |
| 5,780,021 A | 7/1998 | Sobel |
| 5,789,554 A | 8/1998 | Leung et al. |
| 5,837,242 A | 11/1998 | Holliger et al. |
| 5,837,821 A | 11/1998 | Wu |
| 5,840,344 A | 11/1998 | Fukushima |
| 5,877,291 A | 3/1999 | Mezes et al. |
| 5,885,574 A | 3/1999 | Elliott |
| 5,892,020 A * | 4/1999 | Mezes et al. ............ 536/23.53 |
| 5,908,925 A | 6/1999 | Cohen et al. |
| 5,977,322 A | 11/1999 | Marks et al. |
| 5,998,593 A | 12/1999 | Huff et al. |
| 6,013,067 A | 1/2000 | Fibbe et al. |
| 6,068,840 A | 5/2000 | Matsushima et al. |
| 6,126,980 A | 10/2000 | Smith et al. |
| 6,132,992 A | 10/2000 | Ledbetter et al. |
| 6,171,586 B1 | 1/2001 | Lam et al. |
| 6,183,744 B1 | 2/2001 | Goldenberg |
| 6,319,499 B1 | 11/2001 | Elliott |
| 6,323,000 B2 | 11/2001 | Briggs et al. |
| 6,342,220 B1 | 1/2002 | Adams et al. |
| 6,361,769 B1 | 3/2002 | Tovey |
| 6,368,596 B1 | 4/2002 | Ghetie et al. |
| 6,579,692 B1 | 6/2003 | Fukushima |
| 6,683,157 B2 | 1/2004 | Briggs et al. |
| 6,699,686 B1 | 3/2004 | Brocard et al. |
| 6,719,972 B1 | 4/2004 | Gribben et al. |
| 6,759,043 B2 | 7/2004 | Fukushima |
| 7,115,373 B2 | 10/2006 | Hashida et al. |
| 7,262,278 B2 | 8/2007 | Tawara et al. |
| 7,456,260 B2 | 11/2008 | Rybak et al. |
| 7,550,140 B2 | 6/2009 | Bakker et al. |
| 7,585,504 B2 | 9/2009 | Wu et al. |
| 7,691,588 B2 | 4/2010 | Tsuchiya et al. |
| 7,749,501 B2 | 7/2010 | Gelfand |
| 8,008,073 B2 | 8/2011 | Tsunoda et al. |
| 8,158,385 B2 | 4/2012 | Ozaki et al. |

(Continued)

FOREIGN PATENT DOCUMENTS

| AU | 755822 | 3/1999 |
| AU | 2004/297111 | 6/2005 |

(Continued)

OTHER PUBLICATIONS

Mallender and Voss. Construction, expression, and activity of a bivalent bispecific single-chain antibody. Journal of Biological Chemistry, 1994. vol. 269, pp. 199-206.*
Cochlovius et al (Treatment of human B cell lymphoma xenografts with a CD3 x CD19 diabody and T cells, 2000, J of Immunol, vol. 165, p. 888-895).*
Orita et al (Agonist of the Thrombopoietin Receptor a Novel Therapeutic Approach for Thrombocytopenia by Minibody, 2005, Blood, vol. 105, p. 562-566).*
Mallender and Voss (Construction, expression, and activity of a bivalent bispecific single-chain antibody, 1994, J Biol Chem, vol. 269, p. 199-206).*

(Continued)

*Primary Examiner* — Julie Wu
(74) *Attorney, Agent, or Firm* — Fish & Richardson P.C.

(57) ABSTRACT

Structural isomers in sc(Fv)2 compositions of anti-human Mpl antibody and humanized anti-human Mpl antibody were separated, and the obtained structural isomers were cleaved at their linkers to confirm that the structural isomers are of single chain diabody type and bivalent scFv type. In addition, the agonistic activities of these structural isomers were revealed to be significantly different. Furthermore, the present inventors discovered that the content ratio of the structural isomers in sc(Fv)2 compositions could be regulated by altering temperature, modifying lengths of the linkers of sc(Fv)2, or amino acids in their variable regions.

14 Claims, 34 Drawing Sheets

(56) References Cited

U.S. PATENT DOCUMENTS

| | | |
|---|---|---|
| 8,945,543 B2 | 2/2015 | Igawa et al. |
| 9,241,994 B2 | 1/2016 | Igawa |
| 2001/0006796 A1 | 7/2001 | Briggs et al. |
| 2002/0028178 A1 | 3/2002 | Hanna et al. |
| 2002/0072091 A1 | 6/2002 | Ni et al. |
| 2002/0155537 A1 | 10/2002 | Carter et al. |
| 2002/0193571 A1 | 12/2002 | Carter et al. |
| 2002/0197706 A1 | 12/2002 | Nadkarni et al. |
| 2003/0073161 A1 | 4/2003 | Briggs et al. |
| 2003/0082612 A1 | 5/2003 | Snodgrass et al. |
| 2003/0103979 A1 | 6/2003 | Leung et al. |
| 2003/0147894 A1 | 8/2003 | Fukushima et al. |
| 2003/0148409 A1 | 8/2003 | Rossi et al. |
| 2003/0157100 A1 | 8/2003 | Fukushima et al. |
| 2003/0157577 A1 | 8/2003 | Fukushima et al. |
| 2003/0190316 A1 | 10/2003 | Kakuta et al. |
| 2003/0202975 A1 | 10/2003 | Tedder |
| 2003/0211108 A1 | 11/2003 | Fukushima et al. |
| 2004/0001828 A1 | 1/2004 | Tuscano et al. |
| 2004/0033228 A1 | 2/2004 | Krause et al. |
| 2004/0058393 A1 | 3/2004 | Fukishima et al. |
| 2004/0073013 A1 | 4/2004 | Fukushima et al. |
| 2004/0091475 A1 | 5/2004 | Tsuchiya et al. |
| 2004/0136951 A1 | 7/2004 | Ni et al. |
| 2004/0219643 A1 | 11/2004 | Winter et al. |
| 2004/0242847 A1 | 12/2004 | Fukushima et al. |
| 2005/0130224 A1 | 6/2005 | Saito et al. |
| 2005/0214278 A1 | 9/2005 | Kakuta et al. |
| 2005/0220787 A1 | 10/2005 | Lobo |
| 2005/0260204 A1 | 11/2005 | Allan |
| 2005/0267222 A1 | 12/2005 | Iwata et al. |
| 2006/0058511 A1 | 3/2006 | Tanikawa et al. |
| 2006/0159673 A1 | 7/2006 | Kojima |
| 2006/0189794 A1 | 8/2006 | Tsuchiya et al. |
| 2006/0222643 A1 | 10/2006 | Tsunoda et al. |
| 2006/0269989 A1 | 11/2006 | Miyazaki et al. |
| 2006/0275301 A1 | 12/2006 | Ozaki et al. |
| 2007/0003556 A1 | 1/2007 | Tsuchiya et al. |
| 2007/0087381 A1 | 4/2007 | Kojima |
| 2007/0280951 A1 | 12/2007 | Kimura et al. |
| 2007/0281327 A1 | 12/2007 | Nakano et al. |
| 2008/0009038 A1* | 1/2008 | Ohtomo et al. ............ 435/69.6 |
| 2008/0107654 A1 | 5/2008 | Kikuchi et al. |
| 2008/0206229 A1 | 8/2008 | Ono et al. |
| 2008/0248037 A1 | 10/2008 | Li et al. |
| 2008/0274110 A1 | 11/2008 | Ozaki et al. |
| 2008/0286280 A1 | 11/2008 | Kallmeyer et al. |
| 2009/0022687 A1 | 1/2009 | Matsumoto et al. |
| 2009/0028854 A1 | 1/2009 | Igawa et al. |
| 2009/0062184 A1 | 3/2009 | Maeda et al. |
| 2009/0117097 A1 | 5/2009 | Igawa et al. |
| 2009/0162352 A1 | 6/2009 | Adler et al. |
| 2009/0214535 A1* | 8/2009 | Igawa ....................... 424/135.1 |
| 2009/0311718 A1 | 12/2009 | Fukushima et al. |
| 2009/0324589 A1 | 12/2009 | Igawa et al. |
| 2010/0015133 A1 | 1/2010 | Igawa et al. |
| 2010/0092457 A1 | 4/2010 | Aburatani et al. |
| 2010/0150927 A1 | 6/2010 | Kimura et al. |
| 2010/0209439 A1 | 8/2010 | Yoshida et al. |
| 2011/0059488 A1 | 3/2011 | Tsunoda et al. |
| 2012/0244142 A1 | 9/2012 | Kimura et al. |
| 2016/0168259 A1 | 6/2016 | Igawa |

FOREIGN PATENT DOCUMENTS

| | | |
|---|---|---|
| AU | 2002210917 B2 | 5/2006 |
| CA | 2272245 | 5/1998 |
| CA | 2 331 641 | 11/1999 |
| CN | 1244805 | 2/2000 |
| CN | 1723036 | 1/2006 |
| DE | 198 19 846 | 11/1999 |
| EP | 437 622 | 7/1991 |
| EP | 0562125 | 9/1993 |
| EP | 0 721 015 | 7/1996 |
| EP | 0 774 511 | 5/1997 |
| EP | 811 691 | 12/1997 |
| EP | 1 035 132 | 9/2000 |
| EP | 1 310 252 | 5/2003 |
| EP | 1 327 680 | 7/2003 |
| EP | 1 327 681 | 7/2003 |
| EP | 1 369 431 | 12/2003 |
| EP | 1 396 500 | 3/2004 |
| EP | 1 475 100 | 11/2004 |
| EP | 1 475 101 | 11/2004 |
| EP | 1 500 665 | 1/2005 |
| EP | 1 561 759 | 8/2005 |
| EP | 1 712 565 | 10/2006 |
| EP | 1 757 686 | 2/2007 |
| EP | 1870458 A1 | 12/2007 |
| EP | 1900814 A1 | 3/2008 |
| EP | 1 925 319 | 5/2008 |
| EP | 1 262 548 | 8/2008 |
| EP | 2 048 230 | 4/2009 |
| JP | 3-41033 | 2/1991 |
| JP | 5-097703 | 4/1993 |
| JP | 7-503622 | 4/1995 |
| JP | 7236475 | 9/1995 |
| JP | 8-500979 | 2/1996 |
| JP | 10-505231 | 5/1998 |
| JP | 10-510842 | 10/1998 |
| JP | 11-500916 | 1/1999 |
| JP | 11-092500 | 4/1999 |
| JP | 2000-95800 | 4/2000 |
| JP | 2001-506135 | 5/2001 |
| JP | 2001-513999 | 9/2001 |
| JP | 2001-518930 | 10/2001 |
| JP | 2001-523971 | 11/2001 |
| JP | 2002-543822 | 12/2002 |
| JP | 2002-544173 | 12/2002 |
| JP | 2003-505344 | 2/2003 |
| JP | 2003-515323 | 5/2003 |
| JP | 2003-531588 | 10/2003 |
| JP | 2004-086682 | 3/2004 |
| JP | 2004-292455 | 10/2004 |
| JP | 4767016 | 9/2011 |
| KR | 10-2004-0085185 | 10/2004 |
| MX | 9905856 A | 7/2000 |
| WO | 9100739 | 1/1991 |
| WO | WO 91/16928 | 11/1991 |
| WO | WO 92/19759 | 11/1992 |
| WO | WO 93/05799 | 4/1993 |
| WO | WO 93/06862 | 4/1993 |
| WO | WO 94/05690 | 3/1994 |
| WO | WO 94/13806 | 6/1994 |
| WO | WO 96/04925 | 2/1996 |
| WO | WO 96/24370 | 8/1996 |
| WO | WO 96/26648 | 9/1996 |
| WO | WO 96/27011 | 9/1996 |
| WO | WO 96/34892 | 11/1996 |
| WO | WO 96/36360 | 11/1996 |
| WO | WO 96/40218 | 12/1996 |
| WO | WO 97/01633 | 1/1997 |
| WO | WO 97/10354 | 3/1997 |
| WO | WO 97/31108 | 8/1997 |
| WO | WO 97/32601 | 9/1997 |
| WO | WO 97/34632 | 9/1997 |
| WO | WO 98/22136 | 5/1998 |
| WO | WO 98/28331 | 7/1998 |
| WO | WO 98/44001 | 8/1998 |
| WO | WO 98/41641 | 9/1998 |
| WO | WO 98/42378 | 10/1998 |
| WO | WO 98/50431 | 11/1998 |
| WO | WO 99/02567 | 1/1999 |
| WO | WO 99/03495 | 1/1999 |
| WO | WO 99/10494 | 3/1999 |
| WO | WO 99/12973 | 3/1999 |
| WO | WO 99/17364 | 4/1999 |
| WO | WO 00/23593 | 4/2000 |
| WO | WO 00/44788 | 8/2000 |
| WO | WO 00/53634 | 9/2000 |
| WO | WO 00/67795 | 11/2000 |
| WO | WO 00/69462 | 11/2000 |
| WO | WO 00/75191 | 12/2000 |
| WO | WO 01/36486 | 5/2001 |

(56) References Cited

FOREIGN PATENT DOCUMENTS

| WO | WO 01/44282 | 6/2001 |
|---|---|---|
| WO | WO 01/64713 | 9/2001 |
| WO | WO 01/66737 | 9/2001 |
| WO | WO 01/70775 | 9/2001 |
| WO | WO 01/74388 | 10/2001 |
| WO | WO 01/77342 | 10/2001 |
| WO | WO 01/79494 | 10/2001 |
| WO | WO 01/87337 | 11/2001 |
| WO | WO 01/97858 | 12/2001 |
| WO | WO 02/04021 | 1/2002 |
| WO | WO 02/22212 | 3/2002 |
| WO | WO 02/33072 | 4/2002 |
| WO | WO 02/33073 | 4/2002 |
| WO | WO 02/078612 | 10/2002 |
| WO | WO 02/094880 | 11/2002 |
| WO | WO 02/096457 | 12/2002 |
| WO | WO 02/097033 | 12/2002 |
| WO | WO 03/002607 | 1/2003 |
| WO | WO 03/033538 | 4/2003 |
| WO | WO 03/033654 | 4/2003 |
| WO | WO 03/057168 | 7/2003 |
| WO | WO 03/068260 | 8/2003 |
| WO | WO 03/086324 | 10/2003 |
| WO | WO 03/087163 | 10/2003 |
| WO | WO 03/097105 | 11/2003 |
| WO | WO 03/103723 | 12/2003 |
| WO | WO 03/104425 | 12/2003 |
| WO | WO 03/107218 | 12/2003 |
| WO | WO 2004/003019 | 1/2004 |
| WO | WO 2004/019966 | 3/2004 |
| WO | WO 2004/026332 | 4/2004 |
| WO | WO 2004/033499 | 4/2004 |
| WO | WO 2004/037293 | 5/2004 |
| WO | WO 2004/081048 | 9/2004 |
| WO | WO 2004/087763 | 10/2004 |
| WO | WO 2004/111233 | 12/2004 |
| WO | WO 2005/044857 | 5/2005 |
| WO | WO 2005/056602 | 6/2005 |
| WO | WO 2005/056603 | 6/2005 |
| WO | WO 2005/056604 | 6/2005 |
| WO | WO 2005/056605 | 6/2005 |
| WO | WO 2005/056798 | 6/2005 |
| WO | WO 2005/100560 | 10/2005 |
| WO | WO 2005/107784 | 11/2005 |
| WO | WO 2006/101173 | 9/2006 |
| WO | WO 2006/123724 | 11/2006 |
| WO | WO 2006/132341 | 12/2006 |
| WO | WO 2006/132352 | 12/2006 |
| WO | WO 2006/132363 | 12/2006 |
| WO | WO 2008/007755 | 1/2008 |
| WO | WO 2008/071394 | 6/2008 |
| WO | WO 2011/037160 | 3/2011 |

OTHER PUBLICATIONS

Arnt et al (Factors Influencing the Dimer to Monomer Transition of an Antibody Single-Chain Fv Fragment, 1998, Biochem, vol. 37, p. 12918-12926).*
Albrecht et al (Bioconjugate Chem, 2004, 15, 15-26).*
Orita et al (Blood, 2005, 105:562-566).*
Cochlovius et al (J of Immunol, 2000, 165:888-895).*
Volkel et al (Protein Engineering, 2001, 14:815-823).*
Columbia Encyclopedia, 2013, "structural isomers".*
USPTO Notice of Allowance in U.S. Appl. No. 10/551,504, mailed May, 26, 2010, 7 pages.
USPTO Final Office Action in U.S. Appl. No. 10/560,098, mailed Jun. 3, 2010, 16 pages.
USPTO Final Office Action in U.S. Appl. No. 11/913,229, mailed Jun. 10, 2010, 10 pages.
USPTO Restriction Requirement in U.S. Appl. No. 11/916,979, mailed Jul. 1, 2010, 7 pages.
Fish & Richardson P.C., Amendment in Reply to Action dated Mar. 24, 2010 in U.S. Appl. No. 10/582,304, filed Jul. 26, 2010, 14 pages.

Chowdhury et al., "Engineering scFvs for improved stability," Methods Mol. Biol., 207:237-54 (2003).
Jung et al., "The importance of framework residues H6, H7 and H10 in antibody heavy chains: experimental evidence for a new structural subclassification of antibody V(H) domains," J. Mol. Biol., 309(3):701-16 (2001).
European Search Report for App. Ser. No. EP 06 75 7198, dated Jun. 11, 2010, 2 pages.
Arndt et al., "Factors influencing the dimer to monomer transition of an antibody single-chain Fv fragment," Biochemistry, 37(37):12918-26 (1998).
Chatellier et al., "Functional mapping of conserved residues located at the VL and VH domain interface of a Fab," J. Mol. Biol., 264(1):1-6 (1996).
Davies et al., "Antibody VH domains as small recognition units," Biotechnology (N.Y.), 13(5):475-9 (1995).
Khalifa et al., "Effects on interaction kinetics of mutations at the VH-VL interface of Fabs depend on the structural context," J. Mol. Recognit., 13(3):127-39 (2000).
Vargas-Madrazo et al., "An improved model of association for VH-VL immunoglobulin domains: asymmetries between VH and VL in the packing of some interface residues," J. Mol. Recognit., 16(3):113-20 (2003).
Wu et al., "Multimerization of a chimeric anti-CD20 single-chain Fv-Fc fusion protein is mediated through variable domain exchange," Protein Eng., 14(12):1025-33 (2001).
USPTO Restriction Requirement in U.S. Appl. No. 11/916,351, mailed Sep. 3, 2010, 8 pages.
European Search Report for App. Ser. No. EP 06 73 0751, dated Jul. 16, 2010, 6 pages.
Fish & Richardson P.C., Response to Restriction Requirement dated Mar. 31, 2010 and Preliminary Amendment in U.S. Appl. No. 11/916,981, filed Sep. 29, 2010, 6 pages.
USPTO Non-Final Office Action in U.S. Appl. No. 10/582,304, mailed Oct. 14, 2010, 7 pages.
Hozumi and Tonegawa, "Evidence for somatic rearrangement of immunoglobulin genes coding for variable and constant regions," Proc. Natl. Acad. Sci. USA, 73(10):3628-3632 (1976).
Fish & Richardson P.C., Amendment in Reply to Action dated Apr. 15, 2009 in U.S. Appl. No. 10/551,504, filed Aug. 14, 2009, 19 pages.
USPTO Office Action in U.S. Appl. No. 10/560,098, mailed Aug. 13, 2009, 21 pages.
USPTO Non-Final Office Action in U.S. Appl. No. 10/582,304, mailed Sep. 15, 2009, 22 pages.
U.S. Appl. No. 11/916,979, filed Aug. 2008, Igawa.
Andris-Widhopf et al., "Methods for the generation of chicken monoclonal antibody fragments by phage display," Journal of Immunological Methods, 242:159-181 (2000).
Arndt et al., "Generation of a highly stable, internalizing anti-DC22 single-chain Fv fragment for targeting non-Hodgkin's lymphoma," Int. J. Cancer, 107(5):822-829 (2003).
Bowie et al., "Deciphering the Message in Protein Sequences: Tolerance to Amino Acid Substitutions," Science, 247:1306-1310 (1990).
Carpenter et al., "Rational design of stable lyophilized protein formulations: some practical advice," Pharmaceutical Research, 14(8):969-975 (1997).
Carpenter et al., "Rational design of stable lyophilized protein formulations: theory and practice," Pharma Biotechnol., 13:109-133 (2001).
Carter, "Bispecific human IgG by design," J. Immunol. Methods, 248:7-15 (2001).
Casset et al., "A peptide mimetic of an anti-CD4 monoclonal antibody by rational design," Biochemical and Biophysical Research Communications, 307:198-205 (2003).
Cekaite et al., "Protein Arrays: A versatile toolbox for target identification and monitoring of patient immune responses," Methods Mol. Biol., 360:335-348 (2007).
Chen et al., "Selection and analysis of an optimized anti-VEGF antibody: crystal structure of an affinity-matured Fab in complex with antigen," Journal of Molecular Biology, 293:865-881 (1999).

(56) References Cited

OTHER PUBLICATIONS

Clackson et al., "Making antibody fragments using phage display libraries," *Nature*, 352:624-628 (1991).
Cleland et al., "A specific molar ratio of stabilizer to protein is required for storage stability of a lyophilized monoclonal antibody," *Journal of Pharmaceutical Sciences*, 90(3):310-321 (2001).
Cochlovius et al., "Treatment of human B cell lymphoma xenografts with a CD3 x CD19 diabody and T cells," *The Journal of Immunology*, 165:888-895 (2000).
Daniel et al., "Pathway of apoptosis induced in Jurkat T Lymphoblasts by anti-HLA Class I antibodies," *Human Immunology*, 65(3):189-199 (2004).
De Jonge et al., "Production and Characterization of Bispecific Single-Chain Antibody Fragments," *Mol. Immunol.*, 32:1405-1412 (1995).
Eijsink et al., "Rational engineering of enzyme stability," *Journal of Biotechnology*, 113:105-120 (2004).
Ewert et al., "Biophysical properties of human antibody variable domains," *J. Mol. Biol.*, 325:531-553 (2003).
Ewert et al., "Stability improvement of antibodies for extracellular and intracellular applications: CDR grafting to stable frameworks and structure-based framework engineering," *Methods*, 34:184-199 ( 2004).
Ewert et al., "Structure-based improvement of the biophysical properties of immunoglobulin $V_H$ domains with a generalizable approach," *Biochemistry*, 42:1517-1528 (2003).
Frokjaer et al., "Protein drug stability: a formulation challenge," *Nature Rev Drug Discov*. 4:298-306 (2005).
Garcia-Gonzalez et al., "Purification of murine IgG3 and IgM monoclonal antibodies by euglobulin precipitation," *Journal of Immunological Methods*, 111:17-23 (1988).
Goldstein et al., "Cytolytic and Cytostatic Properties of an Anti-Human FcγRI (CD64) x Epidermal Growth Factor Bispecific Fusion Protein," *J. Immunol.*, 158:872-879 (1997).
Gombotz et al., "The stabilization of a human IgM monoclonal antibody with poly(vinylpyrrolidone)," *Pharmaceutical Research*, 11(5):624-632 (1994).
Hoogenboom et al., "Multi-subunit proteins on the surface of filamentous phage: methodologies for displaying antibody (Fab) heavy and light chains," *Nucleic Acids Res.*, 19:4133-4137 (1991).
Jäger et al., "Folding and assembly of an antibody Fv fragment, a heterodimer stabilized by antigen," *Journal of Molecular Biology*, 285:2005-2019 (1999).
Kipriyanov and Little, "Generation of Recombinant Antibodies," *Molecular Biotechnology*, 12:173-201 (1999).
Korn et al., "Recombinant bispecific antibodies for the targeting of adenoviruses to CEA-expressing tumour cells: a comparative analysis of bacterially expressed single-chain diabody and tandem scFv," *The Journal of Gene Medicine*, 6:642-651 (2004).
Krebber et al., "Reliable cloning of functional antibody variable domains from hybridomas and spleen cell repertoires employing a reengineered phage display system," *J. Immunol. Methods*, 201:35-55 (1997).
Kumar et al., "Molecular cloning and expression of the fabs of human autoantibodies in *Escherichia coli*," *The Journal of Biological Chemistry*, 275(41):35129-35136 (2000).
Kumar et al., "The second PDZ domain of INAD is a type I domain involved in binding to eye protein kinase C. Mutational analysis and naturally occuring variants," *J. Biol. Chem.*, 276(27):24971-24977 (2001).
Lee et al., "Reversible dimer formation and stability of the anti-tumour single chain Fv antibody MFE-23 by neutron scattering, analytical ultracentrifugation, and NMR and Fr—Ir spectroscopy," *J. Mol. Biol.*, 320:107-127 (2002).
Lin et al., "Structure-function relationships in glucagon: properties of highly purified des-His-1-, monoiodo-, and (des-Asn-28, Thr-29)(homoserine lactone-27)-glucagon," *Biochemistry*, 14:1559-1563 (1975).
Little et al., "Of mice and men: hybridoma and recombinant antibodies," *Immunol. Today*, 21:364-370 (2000).

Liu et al., "Functional interactions between arginine-133 and aspartate-88 in the human reduced folate carrier: evidence for a charge-pair association," *Biochem. J.*, 358:511-516 (2001).
Maity et al., "Equilibrium unfolding of dimeric and engineered monomeric forms of Cro (F58W) repressor and the effect of added salts: evidence for the formation of folded monomer induced by sodium perchlorate," *Archives of Biochemistry and Biophysics*, 434:93-107 (2005).
Martsev et al., "Antiferritin single-chain antibody: a functional protein with incomplete folding?" *FEBS Letters*, 441:458-462 (1998).
McGuinness et al., "Phage diabody repertoires for selection of large number of bispecific antibody fragments," *Nature Biotechnology*, 14(9):1149-1154 (1996).
Merchant et al., "An efficient route to human bispecific IgG," *Nature Biotechnology*, 16:677-681 (1996).
Ngo et al., "Computational Complexity, Protein Structure Prediction, and the Levinthal Paradox," *The Protein Folding Problem and Tertiary Structure Prediction*, Merz, Jr. et al. Editors, Birkhauser Boston, 433-506 (1994).
Nieba et al., "Disrupting the hydrophobic patches at the antibody variable/constant domain interface: improved in vivo folding and physical characterization of an engineered scFv fragment," *Protein Engineering*, 10(4):435-444 (1997).
Nohaile et al., "Altering dimerization specificity by changes in surface electrostatics," *PNAS* 98(6):3109-3114 (2001).
Peipp et al., "Bispecific antibodies targeting cancer cells," *Biochem. Soc. Trans.*, 30:507-511 (2002).
Rajagopal et al., "A form of anti-Tac (Fv) which is both single-chain and disulfide stabilized: comparison with its single-chain and disulfide-stabilized homologs," *Protein Engineering*, 10(12):1453-1459 (1997).
Ridgway et al., "'Knobs-into-holes' engineering of antibody $C_H3$ domains for heavy chain heterodimerization," *Protein Eng.*, 9:617-621 (1996).
Rousch et al., "Somatostatin displayed on filamentous phage as a receptor-specific agonist," *Br. J. Pharmacol.*, 125:5-16 (1998).
Sal-Man et al., "Arginine mutations within a transmembrane domain of Tar, an *Escherichia coli* aspartate receptor, can drive monodimer dissociation and heterodimer association n vivo," *Biochem. J.*, 385(1):29-36 (2005).
Schwartz et al., "A superactive insulin: [B10-aspartic acid]insulin(human)," *Proc. Natl. Acad. Sci. USA*., 84:6408-6411 (1987).
Segal et al., "Bispecific antibodies in cancer therapy," *Current Opinion in Immunology*, 11:558-582 (1999).
Shalaby et al., "Development of Humanized Bispecific Antibodies Reactive with Cytotoxic Lymphocytes and Tumor Cells Overexpressing the HER2 Protooncogene," *J. Exp. Med.*, 175:217-225 (1992).
Sharma et al., "Study of IgM aggregation in serum of patients with macroglobulinemia," *Clin Chem Lab Med*, 38(8):759-764 (2000).
Shimba et al., "Comparative thermodynamic analyses of the Fv, Fab* and Fab fragments of anti-dansyl mouse monoclonal antibody," *FEBS Letters*, 360:247-250 (1995).
Shire et al., "Challenges in the development of high protein concentration formulations," *Journal of Pharmaceutical Sciences*, 93(6):1390-1402 (2004).
Skerra, "Use of the tetracycline promoter for the tightly regulated production of a murine antibody fragment in *Escherichia coli*," *Gene*, 151:131-135 (1994).
Smith-Gill et al., "Contributions of immunoglobulin heavy and light chains to antibody specificity for lysozyme and two haptens," *The Journal of Immunology*, 139:4135-4144 (1987).
Song et al., "Light chain of natural antibody plays a dominant role in protein antigen binding," *Biochemical and Biophysical Research Communications*, 268:390-394, (2000).
Tan et al., "Contributions of a highly conserved $V_H/V_L$ hydrogen bonding interaction to scFv folding stability and refolding efficiency," *Biophysical Journal*, 75:1473-1482 (1998).
Tang et al., "Selection of linkers for a catalytic single-chain antibody using phage display technology", *The Journal of Biological Chemistry*, 271(26):15682-15686 (1996).

(56) References Cited

OTHER PUBLICATIONS

Turner et al., "Importance of the linker in expression of single-chain Fv antibody fragments: optimization of peptide sequence using phage display technology," *Journal of Immunological Methods*, 205:43-54 (1997).
Van Den Burg et al., "Selection of mutations for increased protein stability," *Curr. Opin. Biotechnol.*, 13(4):333-337 (2002).
Vieille et al., "Hyperthermophilic enzymes: sources, uses, and molecular mechanisms for thermostability," *Microbiology and Molecular Biology Reviews*, 65(1):1-43 (2001).
Wang et al., "Instability, stabilization, and formulation of liquid protein pharmaceuticals," *International Journal of Pharmaceutics*, 185:129-188 (1999).
Wang et al., "Lyophilization and developemtn of solid protein pharmaceuticals," *International Journal of Pharmaceutics*, 203:1-60 (2000).
Wang et al., "Protein aggregation and its inhibition in biopharmaceutics," *International Journal of Pharmaceutics*, 289:1-30 (2005).
Wells, "Perspectives in Biochemistry," *Biochemistry*, 29(37):8509-8517 (1990).
Worn et al., "Stability engineering of antibody single-chain Fv fragments," *J. Mol. Biol.*, 305:989- 1010 (2001).
Zhu et al., "Remodeling domain interfaces to enhance heterodimer formation," *Protein Science*, 6:781-788 (1997).
Zhu et al., "An efficient route to the production of an IgG-like bispecific antibody", Protein Eng., 13:361-367 (2000).
USPTO Restriction Requirement in U.S. Appl. No. 10/551,504, mailed Jun. 27, 2008, 6 pages.
Fish & Richardson P.C., Response to Restriction Requirement dated Jun. 27, 2008 in U.S. Appl. No. 10/551,504, filed Sep. 29, 2008, 13 pages.
USPTO Restriction Requirement in U.S. Appl. No. 10/551,504, mailed Dec. 16, 2008, 5 pages.
Fish & Richardson P.C., Response to Restriction Requirement dated Dec. 16, 2008 in U.S. Appl. No. 10/551,504, filed Dec. 23, 2008, 14 pages.
USPTO Non-Final Office Action in U.S. Appl. No. 10/551,504, mailed Apr. 15, 2009, 35 pages.
Japanese Patent Office, International Search Report for App. Ser. No. PCT/JP2004/018506, mailed Mar. 22, 2005, 3 pages.
International Preliminary Report on Patentability for App. Ser. No. PCT/JP2004/018506, 8 pages.
European Search Report for App. Ser. No. EP 04 82 0316, dated Jul. 17, 2008, 3 pages.
USPTO Restriction Requirement in U.S. Appl. No. 10/560,098, mailed Jul. 13, 2007, 9 pages.
USPTO Non-Final Office Action in U.S. Appl. No. 10/560,098, mailed Oct. 23, 2007, 17 pages.
USPTO Final Office Action in U.S. Appl. No. 10/560,098, mailed Sep. 11, 2008, 20 pages.
USPTO Interview Summary for U.S. Appl. No. 10/560,098, mailed Jun. 5, 2009, 8 pages.
Fish & Richardson P.C., Response to Office Action dated Sep. 11, 2008 in U.S. Appl. No. 10/560,098, filed Jun. 10, 2009, 12 pages.
Japanese Patent Office, International Search Report for App. Ser. No. PCT/JP2004/008585, mailed Sep. 7, 2004, 4 pages.
Japanese Patent Office, International Preliminary Report on Patentability for App. Ser. No. PCT/JP2004/008585, 10 pages.
USPTO Restriction Requirement in U.S. Appl. No. 10/582,304, mailed Nov. 20, 2008, 7 pages.
Fish & Richardson P.C., Response to Restriction Requirement dated Nov. 20, 2008 in U.S. Appl. No. 10/582,304, filed Dec. 16, 2008, 3 pages.
USPTO Non-Final Office Action in U.S. Appl. No. 10/582,304, mailed Apr. 1, 2009, 38 pages.
Japanese Patent Office, International Search Report for App. Ser. No. PCT/JP2004/018501, mailed Mar. 29, 2005, 2 pages.
International Preliminary Report on Patentability for App. Ser. No. PCT/JP2004/018501, dated Nov. 4, 2005, 7 pages.

European Search Report for App. Ser. No. EP 04 82 0311, dated Jan. 28, 2009, 4 pages.
Japanese Patent Office, International Search Report for App. Ser. No. PCT/US2006/306803, mailed Jul. 11, 2006, 4 pages.
International Preliminary Report on Patentability for App. Ser. No. PCT/US2006/306803, dated Oct. 3, 2007, 6 pages.
Japanese Patent Office, International Search Report for App. Ser. No. PCT/JP2006/309890, mailed Jul. 18, 2006, 2 pages.
International Preliminary Report on Patentability for App. Ser. No. PCT/JP2006/309890, dated Nov. 19, 2007, 5 pages.
Japanese Patent Office, International Search Report for App. Ser. No. PCT/JP2006/311575, mailed Sep. 26, 2006, 3 pages.
International Preliminary Report on Patentability for App. Ser. No. PCT/JP2006/311575, dated Dec. 11, 2007, 5 pages.
Japanese Patent Office, International Search Report for App. Ser. No. PCT/JP2006/311600, mailed Aug. 29, 2006, 2 pages.
International Preliminary Report on Patentability for App. Ser. No. PCT/JP2006/31160, dated Dec. 11, 2007, 8 pages.
Japanese Patent Office, International Search Report for App. Ser. No. PCT/JP2006/311625, mailed Aug. 22, 2006, 2 pages.
International Preliminary Report on Patentability for App. Ser. No. PCT/JP2006/311625, dated Dec. 11, 2007, 4 pages.
Fish & Richardson P.C., Response to Restriction Requirement dated Jul. 13, 2007 in U.S. Appl. No. 10/560,098, filed Aug. 10, 2007, 6 pages.
Moore et al., "Kinetics and thermodynamics of dimer formation and dissociation for a recombinant humanized monoclonal antibody to vascular endothelial growth factor," Biochemistry, 38:13960-13967 (1999).
Fish & Richardson P.C., Amendment in Reply to Office Action dated Aug. 13, 2009 in U.S. Appl. No. 10/560,098, filed Feb. 16, 2010, 14 pages.
USPTO Non-Final Office Action in U.S. Appl. No. 10/582,304, mailed Mar. 24, 2010, 10 pages.
European Search Report for App. Ser. No. EP 06 76 6512, dated Nov. 30, 2009, 6 pages.
USPTO Restriction Requirement in U.S. Appl. No. 11/916,981, mailed Mar. 31, 2010, 5 pages.
Fish & Richardson P.C., Amendment in Reply to Action dated Nov. 3, 2009 in U.S. Appl. No. 11/913,229, filed Apr. 7, 2010, 15 pages.
Abe et al., "Surrogate thrombopoietin," Immunology Letters, 61:73-78 (1998).
Beresford et al., "Binding Characteristics and Tumor Targeting of a Covalently Linked Divalent CC49 Single-Chain Antibody," *Int. J. Cancer*, 81:911-917 (1999).
Creighton, T., "Protein folding," *Biochem. J.*, 270(1):1-16 (1990).
Kontermann, R., "Recombinant bispecific antibodies for cancer therapy," *Acta Pharmacol. Sin.*, 26(1):1-9 (2005).
Palacios et al., "IL-3-dependent mouse clones that express B-220 surface antigen, contain Ig genes in germ line configuration, and generate B lymphocutes in vivo," *Cell*, 41:727-734 (1985).
Souyri, M., "Mpl: from an acute myeloproliferative virus to the isolation of the long sought thrombopoietin," *Seminars in Hematology*, 35(3):222-231 (1998).
Fish & Richardson P.C., Amendment in Reply to Office Action dated Apr. 1, 2009 in U.S. Appl. No. 10/582,304, filed Jun. 30, 2009, 15 pages.
European Search Report for App. Ser. No. EP 06 73 0748, dated Apr. 22, 2009, 7 pages.
USPTO Restriction Requirement in U.S. Appl. No. 11/913,229, mailed Jul. 8, 2009, 6 pages.
De Jonge et al., "In vivo retargeting of T cell effector function by recombinant bispecific single chain Fv (anti-CD3 x anti-idiotype) induces long-term survival in the murine BCL1 lymphoma model", The Journal of Immunology 161:1454-1461, 1998.
Desplanco et al., "Multimerization behaviour of single chain Fv variants for the tumour-binding antibody B72.3", Protein Engineering 7(8):1027-1033, 1994.
Gruber et al., "Efficient tumor cell lysis mediated by a bispecific single chain antibody expressed in *Escherichia coli*", Journal of Immunology 152:5368-5374-1994.

(56) References Cited

OTHER PUBLICATIONS

Kipriyanov et al., "Bispecific tandem diabody for tumor therapy with improved antigen binding and pharmacokinetics", J. Mol. Biol. 293:41-56, 1999.
Kipriyanov et al., "Bispecific CD3 x CD19 diabody for T cell-mediated lysis of malignant human B cells", Int. J. Cancer 77:763-772, 1998.
Kriangkum et al., "Bispecific and bifunctional single chain recombinant antibodies", Biomolecular Engineering 18:31-40, 2001.
Kurucz et al., "Retargeting of CTL by an efficiently refolded bispecific single-chain Fv dimer produced in bacteria", The Journal of Immunology 154:4576-4582, 1995.
Le Gall et al., "Effect of linker sequences between the antibody variable domains on the formation, stability and biological activity of a bispecific tandem diabody", Protein Engineering Design & Selection 17(4):357-366, 2004.
Mack et al., "A small bispecific antibody construct expressed as a functional single-chain molecule with high tumor cell cytotoxicity", Proc. Natl. Acad. Sci. USA 92:7021-7025, 1995.
Mallender et al., "Constructions, expression, and activity of a bivalent bispecific single-chain antibody", The Journal of Biological Chemistry 269(1):199-206, 1994.
Meng et al., "The evaluation of recombinant, chimeric, tetravalent antihuman CD22 antibodies", Clinical Cancer Research 10:1274-1281, 2004.
Volkel et al., "Optimized linker sequences for the expression of monomeric and dimeric bispecific single-chain diabodies", Protein Engineering 14(10):815-823, 2001.
Whitlow et al., "An improved linker for single-chain Fv with reduced aggression and enhanced proteolytic stability", Protein Engineering 6(8):989-995, 1993.
Sekimoto et al., "A Single-Chain Fv Diabody Against Human Leukocyte Antigen-A Molecules Specifically Induces Myeloma Cell Death in the Bone Marrow Environment," Cancer Res., 67(3):1184-1192 (2007).
Japanese Patent Office, International Search Report for App. Ser. No. PCT/JP2006/306800, mailed May 16, 2006, 4 pages.
International Preliminary Report on Patentability for App. Ser. No. PCT/JP2006/306800, dated Oct. 3, 2007, 6 pages.
Fish & Richardson P.C., Response to Restriction Requirement dated Jul. 8, 2009 in U.S. Appl. No. 11/913,229, filed Aug. 4, 2009, 1 page.
European Search Report for App. Ser. No. EP 06 74 6578, dated Jun. 25, 2009, 2 pages.
USPTO Notice of Allowance in U.S. Appl. No. 10/551,504, mailed Jan. 7, 2010, 46 pages.
Fish & Richardson P.C., Amendment in Reply to Office Action dated Sep. 15, 2009 in U.S. Appl. No. 10/582,304, filed Jan. 13, 2010, 13 pages.
Borden et al., "Lymphokines and Cytokines as Cancer Treatment," Cancer, 65:800-814 (1990).
Byers, "What Can Randomized Controlled Trials Tell us About Nutrition and Cancer Prevention?," CA Cancer J. Clin., 49:353-361 (1999).
Granziero et al., "Adoptive immunotherapy prevents prostate cancer in a transgenic animal model," Eur. J. Immunol., 29:1127-1138 (1999).
USPTO Non-Final Office Action in U.S. Appl. No. 11/913,229, mailed Nov. 3, 2009, 40 pages.
U.S. Appl. No. 10/582,176, filed Jun. 9, 2006, Nakano et al.
U.S. Appl. No. 10/582,413, filed Oct. 26, 2006, Ohtomo et al.
U.S. Appl. No. 10/582,304, filed Jun. 9, 2006, Kimura et al.
U.S. Appl. No. 11/547,747, filed Oct. 5, 2006, Ozaki et al.
U.S. Appl. No. 11/910,128, filed Sep. 28, 2007, Igawa et al.
Ballmaier et al., "c-mpl mutations are the cause of congenital amegakaryocytic thrombocytopenia," Blood, 97:139-146 (2001).
Brinkmann et al., "FTY720: targeting G-protein-coupled receptors for sphingosine 1-phosphate in transplantation and autoimmunity," Curr. Opin. Immunol., 14:569-575 (2002).
Bruenke et al., "A recombinant bispecific single-chain Fv antibody against HLA class II and FcγRIII (CD16) triggers effective lysis of lymphoma cells," Br. J. Haematol., 125:167-179 (2004).
Clark, "CD22, a B Cell-Specific Receptor, Mediates Adhesion and Signal Transduction," J. Immunol., 150:4715-4718 (1993).
Co et al., "A Humanized Antibody Specific for the Platelet Integrin gpIIb/IIIa," J. Immunol., 152:2968-2976 (1994).
Daniel et al., "Induction of Apoptosis in Human Lymphocytes by Human Anti-HLA Class I Antibodies," Transplantation, 75:1380-1386 (2003).
De Felice et al., "Differential regulatory role of monomorphic and polymorphic determinants of histocompatibility leukocyte antigen class I antigens in monoclonal antibody OKT3-induced T cell proliferation," J. Immunol., 139:2683-2689 (1987).
DeNardo et al., "Anti-HLA-DR/anti-DOTA Diabody Construction in a Modular Gene Design Platform: Bispecific Antibodies for Pretargeted Radioimmunotherapy," Cancer Biother. Radiopharm., 16:525-535 (2001).
Deng et al., "An Agonist Murine Monoclonal Antibody to the Human c-Mpl Receptor Stimulates Megakaryocytopoiesis," Blood, 92:1981-1988 (1998).
Ebert et al., "Expression of Metallothionein II in Intestinal Metaplasia, Dysplasia, and Gastric Cancer," Cancer Res., 60:1995-2001 (2000).
Elliott et al., "Activation of the Erythropoietin (EPO) Receptor by Bivalent Anti-EPO Receptor Antibodies," J. Biol. Chem., 271:24691-24697 (1996).
Fayen et al., "Negative signaling by anti-HLA class I antibodies is dependent upon two triggering events," Int. Immunol., 10:1347-1358 (1998).
Funaro et al., "Monoclonal antibodies and therapy of human cancers," Biotechnol. Adv., 18:385-401 (2000).
Genestier et al., "Antibodies to HLA Class 1 α1 Domain Trigger Apoptosis of CD40-Activated Human B Lymphocytes," Blood, 90:726-735 (1997).
Genestier et al., "Caspase-dependent Ceramide Production in Fas- and HLA Class I-mediated Peripheral T Cell Apoptosis," J. Biol. Chem., 273:5060-5066 (1998).
Genestier et al., "Fas-Independent Apoptosis of Activated T Cells Induced by Antibodies to the HLA Class I α1 Domain," Blood, 90:3629-3639 (1997).
Genestier et al., "T cell sensitivity to HLA class I-mediated apoptosis is dependent on interleukin-2 and interleukin-4," Eur. J. Immunol., 27:495-499 (1997).
Ghetie et al., "Homodimerization of tumor-reactive monoclonal antibodies markedly increases their ability to induce growth arrest or apoptosis of tumor cells," Proc. Natl. Acad. Sci. USA, 94:7509-7514 (1997).
Goel et al., "$^{99m}$Tc-Labeled Divalent and Tetravalent CC49 Single-Chain Fv's: Novel Imaging Agents for Rapid In Vivo Localization of Human Colon Carcinoma," J. Nucl. Med., 42:1519-1527 (2001).
Goel et al., "Genetically Engineered Tetravalent Single-Chain Fv of the Pancarcinoma Monoclonal Antibody CC49: Improved Biodistribution and Potential for Therapeutic Application," Cancer Res., 60:6964-6971 (2000).
Goto et al., "A Novel Membrane Antigen Selectively Expressed on Terminally Differentiated Human B Cells," Blood, 84:1922-1930 (1994).
Holliger et al., "'Diabodies': Small bivalent and bispecific antibody fragments," Proc. Natl. Acad. Sci. USA, 90:6444-6448 (1993).
Hu et al., "Minibody: A Novel Engineered Anti-Carcinoembryonic Antigen Antibody Fragment (Single-Chain Fv-$C_H3$) Which Exhibits Rapid, High-Level Targeting of Xenografts," Cancer Res., 56:3055-3061 (1996).
Hudson et al., "High avidity scFv multimers; diabodies and triabodies," J. Immunol. Methods, 231:177-189 (1999).
Kikuchi et al., "A bivalent single-chain Fv fragment against CD47 induces apoptosis for leukemic cells," Biochem. Biophys. Res. Commun., 315:912-918 (2004).
Kimura et al., "2D7 diabody bound to the α2 domain of HLA class I efficiently induces caspase-independent cell death against malignant and activated lymphoid cells," Biochem. Biophys. Res. Commun., 325:1201-1209 (2004).

(56) References Cited

OTHER PUBLICATIONS

Kipriyanov et al., "Effect of Domain Order on the Activity of Bacterially Produced Bispecific Single-chain Fv Antibodies," *J. Mol. Biol.*, 330:99-111 (2003).
Kong et al., "A Single Residue, Aspartic Acid 95, in the δ Opioid Receptor Specifies Selective High Affinity Agonist Binding", The Journal of Biological Chemistry, vol. 268(31), pp. 23056-23058 (1993).
Kortt et al., "Dimeric and trimeric antibodies: high avidity scFvs for cancer targeting," *Biomol. Eng.*, 18:95-108 (2001).
Kreitman et al., "Cytotoxic Activity of Disulfide-stabilized Recombinant Immunotoxin RFB4(dsFv)-PE38 (BL22) toward Fresh Malignant Cells from Patients with B-Cell Leukemias," *Clin. Cancer Res.*, 6:1476-1487 (2000).
Kulkarni et al., "Construction of a Single-Chain Antibody Derived From 5H7, A Monoclonal Antibody Specific for a Death Signaling Domain of Human Class I Major Histocompatibility Complex," *Transplant. Proc.*, 30:1081 (1998).
Kulkarni et al., "Programmed Cell Death Signaling Via Cell-Surface Expression of a Single-Chain Antibody Transgene," *Transplantation*, 69:1209-1217 (2000).
Lebrun et al., "Antibodies to the Extracellular Receptor Domain Restore the Hormone-insensitive Kinase and Conformation of the Mutant Insulin Receptor Valine 382," *J. Biol. Chem.*, 268:11272-11277 (1993).
Ledbetter et al., Agonistic Activity of a CD40-Specific Single-Chain Fv Constructed from the Variable Regions of mAb G28-5, Critical Reviews in Immunology, vol. 17, pp. 427-435 (1997).
Li et al., "The Epitope Specificity and Tissue Reactivity of Four Murine Monoclonal Anti-CD22 Antibodies," *Cell. Immunol.*, 118:85-99 (1989).
Matsuoka et al., "A Monoclonal Antibody to the α2 Domain of Murine Major Histocompatibility Complex Class I that Specifically Kills Activated Lymphocytes and Blocks Liver Damage in the Concanavalin A Hepatitis Model," *J. Exp. Med.*, 198:497-503 (2003).
Matsuoka et al., "A Novel Type of Cell Death of Lymphocytes Induced by a Monoclonal Antibody without Participation of Complement," *J. Exp. Med.*, 181:2007-2015 (1995).
Medline Plus Drug Information: Dexamethasone Oral www.nlm.nih.gov/medlineplus/druginfo/meddmaster/a682792.html, downloaded Jul. 19, 2007; last revised Apr. 1, 2003 (see p. 3) (4 pages).
Nishii, "CD22 antibody therapy," *Current Therapy*, 20:47-50 (2001) (English translation included).
Ohtomo et al., "Molecular Cloning and Characterization of a Surface Antigen Preferentially Overexpressed on Multiple Myeloma Cells," *Biochem. Biophys. Res. Commun.*, 258:583-591 (1999).
Oka, "Development of Novel Immunotoxin Using Recombinant Alpha-Sarcin and Its Application Treatment of Hematopoietic Tumor," *Sankyo Seimei Kagaku Kenkyu Shinko Zaidan Kenkyu Hokokushu*, 12:46-56 (1998) (concise English explanation included).
Ono et al., "The humanized anti-HM1.24 antibody effectively kills multiple myeloma cells by human effector cell-mediated cytotoxicity," *Mol. Immunol.*, 36:387-395 (1999).
Orita et al., "A novel therapeutic approach for thrombocytopenia by minibody agonist of the thrombopoietin receptor," *Blood*, 105:562-566 (2005).
Ozaki et al., "A Recombinant HLA Class I-Specific Single Chain Fv Diabody Induces Cell Death in Human Lymphoid Malignancies," *Blood*, 102:933a, Abstract No. 3474 (2003).
Ozaki et al., "Humanized Anti-HM1.24 Antibody Mediates Myeloma Cell Cytotoxicity That Is Enhanced by Cytokine Stimulation of Effector Cells," *Blood*, 93:3922-3930 (1999).
Ozaki et al , "Immunotherapy of Multiple Myeloma With a Monoclonal Antibody Directed Against a Plasma Cell-Specific Antigen, HM1.24," *Blood*, 90:3179-3186 (1997).

Pettersen et al., "The TCR-Binding Region of the HLA Class I $\alpha_2$ Domain Signals Rapid Fas-Independent Cell Death: A Direct Pathway for T Cell-Mediated Killing of Target Cells?" *J. Immunol.*, 160:4343-4352 (1998).
Piétri-Rouxel et al., "The biochemical effect of the naturally occurring Trp64→ Arg mutation on human β33-adrenoceptor activity," *Eur. J. Biochem.*, 247:1174-1179 (1997).
Plückthun et al., "New protein engineering approaches to multivalent and bispecific antibody fragments," *Immunotechnology*, 3:83-105 (1997).
Rossi et al., "Development of New Multivalent-bispecific Agents for Pretargeting Tumor Localization and Therapy," *Clin. Cancer Res.*, 9:3886s-3896s (2003).
Sato et al., "CD22 Is Both a Positive and Negative Regulator of B Lymphocyte Antigen Receptor Signal Transduction: Altered Signaling in CD22-Deficient Mice," *Immunity*, 5:551-562 (1996).
Scheurle et al., "Cancer Gene Discovery Using Digital Differential Display," *Cancer Res.*, 60:4037-4043 (2000).
Smith et al., "Inhibition of T Cell Activation by a Monoclonal Antibody Reactive Against the α3 Domain of Human MHC Class I Molecules," *J. Immunol.*, 153:1054-1067 (1994).
Tahtis et al., "Biodistribution Properties of $^{111}$Indium-labeled C-Functionalized trans-Cyclohexyl Diethylenetriaminepentaacetic Acid Humanized 3S193 Diabody and F(ab')$_2$ Constructs in a Breast Carcinoma Xenograft Model," *Clin. Cancer Res.*, 7:1061-1072 (2001).
Tedder et al., "CD22, a B Lymphocyte-Specific Adhesion Molecule That Regulates Antigen Receptor Signaling," *Annu. Rev. Immunol.*, 15:481-504 (1997).
Thilenius et al., "Agonist antibody and Fas ligand mediate different sensitivity to death in the signaling pathways of Fas and cytoplasmic mutants," *Eur. J. Immunol.*, 27:1108-1114 (1997).
Woodle et al., "Anti-Human Class I MHC Antibodies Induce Apoptosis by a Pathway That Is Distinct from the Fas Antigen-Mediated Pathway," *J. Immunol.*, 158:2156-2164 (1997).
Woodle et al., "Anti-Human Class I α3 Domain-Specific Monoclonal Antibody Induces Programmed Cell Death in Murine Cells Expressing Human Class I MHC Transgenes," *Transplant. Proc.*, 30:1059-1060 (1998).
Woodle et al., "Class I MHC Mediates Programmed Cell Death in Human Lymphoid Cells," *Transplantation*, 64:140-146 (1997).
Wu et al., "Tumor localization of anti-CEA single-chain Fvs: improved targeting by non-covalent dimers," *Immunotechnology*, 2:21-36 (1996).
Xiong et al., "Efficient inhibition of human B-cell lymphoma xenografts with an anti-CD20 x anti-CD3 bispecific diabody," *Cancer Lett.*, 177:29-39 (2002).
Xu et al., "Insight into hepatocellular carcinogenesis at transcriptome level by comparing gene expression profiles of hepatocellular carcinoma with those of corresponding noncancerous liver," *Proc. Natl. Acad. Sci. USA*, 98:15089-15094 (2001).
U.S. Appl. No. 11/373,063, filed Mar. 10, 2006, Ozaki et al.
Co et al., "A Humanized Antibody Specific for the Platelet Integrin gpIIb/IIIa,"*J. Immunol.*, 152:2968-2976 (1994).
Deng et al., "An Agonist Murine Monoclonal Antibody to the Human c-Mpl Receptor Stimulates Megakaryoutopoiesis," *Blood*, 92:1981-1988 (1998).
Ozaki et al., "Immunotherapy of Multiple Myeloma With a Monoclonal Antibody Directed Against a Plasma Cell-Specific Antigen, HM1.24," *Blood*, 90:3179-3186 (1997).
Piétri-Rouxel et al., "The biochemical effect of the naturally occurring Trp64→ Arg mutation on human β3-adrenoceptor activity," *Eur. J. Biochem.*, 247:1174-1179 (1997).
Fish & Richardson P.C., Amendment in Reply to Action dated Mar. 3, 2011 in U.S. App. No. 11/916,351, filed Aug. 2, 2011, 16 pages.
USPTO Notice of Allowability in U.S. Appl. No. 10/530,696, mailed Aug. 15, 2011, 3 pages.
USPTO Non-Final Office Action in U.S. Appl. No. 10/582,304, mailed Aug. 15, 2011, 10 pages.
Arndt et al., "Factors Influencing the Dimer to Monomer Transition of an Antibody Single-Chain Fv Fragment," *Biochemistry*, 37:12918-12926 (1998).

(56) References Cited

OTHER PUBLICATIONS

Avent et al., "Monoclonal antibodies that recognize different membrane proteins that are deficient in Rhnull human erythrocytes. One group of antibodies reacts with a variety of cells and tissues whereas the other group is erythroid-specific," *Biochem. J.*, 251:499-505 (1988).
Bartley et al., "Identification and Cloning of a Megakaryocyte Growth and Development Factor That is a Ligand for the Cytokine Receptor Mpl," *Cell*, 77:1117-1124 (1994).
Bazil et al., "Apoptosis of human hematopoietic progenitor cells induced by crosslinking of surface CD43, the major sialoglycoprotein of leukocytes," *Blood*, 86:502-511 (1995).
Bazzoni et al., "Chimeric tumor necrosis factor receptors with constitutive signaling activity," *Proc. Natl. Acad. Sci. USA*, 92(12):5376-5580 (1995).
Berger et al., "Inhibition of intractable nucleases with ribonucleoside-vanadyl complexes: isolation of messenger ribonucleic acid from resting lymphocytes," *Biochemistry*, 18(23):5143-5149 (1979).
Bodmer et al., "TRAIL Receptor-2 Signals Apoptosis Through FADD and Caspase-8," *Nat. Cell Biol.*, 2:241-243 (2000).
Boger et al., "Cytokine receptor dimerization and activation: prospects for small molecule agonists," *Bioorganic and Medicinal Chemistry*, 9(3):557-562 (2001).
Brooke et al., "Human lymphocytes interact directly with CD47 through a novel member of the signal regulatory protein (SIRP) family," *J. Immunol.*, 173:2562-2570 (2004).
Brown et al., "Integrin-associated protein: a 50-kD plasma membrane antigen physically and functionally associated with integrins," *J. Cell Biology*, 111(6 Pt 1):2785-2794 (1990).
Brown et al., "Integrin-associated protein (CD47) and its ligands," *Trends Cell Biology*, 11(3):130-135 (2001).
Buchsbaum et al., "Antitumor Efficacy of TRA-8 Anti-DR5 Monoclonal Antibody Alone or in Combination with Chemotherapy and/or Radiation Therapy in a Human Breast Cancer Model," *Clin. Cancer Res.*, 9:3731-3741 (2003).
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol.*, 111:2129-2138 (1990).
Burthem et al., "Hairy cell interactions with extracellular matrix: expression of specific integrin receptors and their role in the cell's response to specific adhesive proteins," *Blood*, 84(3):873-882 (1994).
Burrone et al., "Stimulation of HLA-A,B,C by IFN-alpha. The derivation of Molt 4 variants and the differential expression of HLA-A,B,C subsets," *The EMBO Journal*, 4(11):2855-2860 (1985).
Caldas et al., "Humanization of the anti-CD18 antibody 6.7: an unexpected effect of a framework residue in binding to antigen," *Mol. Immunol.*, 39:941-952 (2003).
Cangemi et al., "IFN-alpha mediates the up-regulation of HLA class I on melanoma cells without switching proteasome to immunoproteasome," *International Immunology*, 15(12):1415-1421 (2005).
CAPLUS Accession No. 2005:547624, 2 pages (2008).
Caron et al., "Engineered Humanized Dimeric Forms of IgG Are More Effective Antibodies," *J. Exp. Med.*, 176:1191-1195 (1992).
Chien et al., "Significant structural and functional change of an antigen-binding site by a distant amino acid substitution: Proposal of a structural mechanism," *Proc. Nat. Acad. Sci. USA*, 86:5532-5536 (1989).
Chirgwin et al., "Isolation of biologically active ribonucleic acid from sources enriched in ribonuclease," *Biochemistry*, 18(24):5294-5299 (1979).
Chuntharapai et al. "Isotype-Dependent Inhibition of Tumor Growth In Vivo by Monoclonal Antibodies to Death Receptor 4," *J. Immunol.*, 166:4891-4898 (2001).

Cochlovius et al., "Cure of Burkitt's Lymphoma in Severe Combined Immunodeficiency Mice by T Cells, Tetravalent CD3 x CD19 Tandem Diabody and CD28 Costimulation," *Cancer Res.*, 60:4336-4341 (2000).
Cooper et al., "Transendothelial migration of neutrophils involves integrin-associated protein (CD47)," *Proc. Natl. Acad. Sci. USA*, 92:3978-3982 (1995).
De Leon et al., "High resolution human leukocyte antigen (HLA) class I and class II allele typing in Mexican mestizo women with sporadic breast cancer: case-control study," *BMC Cancer*, 9(48):19 (2009).
De Pascalis et al., "Grafting of 'abbreviated' complementary-determining regions containing specificity-determining residues essential for ligand contact to engineer a less immunogenic humanized monoclonal antibody," *Journal of Immunology*, 169:3076-3084 (2002).
Degli-Esposti et al., "Cloning and Characterization of TRAIL-R3, a Novel Member of the Emerging TRAIL Receptor Family," *J. Exp. Med.*, 186:1165-1170 (1997).
De Sauvage et al., "Stimulation of Megakaryocytopoiesis and Thrombopoiesis by the c-Mpl Ligand," *Nature*, 369:533-538 (1994).
De St. Groth et al., "Production of Monoclonal Antibodies: Strategy and Tactics," *Journal of Immunological Methods*, 35:1-21 (1980).
Dillman, "Monoclonal antibodies for treating cancer," *Ann. Int. Med.*, 11(7):592-603 (1989).
Dorai et al., "Mammalian cell expression of single-chain Fv (sFv) antibody proteins and their C-terminal fusions with interleukin-2 and other effector domains," *Biotechnology*, 12(9):890-897 (1994).
Dufner et al., "Harnessing phage and ribosome display for antibody optimization," *Trends Biotechnol.*, 24(11):523-529 (2006).
Emery et al., "Osteoprotegerin Is a Receptor for the Cytotoxic Ligand TRAIL," *J. Biol. Chem.*, 273:14363-14367 (1998).
Felgenhauer et al. "Nucleotide Sequences of the cDNAs Encoding the V-Regions of H- and L-Chains of a Human Monoclonal Antibody Specific to HIV-1-gp41," *Nucleic Acids Research*, 18(16):4927 (1990).
Fujimoto et al., "50-kD integrin-associated protein does not detectably influence several functions of glycoprotein IIb-IIIa complex in human platelets," *Blood*, 86(6):2174-2182 (1995).
Fukushima et al., "Enhanced hematopoiesis in vivo and in vitro by splenic stromal cells derived from the mouse with recombinant granulocyte colony-stimulating factor," *Blood*, 80(8):1914-1922 (1992).
Fukushima et al., "Apoptosis of Bone Marrow Cells Via Integrin Associated Protein by the Novel Monoclonal Antibody," *Blood*, 94(10):479A (1999).
Galfre et al., "Preparation of monoclonal antibodies: strategies and procedures," *Methods in Enzymology*, 73:3-46 (1981).
Galfre et al., "Rat x rat hybrid myelomas and a monoclonal anti-Fd portion of mouse IgG," *Nature*, 277:131-133 (1979).
GenBank: U27005.1, *Mus musculus*, isolate 7183Liv, Vh7183 Ig heavy chain variable region gene, Vh region, partial cds, 1 page (Apr. 1996).
GenBank: AY081858.1, *Mus musculus*, isolate H3-9 anti-GBM immunoglobulin kappa chain variable region mRNA, partial cds, 1 page (Mar. 2004).
Giusti et al., "Somatic diversification of S107 from an antiphosphocholine to an anti-DNA autoantibody is due to a single base change in its heavy chain variable region," *Proc. Natl. Acad. Sci. USA*, 84:2926-2930 (1987).
Greenspan et al., "Defining epitopes: It's not as easy as it seems," *Nature Biotechnology*, 17:936-937 (1999).
Grell et al., "TR60 and TR80 tumor necrosis factor (TNF)-receptors can independently mediate cytolysis," *Lymphokine and Cytokine Research*, 12(3):143-148 (1993).
Griffith et al., "Functional Analysis of TRAIL Receptors Using Monoclonal Antibodies," *J. Immunol.*, 162:2597-2605 (1999).
Güssow and Seemann, "Humanization of Monoclonal Antibodies," *Methods in Enzymology*, 203:99-121 (1991).
Holliger el at., "Specific Killing of Lymphoma Cells by Cytotoxic T-Cells Mediated by a Bispecific Diabody," *Protein Engineering*, 9(3):299-305 (1996).

(56) References Cited

OTHER PUBLICATIONS

Holm et al., "Functional mapping and single chain construction of the anti-cytokeratin 8 monoclonal antibody TS1," *Molecular Immunology*, 44:1075-1084 (2007).
Hopp et al., "A Short Polypeptide Marker Sequence Useful for Recombinant Protein Identification and Purification," *Biotechnology*, 6:1204-1210 (1988).
Horan et al., "Dimerization of the extracellular domain of granuloycte-colony stimulating factor receptor by ligand binding: a monovalent ligand induces 2:2 complexes," *Biochemistry*, 35:4886-4896 (1996).
Huston et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA*, 85:5879-5883 (1988).
Ichikawa et al., "Tumoricidal activity of a novel anti-human DR5 monoclonal antibody without hepatocyte cytotoxicity," *Nat. Med.*, 7:954-960 (2001).
Itoh et al., "The Polypeptide Encoded by the cDNA for Human Cell Surface Antigen Fas Can Mediate Apoptosis," *Cell*, 66:233-243 (1991).
Jiang et al., "A Novel Peptide Isolated from a Phage Display Peptide Library with Trastuzumab Can Mimic Antigen Epitope of HER-2," *J. Biol. Chem.*, 280(6):4656-4662 (2005).
Jones et al., "Rapid PCR-Cloning of Full-Length Mouse Immunoglobulin Variable Regions," *Biotechnology*, 9:88-89 (1991).
Kearney, et al., "A New Mouse Myeloma Cell Line That Has Lost immunoglobulin Expression But Permits the Construction of Antibody-Secreting Hybrid Cells Lines," *The Journal of Immunology*, 123(4):1548-1550 (1979).
Keen et al., "The use of serum-free medium for the production of functionally active humanized monoclonal antibody from NSO mouse myeloma cells engineered using glutamine synthetase as a selectable marker," *Cytotechnology*, 18(3):207-217 (Abstract) (1994).
Kohler, et al., "Derivation of specific antibody-producing tissue culture and tumor lines by cell fusion," *Eur. J. Immunol.*, 6:511-519 (1976).
Kortt et al., "Recombinant anti-sialidase single-chain variable fragment antibody: Characterization, formation of dimmer and higher-molecular-mass multimers and the solution of the crystal structure of the single-chain variable fragment/sialidase complex," *Eur. J. Biochem.*, 221:151-157 (1994).
Kortt et al., "Single-chain Fv fragments of anti-neuraminidase antibody NC10 containing five- and ten-residue linkers form dimmers and with zero-residue linker a trimer," *Protein Engineering*, 10(4):423-433 (1997).
Kozak, M., "At Least Six Nucleotides Preceding the AUG Initiator Codon Enhance Translation in Mammalian Cells," *J. Mol. Biol.*, 196:947-950 (1987).
Larrick, et al., "Polymerase Chain Reaction Using Mixed Primers: Cloning of Human Monoclonal Antibody Variable Region Genes From Single Hybridoma Cells," *Biotechnology*, 7:934-938 (1989).
Law et al., "Observations on the Effect of a Folic-Acid Antagonist on Transplantable Lymphoid Leukemias in Mice," *Journal of the National Cancer Institute*, 10:179-193 (1949).
Lazar et al., "Transforming growth factor a: mutation of aspartic acid 47 and leucine 48 results in different biological activities," *Molecular and Cellular Biology*, 8:1247-1252 (1988).
Lei et al., "Characterization of the *Erwinia carotovora* pelB Gene and Its Product Pectate Lyase," *Journal of Bacteriology*, 169:4379-4383 (1987).
Lindberg et al., "Molecular Cloning of Integrin-Associated Protein: An Immunoglobulin Family Member with Multiple Membrane-Spanning Domains Implicated in $\alpha_v\beta_3$-Dependent Ligand Binding," *The Journal of Cell Biology*, 123(2):485-496, The Rockefeller University Press (1993).
Lindberg et al., "Rh-Related Antigen CD47 is the Signal-Transducer Integrin-Associated Protein," *J. Biol. Chem.*, 269:1567-1570 (1994).

MacCallum et al., "Antibody-antigen independent interactions: contact analysis and binding site topography," *Journal of Molecular Biology*, 262:732-745 (1996).
Margulies et al., "Somatic Cell Hybridization of Mouse Myeloma Cells," *Cell*, 8:405-415 (1976).
Mariuzza et al., "The Structural Basis of Antigen-Antibody Recognition," *Ann. Rev. Biophys. Biophys. Chem.*, 16:139-159 (1987).
Marsters et al., "A Novel Receptor for Apo2L/TRAIL Contains a Truncated Death Domain," *Curr. Biol.*, 7:1003-1006 (1997).
Mateo et al., "Induction of Apoptosis in B-Cells From Chronic Lymphocytic Leukemia (B-CLLs) by CD47," *FASEB Journal*, 12(5):A1082 (1998).
Mateo et al., "CD47 ligation induces caspase-independent cell death in chronic lymphocytic leukemia," *Nat. Med.*, 5(11):1277-1284 (1999).
Mawby et al., "Isolation and characterization of CD47 glycoprotein: a multispanning membrane protein which is the same as integrin-associated protein (IAP) and the ovarian tumor marker OA3," *Biochem. J.*, 304:525-530 (1994).
McInnes and Schett, "Cytokines in the pathogenesis of rheumatoid arthritis," *Nature Reviews/Immunology*, 7:429-442 (2007).
Methia et al., "Oligodeoxynucleotides Antisense to the Proto-Oncogene c-Mpl Specifically Inhibit In Vitro Megakaryocytopoiesis," *Blood*, 82(5):1395-1401 (1993).
Milili et al., "The VDJ Repertoire Expressed in Human preB Cells Reflects the Selection of Bona Fide Heavy Chains," *Eur. J. Immunol.*, 26:63-69 (1996).
Milligan, "G Protein-Coupled Receptor Dimerization: Function and Ligand Pharmacology," *Mol. Pharm.*, 66:1-7 (2004).
Mizushima et al., "pEF-BOS, a Powerful Mammalian Expression Vector," *Nucleic Acids Research*, 18(17):5322 (1990).
Mori et al., "Human normal hepatocytes are susceptible to apoptosis signal mediated by both TRAIL-R1 and TRAIL-R2," *Cell Death and Differentiation*, 11:203-207 (2004).
Mulligan et al., "Synthesis of Rabbit β-Globin in Cultured Monkey Kidney Cells Following Infection with a SV40 β-Globin Recombinant Genome," *Nature*, 277:108-114 (1979).
Nakayama et al., "Thrombocytosis in preterm infants: a possible involvement of thrombopoietin receptor gene expression," *Journal of Molecular Medicine*, 83:316-320 (2005).
O'Brien et al., "Monoclonal antibodies for the human insulin receptor stimulate intrinsic receptor-kinase activity," *Biochim. Soc. Trans.*, 14(6):1021-1023 (1986).
Ohtsuka et al., "Synergistic induction of tumor cell apoptosis by death receptor antibody and chemotherapy agent through JNK/p38 and mitochondrial death pathway," *Oncogene*, 22:2034-2044 (2003).
Pan et al., "An Antagonist Decoy Receptor and a Death Domain-Containing Receptor for TRAIL," *Science*, 277:815-818 (1997).
Pan et al., "The Receptor for the Cytotoxic Ligand TRAIL," *Science*, 276:111-113 (1997).
Paul, *Fundamental Immunology*, Raven Press, NY, Chapter 8, p. 242 (1993).
Paul, *Fundamental Immunology*, 3rd Edition, Raven Press, NY, Chapter 8, pp. 292-295 (1993).
Pettersen et al., "CD47 Signals T Cell Death," *J. Immunol.*, 7031-7040 (1999).
Petterson, "CD47 and death signaling in the immune system," *Apoptosis*, 5:299-306 (2000).
Reff et al., "A review of modifications to recombinant antibodies: attempt to increase efficacy in oncology applications," *Critical Reviews in Oncology and Hematology*, 40:25-35 (2001).
Reinhold et al., "In vivo expression of alternatively spliced forms of integrin-associated protein (CD47)," *J. Cell Science*, 108:3419-3425 (1995).
Reiter et al., "Engineering interchain disulfide bonds into conserved framework regions of Fv fragments: improved biochemical characteristics of recombinant immunotoxins containing disulfide-stabilized Fv," *Protein Engineering*, 7(5):697-704 (1994).
Reiter et al., "Stabilization of the Fv Fragments in Recombinant Immunotoxins by Disulfide Bonds Engineered into Conserved Framework Regions," *Biochemistry*, 33:5451-5459 (1994).

(56) References Cited

OTHER PUBLICATIONS

Riechmann et al., "Reshaping Human Antibodies for Therapy," *Nature*, 332:323-327 (1988).
Roue et al. "Mitochondrial dysfunction in CD47-mediated caspase-independent cell death: ROS production in the absence of cytochrome c and AIF release," *Biochimie.*, 85:741-746 (2003).
Rozsnyay et al., "Phenylarsine oxide (PAO) blocks antigen receptor-induced calcium response and tyrosine phosphorylation of a distinct group of proteins," *Immunology Lett.*, 37(2-3):197-205 (1993).
Rudikoff et al., "Single amino acid substitution altering antigen-binding specificity," *Proceedings of the National Academy of Sciences*, 79:1979-1983 (1982).
Sackstein, "The lymphocyte homing receptors: gatekeepers of the multistep paradigm," *Current Opinion in Hematology*, 12:444-450 (2005).
Sato et al., "Reshaping a Human Antibody to Inhibit the Interleukin 6-Dependent Tumor Cell Growth," *Cancer Research*, 53:851-856 (1993).
Schickel, et al., "Gene for Integrin-Associated Protein (IAP, CD47): Physical Mapping, Genomic Structure, and Expression Studies in Skeletal Muscle," *Biochem. Cell. Biol.*, 80(2):169-176 (2002).
Schmidt et al., "A bivalent single-chain antibody-toxin specific for ErbB-2 and the EGF receptor," *Int. J. Cancer*, 65(4):538-546 (1996).
Schwartz et al., "A 50-kDa Integrin-associated Protein Is Required for Integrin-regulated Calcium Entry in endothelial Cells," *J. Biol. Chem.*, 268(27):19931-19934 (1993).
Scott, "The Problem with Potency," *Nature Biotechnology*, 23(9):1037-1039 (2005).
Sekimoto et al., "Eradication of human myeloma cells by a recombinant HLA class I-specific single chain Fv diabody," *45th Annual Meeting of the American Society of Hematology*, San Diego, CA, USA (Dec. 6-9, 2003).
Sekimoto et al., "Eradication of Human Myeloma Cells by a Recombinant HLA Class I-Specific Single Chain Fv Diabody," *Blood*, 102:932a, XP009106629 (Abstract #3469) (Nov. 2003) [Abstract of the American Society of Hematology 45th Annual Meeting, Dec. 6-9, 2003, San Diego, California].
Sheridan et al., "Control of TRAIL-Induced Apoptosis by a Family of Signaling and Decoy Receptors," *Science*, 277:818-821 (1997).
Shigeta et al., "Sperm-immobilizing monoclonal antibody to human seminal plasma antigens," *Clin. Exp. Immunol.*, 42:458-462 (1980).
Shulman et al., "A better cell line for making hybridomas secreting specific antibodies," *Nature*, 276:269-270 (1978).
Skolnick et al., "From genes to protein structure and function: novel applications of computational approaches in the genomic era," *Trends in Biotechnology*, 18:34-39 (2000).
Souyri et al., "A putative truncated cytokine receptor gene transduced by the myeloproliferative leukemia virus immortalizes hematopoietic progenitors," *Cell*, 63:1137-1147 (1990).
Spaargaren et al., "Antibody-induced Dimerization Activates the Epidermal Growth Factor Receptor Tyrosine Kinase," *The J. Biol. Chem.*, 266(3):1733-1739 (1981).
Stancovski et al., "Mechanistic aspects of the opposing effects of monoclonal antibodies to the ERBB2 receptor on tumor growth," *Proc. Natl. Acad. Sci. USA*, 88:8691-8695 (1991).
Stein et al., "Characterization of humanized IgG4 anti-HLA-DR monoclonal antibody that lacks effector cell functions but retains direct antilymphoma activity and increases the potency of rituximab," *Blood*, 108(8):2736-2744 (2006).
Trowbridge, I.S., "Interspecies Spleen-Myeloma Hybrid Producing Monoclonal Antibodies Against Mouse Lymphocyte Surface Glycoprotein, T200," *J. Exp. Med.*, 148:313-323 (1978).
Vajdos et al., "Comprehensive functional maps of the antigen-binding site of an anti-ErbB2 antibody obtained with shotgun scanning mutagenesis," *Journal of Molecular Biology*, 320:415-428 (2002).
Van Geelen et al., "Differential modulation of the TRAIL receptors and the CD95 receptor in colon carcinoma cell lines," *Br. J. Cancer*, 89(2):363-373 (2003).
Verma et al., "Antibody engineering: Comparison of bacterial, yeast, insect and mammalian expression systems," *Journal of Immunological Methods*, 216:165-181 (1998).
Vernon-Wilson et al., "CD47 is a ligand for rat macrophage membrane signal regulatory protein SIRP (OX41) and human SIRPalpha 1," *Eur. J. Immunol.*, 30:2130-2137 (2000).
Wakalee et al., *Ann. Oncol.* On-line publication (Jul. 24, 2009).
Walczak et al., "TRAIL-R2: A Novel Apoptosis-Mediating Receptor for TRAIL," *EMBO J.*, 16:5386-5397 (1997).
Ward et al., "Binding activities of a repertoire of single immunoglobulin variable domains secreted from *Escherichia coli*," *Nature*, 341:544-546 (1989).
Whitlow et al., "Multivalent Fvs: characterization of single-chain Fv oligomers and preparation of a bispecific Fv," *Protein Eng.*, 7(8):1017-1026 (1994).
Wiley et al., "Identification and Characterization of a New Member of the TNF Family that Induces Apoptosis," *Immunity*, 3:673-682 (1995).
Winkler et al., "Changing the Antigen Binding Specificity by Single Point Mutations of an Anti-p24 (HIV-1) Antibody," *J. Immunol.*, 265:4505-4514 (2000).
Wu et al., "Humanization of a murine monoclonal antibody by simultaneous optimization of framework and CDR residues," *Journal of Molecular Biology*, 294:151-162 (1999).
Xie et al., "Direct Demonstration of MuSK Involvement in Acetylcholine Receptor Clustering Through Identification of Agonist ScFv," *Nature Biotechnology*, 15(8):768-771 (1997).
Yagita et al., "TRAIL and its receptors as targets for cancer therapy," *Cancer Sci.*, 95:777-783 (2004).
Yanabu et al., "Tyrosine phosphorylation and p72syk activation by an anti-glycoprotein 1b monoclonal antibody," *Blood*, 89(5):1590-1598 (1997).
Yarden et al., "Self-phosphorylation of epidermal growth factor receptor: evidence for a model of intermolecular allosteric activation," *Biochemistry*, 26(5):1434-1442 (1987).
Yelton et al., "Fusion of Mouse Myeloma and Spleen Cells," *Current Topics in Microbiology and Immunology*, 81:1-7 (1978).
USPTO Restriction Requirement in U.S. Appl. No. 10/530,696, mailed Oct. 19, 2006, 8 pages.
Fish & Richardson P.C., Response to Restriction Requirement dated Oct. 19, 2006, in U.S. Appl. No. 10/530,696, filed Nov. 16, 2006, 1 page.
USPTO Non-Final Office Action in U.S. Appl. No. 10/530,696, mailed Dec. 21, 2006, 19 pages.
Fish & Richardson P.C., Amendment in Reply to Office Action dated Dec. 21, 2006 in U.S. Appl. No. 10/530,696, filed Apr. 23, 2007, 16 pages.
USPTO Final Office Action in U.S. Appl. No. 10/530,696, mailed Aug. 8, 2007, 13 pages.
USPTO Interview Summary in U.S. Appl. No. 10/530,696, mailed Nov. 26, 2007, 3 pages.
Fish & Richardson P.C., Amendment in Reply to Office Action dated Aug. 8, 2007 in U.S. Appl. No. 10/530,696, filed Dec. 6, 2007, 12 pages.
USPTO Advisory Action in U.S. Appl. No. 10/530,696, mailed Dec. 14, 2007, 3 pages.
USPTO Non-Final Office Action in U.S. Appl. No. 10/530,696, mailed Feb. 5, 2008, 9 pages.
Fish & Richardson, Amendment in Reply to Action dated Feb. 5, 2008 in U.S. Appl. No. 10/530,696, filed Aug. 5, 2008, 7 pages.
USPTO Non-Final Office Action in U.S. Appl. No. 10/530,696, mailed Nov. 17, 2008, 18 pages.
Fish & Richardson, Amendment in Reply to Action dated Nov. 17, 2008 in U.S. Appl. No. 10/530,696, filed Feb. 17, 2009, 14 pages.
USPTO Final Office Action in U.S. Appl. No. 10/530,696, mailed Jun. 8, 2009, 10 pages.
Fish & Richardson, Amendment in Reply to Action dated Jun. 8, 2009 in U.S. Appl. No. 10/530,696, filed Nov. 30, 2009, 10 pages.
USPTO Non-Final Office Action in U.S. Appl. No. 10/530,696, mailed Apr. 23, 2010, 9 pages.

(56) References Cited

OTHER PUBLICATIONS

Fish & Richardson, Amendment in Reply to Action dated Apr. 23, 2010 in U.S. Appl. No. 10/530,696, filed Oct. 22, 2010, 8 pages.
USPTO Non-Final Office Action in U.S. Appl. No. 10/530,696, mailed Jan. 7, 2011, 10 pages.
Fish & Richardson, Amendment in Reply to Action dated Jan. 7, 2011 in U.S. Appl. No. 10/530,696, filed Jun. 2, 2011, 5 pages.
International Search Report for App. Ser. No. PCT/JP2003/013063, mailed Nov. 18, 2003, 2 pages.
International Preliminary Report on Patentability for App. Ser. No. PCT/JP2003/013063, dated Feb. 6, 2004, 4 pages.
European Search Report for App. Ser. No. EP 03 75 1456, dated Apr. 4, 2006, 2 pages.
USPTO Notice of Allowance in U.S. Appl. No. 10/551,504, mailed Dec. 16, 2010, 5 pages.
USPTO Notice of Allowance in U.S. Appl. No. 10/551,504, mailed Mar. 21, 2011, 7 pages.
USPTO Restriction Requirement in U.S. Appl. No. 10/582,176, mailed Oct. 19, 2009, 6 pages.
Fish & Richardson P.C., Response to Restriction Requirement dated Oct. 19, 2009 in U.S. Appl. No. 10/582,176, filed Nov. 4, 2009, 1 page.
USPTO Non-Final Office Action in U.S. Appl. No. 10/582,176, mailed Jan. 25, 2010, 7 pages.
Fish & Richardson P.C., Amendment in Reply to Action dated Jan. 25, 2010 in U.S. Appl. No. 10/582,176, filed Jul. 23, 2010, 11 pages.
USPTO Final Office Action in U.S. Appl. No. 10/582,176, mailed Oct. 29, 2010, 11 pages.
Fish & Richardson P.C., Amendment in Reply to Action dated Oct. 29, 2010 in U.S. Appl. No. 10/582,176, filed Apr. 28, 2011, 10 pages.
International Search Report for App. Ser. No. PCT/JP2004/018499, mailed Jan. 18, 2005, 2 pages.
International Preliminary Report on Patentability for App. Ser. No. PCT/JP2004/018499, dated Jan. 26, 2006, 5 pages.
USPTO Restriction Requirement in U.S. Appl. No. 10/582,413, mailed Jan. 4, 2008, 8 pages.
Fish & Richardson P.C., Response to Restriction Requirement dated Jan. 4, 2008 in U.S. Appl. No. 10/582,413, filed Feb. 4, 2008, 2 pages.
USPTO Non-Final Office Action in U.S. Appl. No. 10/582,413, mailed Mar. 31, 2008, 17 pages.
Fish & Richardson P.C., Amendment in Reply to Action dated Mar. 31, 2008 in U.S. Appl. No. 10/582,413, filed Jun. 30, 2008, 20 pages.
USPTO Interview Summary in U.S. Appl. No. 10/582,413, mailed Jun. 30, 2008, 2 pages.
USPTO Notice of Informal or Non-Responsive Amendment in U.S. Appl. No. 10/582,413, mailed Oct. 20, 2008, 3 pages.
USPTO Interview Summary in U.S. Appl. No. 10/582,413, mailed Nov. 12, 2008, 4 pages.
Fish & Richardson P.C., Amendment in Reply to Notice of Informal or Non-Responsive Amendment dated Oct. 20, 2008 in U.S. Appl. No. 10/582,413, filed Nov. 17, 2008, 10 pages.
USPTO Interview Summary in U.S. Appl. No. 10/582,413, mailed Nov. 25, 2008, 4 pages.
USPTO Interview Summary in U.S. Appl. No. 10/582,413, mailed Dec. 24, 2008, 4 pages.
USPTO Restriction Requirement in U.S. Appl. No. 10/582,413, mailed Mar. 11, 2009, 8 pages.
Fish & Richardson P.C., Response to Restriction Requirement dated Mar. 11, 2009 in U.S. Appl. No. 10/582,413, filed Apr. 8, 2009, 8 pages.
USPTO Final Office Action in U.S. Appl. No. 10/582,413, mailed Jun. 25, 2009, 28 pages.
USPTO Interview Summary in U.S. Appl. No. 10/582,413, mailed Oct. 27, 2009, 4 pages.
USPTO Interview Summary in U.S. Appl. No. 10/582,413, mailed Dec. 2, 2009, 4 pages.
USPTO Non-Final Office Action in U.S. Appl. No. 10/582,413, mailed Apr. 16, 2010, 27 pages.
Fish & Richardson P.C., Amendment in Reply to Action dated Apr. 16, 2010 in U.S. Appl. No. 10/582,413, filed Oct. 15, 2010, 11 pages.
USPTO Final Office Action in U.S. Appl. No. 10/582,413, mailed Dec. 23, 2010, 12 pages.
International Search Report for App. Ser. No. PCT/JP2004/018493, mailed Mar. 22, 2005, 2 pages.
International Preliminary Report on Patentability for App. Ser. No. PCT/JP2004/018493, dated Dec. 20, 2005, 7 pages.
European Search Report for App. Ser. No. EP 04 82 0305, dated Oct. 6, 2008, 3 pages.
USPTO Non-Final Office Action in U.S. Appl. No. 10/582,304, mailed Dec. 9, 2010, 12 pages.
Fish & Richardson P.C., Amendment in Reply to Action dated Dec. 9, 2010 in U.S. Appl. No. 10/582,304, filed May 27, 2011, 5 pages.
USPTO Restriction Requirement in U.S. Appl. No. 12/874,872, mailed Dec. 15, 2010, 6 pages.
Fish & Richardson P.C., Reply to Restriction Requirement dated Dec. 15, 2010 in U.S. Appl. No. 12/874,872, filed Jan. 18, 2011, 8 pages.
USPTO Restriction Requirement in U.S. Appl. No. 10/548,727, mailed Apr. 12, 2007, 6 pages.
Fish & Richardson P.C., Reply to Restriction Requirement dated Apr. 12, 2007 in U.S. Appl. No. 10/548,727, filed May 3, 2007, 1 page.
USPTO Non-Final Office Action in U.S. Appl. No. 10/548,727, mailed Aug. 3, 2007, 21 pages.
Fish & Richardson P.C., Amendment in Reply to Action dated Aug. 3, 2007 in U.S. Appl. No. 10/548,727, filed Jan. 15, 2008, 15 pages.
USPTO Final Office Action in U.S. Appl. No. 10/548,727, mailed Apr. 29, 2008, 23 pages.
USPTO Advisory Action in U.S. Appl. No. 10/548,727, mailed Sep. 24, 2008, 6 pages.
USPTO Non-Final Office Action in U.S. Appl. No. 10/548,727, mailed Jan. 28, 2009, 16 pages.
Fish & Richardson P.C., Amendment in Reply to Action dated Jan. 28, 2009 in U.S. Appl. No. 10/548,727, filed Jun. 26, 2009, 9 pages.
USPTO Notice of Allowance in U.S. Appl. No. 10/548,727, mailed Nov. 25, 2009, 29 pages.
International Search Report for App. Ser. No. PCT/JP2004/003334, mailed Jun. 15, 2004, 3 pages.
International Preliminary Report on Patentability for App. Ser. No. PCT/JP2004/003334, dated May 2, 2005, 6 pages.
International Search Report for App. Ser. No. PCT/JP2004/005152, mailed Jul. 20, 2004, 2 pages.
International Preliminary Report on Patentability for App. Ser. No. PCT/JP2004/005152, dated Feb. 14, 2005, 6 pages.
European Search Report for App. Ser. No. EP 04 72 6750, dated Feb. 4, 2008, 3 pages.
USPTO Non-Final Office Action in U.S. Appl. No. 11/547,747, mailed Jun. 1, 2009, 41 pages.
Fish & Richardson P.C., Amendment in Reply to Action dated Jun. 1, 2009 in U.S. Appl. No. 11/547,747, filed Nov. 30, 2009, 12 pages.
USPTO Final Office Action in U.S. Appl. No. 11/547,747, mailed Feb. 19, 2010, 15 pages.
Fish & Richardson P.C., Amendment in Reply to Action dated Feb. 19, 2010 in U.S. Appl. No. 11/547,747, filed Jun. 18, 2010, 13 pages.
USPTO Restriction Requirement in U.S. Appl. No. 10/582,654, mailed May 26, 2009, 9 pages.
Klarquist Sparkman, LLP Response to Restriction Requirement dated May 26, 2009 in U.S. Appl. No. 10/582,654, filed Jun. 23, 2009, 2 pages.
USPTO Office Action in U.S. Appl. No. 10/582,654, mailed Sep. 1, 2009, 36 pages.
Klarquist Sparkman, LLP Amendment in Reply to Action dated Sep. 1, 2009 in U.S. Appl. No. 10/582,654, filed Feb. 26, 2010, 11 pages.
USPTO Final Office Action in U.S. Appl. No. 10/582,654, mailed Apr. 6, 2010, 15 pages.
Klarquist Sparkman, LLP Amendment in Reply to Action dated Apr. 6, 2010 in U.S. Appl. No. 10/582,654, filed Sep. 21, 2010, 7 pages.

(56) References Cited

OTHER PUBLICATIONS

Fish & Richardson P.C., Amendment and Response to Restriction Requirement dated Jul. 1, 2010 in U.S. Appl. No. 11/916,979, filed Nov. 30, 2010, 9 pages.
USPTO Non-Final Office Action in U.S. Appl. No. 11/916,979, mailed Jan. 21, 2011, 15 pages.
Loffler, "A recombinant bispecific single-chain antibody, CD19 x CD3, induces rapid and high lymphoma-directed cytotoxicity by unstimulated T lymphocytes," *Blood*, 95(6):2098-2103 (2000).
Fish & Richardson P.C., Amendment and Response to Restriction Requirement dated Sep. 3, 2010 in U.S. Appl. No. 11/916,351, filed Dec. 2, 2010, 9 pages.
USPTO Non-Final Office Action in U.S. Appl. No. 11/916,351, mailed Mar. 3, 2011, 11 pages.
Fish & Richardson P.C., Amendment in Reply to Action dated Jan. 21, 2011 in U.S. Appl. No. 11/916,979, filed Jul. 14, 2011, 20 pages.
USPTO Non-Final Office Action in U.S. Appl. No. 11/916,981, mailed Dec. 3, 2010, 8 pages.
Fish & Richardson P.C., Amendment in Reply to Action dated Dec. 3, 2010 in U.S. Appl. No. 11/916,981, filed Jun. 2, 2011, 18 pages.
Engelmann et al., "Antibodies to a soluble form of a tumor necrosis factor (TNF) receptor have TNF-like activity," *J. Biol. Chem.*, 265:14497-14504 (1990).
Iliades et al., "Triabodies: single chain Fv fragments without a linker form trivalent trimmers," *FEBS Lett.*, 409:437-441 (1997).
Klarquist Sparkman, LLP Amendment in Reply to Action dated Mar. 26, 2012 in U.S. Appl. No. 10/582,654, filed Sep. 26, 2012, 5 pages.
Arndt et al., "Antigen binding and stability properties of non-covalently linked anti-CD22 single-chain Fv dimers," *FEBS Lett.*, 578(3):257-261 (2004).
Bork et al., "The immunoglobulin fold. Structural classification, sequence patterns and common core," *J. Mol. Biol.*, 242(4):309-320 (1994).
Colcher et al., "Single-chain antibodies in pancreatic cancer," *Ann N Y Acad. Sci.*, 880:263-280 (1999).
USPTO Final Office Action in U.S. Appl. No. 10/582,654, mailed Mar. 26, 2012, 10 pages.
Spada et al., "Reproducing the Natural Evolution of Protein Structural Features with the Selectively Infective Phage (SIP) Technology. The Kink in the First Strand of Antibody kappa Domains," *J. Mol. Biol.*, 283:395-407 (1998).
Wörn et al., "Different Equilibrium Stability Behavior of ScFv Fragments: Identification, Classification, and Improvement by Protein Engineering," *Biochemistry*, 38:8739-8750 (1999).
Kubo et al., "A human monoclonal antibody that detects HLA-A1, A23 and A24 antigens," *Tissue Antigens*, 41:186-189 (1993).
Mulder et al., "A human monoclonal antibody against HLA-Cw1 and a human monoclonal antibody against an HLA-A locus determinant derived from a single uniparous female," *Tissue Antigens*, 52:393-396 (1998).
Scheinberg et al., "Inhibition of cell proliferation with an HLA-A-specific monoclonal antibody," *Tissue Antigens*, 38:213-223 (1991).
Wang et al., "Specificity and functional characteristics of anti-HLA-A mAbs LGIII-147.4.1 and LGIII-220.6.2," *Tissue Antigens*, 62:139-148 (2003).
Fish & Richardson P.C., Amendment in Reply to Action dated Oct. 28, 2011 in U.S. Appl. No. 11/916,351, filed Apr. 30, 2012, 28 pages.
Fish & Richardson P.C., Amendment in Reply to Action dated Sep. 12, 2011 in U.S. Appl. No. 11/916,981, filed May 8, 2012, 6 pages.
International Search Report for App. Ser. No. PCT/JP2010/066494, mailed Dec. 28, 2010, 6 pages.
International Preliminary Report on Patentability for App. Ser. No. PCT/JP2010/066494, dated Apr. 11, 2012, 8 pages.
Lederman et al., "A single amino acid substitution in a common African allele of the CD4 molecule ablates binding of the monoclonal antibody, OKT4," *Mol. Immunol.*, 28:1171-1181 (1991).
Li et al., "beta-Endorphin omission analogs: dissociation of immunoreactivity from other biological activities," *Proc. Natl. Acad. Sci. U.S.A.*, 77:3211-3214 (1980).
USPTO Non-Final Office Action in U.S. Appl. No. 10/582,654, mailed Aug. 25, 2011, 15 pages.
Crocker et al., "Siglecs in the immune system," *Immunology*, 103:137-45 (2001).
Fearon et al., "Regulation of B lymphocyte responses to foreign and self-antigens by the CD19/CD21 complex," *Annu. Rev. Immunol.*, 18:393-422 (2000).
Graus-Porta et al., "ErbB-2, the preferred heterodimerization partner of all ErbB receptors, is a mediator of lateral signaling," EMBO J., 16:1647-1655 (1997).
Hymowitz et al., "Triggering cell death: the crystal structure of Apo2L/TRAIL in a complex with death receptor 5," *Mol. Cell*, 4:563-571 (1999).
Fish & Richardson P.C., Amendment in Reply to Action dated Sep. 16, 2011 in U.S. Appl. No. 11/916,979, filed Mar. 15, 2012, 15 pages.
Carrel et al., "Recognition of HLA-A1 by murine monoclonal antibodies," *Tissue Antigens.*, 43:110-115 (1994).
USPTO Restriction Requirement in U.S. Appl. No. 13/497,545, dated Feb. 26, 2013, 8 pages.
Armijos et al., "Comparison of the effectiveness of two topical paromomycin treatments versus meglumine antimoniate for New World cutaneous leishmaniasis," *Acta Trop.*, 91(2):153-60 (2004).
Friton et al., "Clinical efficacy of meloxicam (Metacam) and flunixin (Finadyne) as adjuncts to antibacterial treatment of respiratory disease in fattening cattle," *Berl. Munch Tierarztl. Wochenschr.*, 117(7-8):304-9 (2004).
Goyen et al., "Gadobenate dimeglumine (MultiHance) for magnetic resonance angiography: review of the literature," *Eur. Radiol.*, 13 Suppl 3:N19-27 (2003).
Grossman et al., "Multiple sclerosis: gadolinium enhancement in MR imaging," *Radiology*, 161(3):721-5 (1986).
The Protein Protocols Handbook, second edition, edited by John M. Walker, Springer-Verlag, New York, LLC, 1035-1046 (2002).
USPTO Non-Final Office Action in U.S. Appl. No. 11/916,979, mailed May 14, 2014, 20 pages.
Kashmiri et al., Generation, characterization, and in vivo studies of humanized anticarcinoma antibody CC49, *Hybridoma*, Oct. 1995;14(5):461-473.
McCall et al., "Isolation and characterization of an anti-CD16 single-chain Fv fragment and construction of an anti-HER2/neu/anti-CD16 bispecific scFv that triggers CD16-dependent tumor cytolysis," *Mol Immunol.*, May 1999;36:433-446.
Santos et al., "Generation and characterization of a single gene-encoded single-chain-tetravalent antitumor antibody," *Clin Cancer Res.*, Oct. 1999;5:3118s-3123s.
USPTO Non-Final Office Action in U.S. Appl. No. 11/916,351, mailed Jan. 15, 2015, 12 pages.
Ausubel et al., Short Protocols in Molecular Biology, 3rd Edition, 1995, pp. 11-27.
Goel et al., "Divalent forms of CC49 single-chain antibody constructs in Pichia pastoris: expression, purification, and characterization," *J. Biochem.*, May 2000;127(5):829-36.
Fish & Richardson P.C., Amendment in Reply to Action dated May 14, 2014 in U.S. Appl. No. 11/916,979, filed Nov. 13, 2014, 15 pages.
USPTO Final Office Action in U.S. Appl. No. 11/916,979, mailed Dec. 5, 2014, 18 pages.
USPTO Notice of Allowance in U.S. Appl. No. 11/916,979, mailed Sep. 15, 2015, 5 pages.
Fish & Richardson P.C., Amendment in Reply to Action dated Jan. 15, 2015 in U.S. Appl. No. 11/916,351, filed Feb. 12, 2016, 14 pages.
Ausubel et al., Short Protocols in Molecular Biology, 3rd Edition, 1985, p. A1-44.
Humes et al., "Direct toxic effect of the radiocontrast agent diatrizoate on renal proximal tubule cells," *Am. J. Physiol.*, 252(2):F246-F255 (1987).
Lower, Chemical Equilibrium, A Chem1 Reference Text, 2001, pp. 1-28.

(56) References Cited

OTHER PUBLICATIONS

USPTO Final Office Action in U.S. Appl. No. 11/916,981, mailed Sep. 12, 2011, 10 pages.
USPTO Final Office Action in U.S. Appl. No. 11/916,979, mailed Sep. 16, 2011, 20 pages.
USPTO Final Office Action in U.S. Appl. No. 11/916,351, mailed Oct. 28, 2011, 10 pages.
USPTO Restriction Requirement in U.S. Appl. No. 12/307,042, mailed Dec. 6, 2011, 9 pages.
USPTO Notice of Allowance in U.S. Appl. No. 10/530,696, mailed Dec. 12, 2011, 8 pages.
Klarquist Sparkman, LLP Amendment in Reply to Action dated Aug. 25, 2011 in U.S. Appl. No. 10/582,654, filed Feb. 13, 2012, 6 pages.
Chemical Book (chemicalbook.com, "DR5" definition), p. 1 (Jun. 7, 2013).
Devito et al., "Epitope fine specificity of human anti-HLA-A2 antibodies. Identification of four epitopes including a haptenlike epitope on HLA-A2 at lysine 127," *Hum. Immunol.*, 37:165-177 (1993).
Heppner et al., "Tumor heterogeneity: biological implications and therapeutic consequences," *Cancer Metastasis Rev.*, 2:5-23 (1983).
Kornbluth et al., "Evidence for the role of class I and class II HLA antigens in the lytic function of a cloned line of human natural killer cells," *J. Immunol.*, 134:728-735 (1985).
Lozano et al., "Identification of the amino acid residues defining an intralocus determinant in the alpha 1 domain of HLA-A molecules," *Immunogenetics*, 30:50-53 (1989).
Rowe et al., "Handbook of Pharmaceutical Excipients, $4^{th}$ ed.," 381-382 (2003), Published by the Pharmaceutical Press and the American Pharmaceutical Association.
Spear et al., "Evidence for a shared HLA-A intralocus determinant defined by monoclonal antibody 131," *J. Exp. Med.*, 162:1802-1810 (1985).
USPTO Non-Final Office Action in U.S. Appl. No. 14/967,475, dated May 19, 2016, 20 pages.
Pettersen et al., "Role of the TCR Binding Region of the HLA Class I alpha2 Domain in Regulation of Cell Adhesion and Proliferation," *J Immunol.*, Feb. 15, 1996;156(4):1415-24.
Retter et al., Both Sm and DNA are Selecting Antigens in the Anti-Sm B Cell Response in Autoimmune MRL//pr Mice, *J Immunol.*, Feb. 1, 1996;156(3):1296-306.
Sekine et al., Enrichment of Anti-Glomerular Antigen Antibody-Producing Cells in the Kidneys of MRL/MpJ-Fas(lpr) Mice, *J Immunol.*, Mar. 15, 2004;172(6):3913-21.
Fish & Richardson P.C., Amendment in Reply to Action dated Dec. 5, 2014 in U.S. Appl. No. 11/916,979, filed Aug. 26, 2015, 13 pages.

\* cited by examiner

FIG. 18
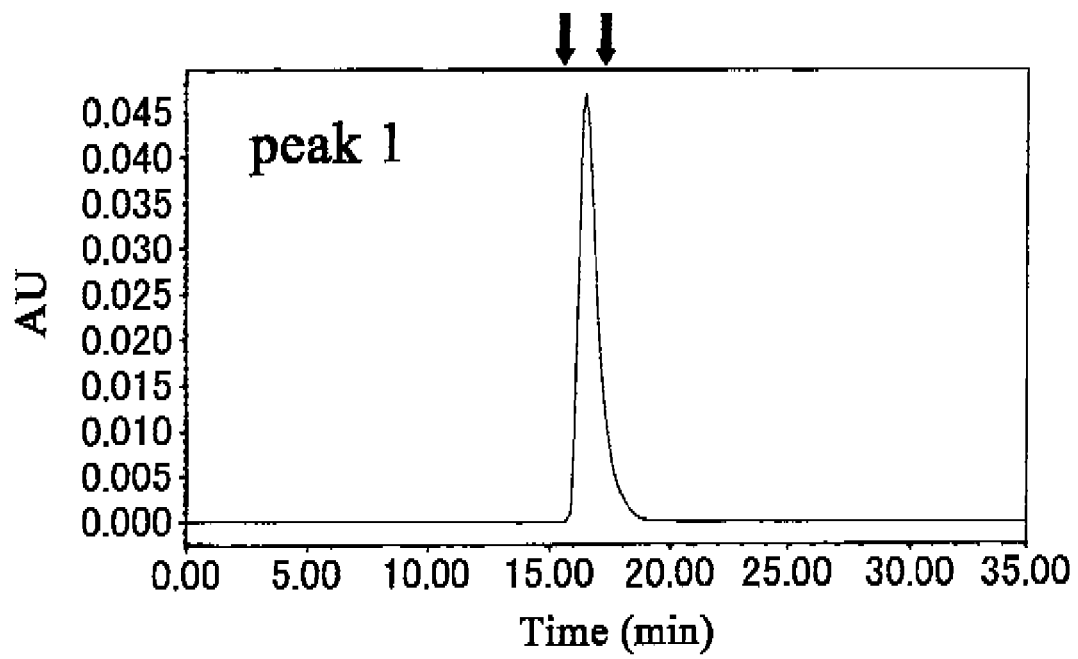
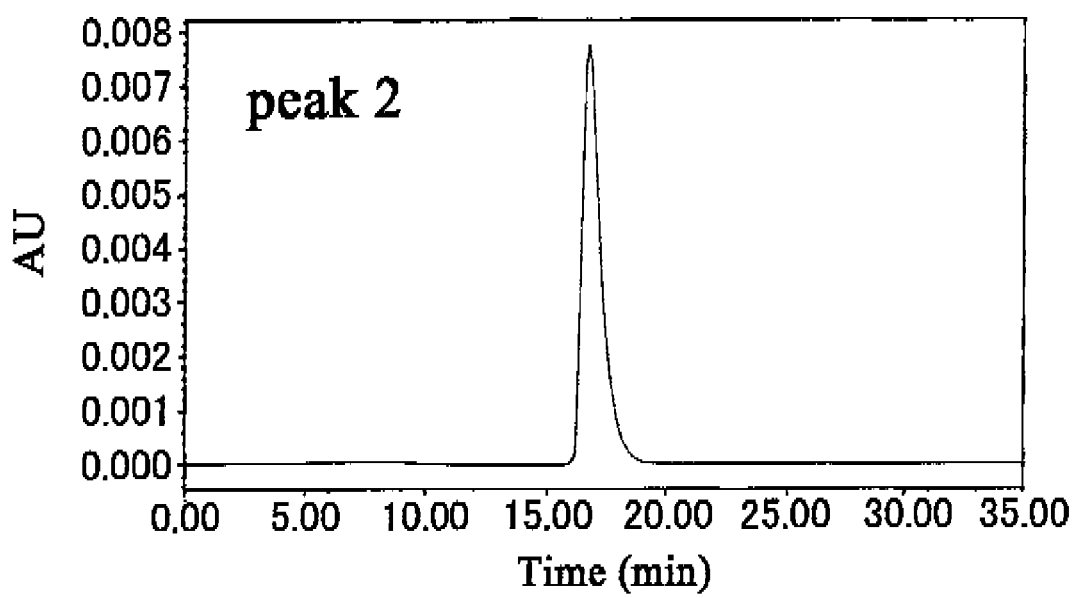

FIG. 23
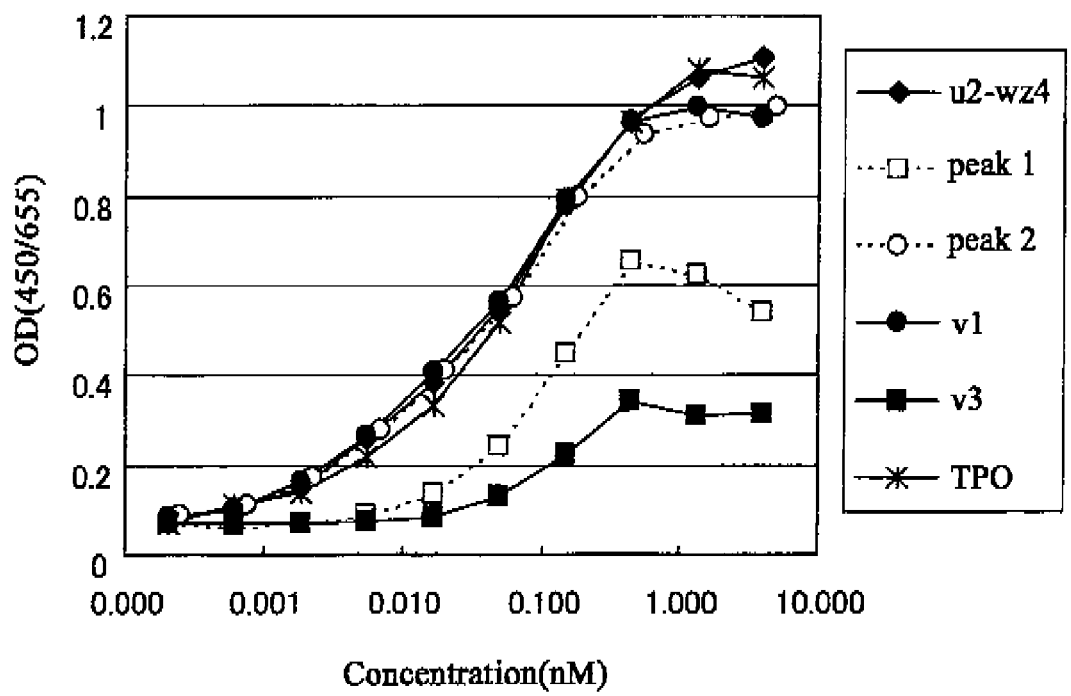
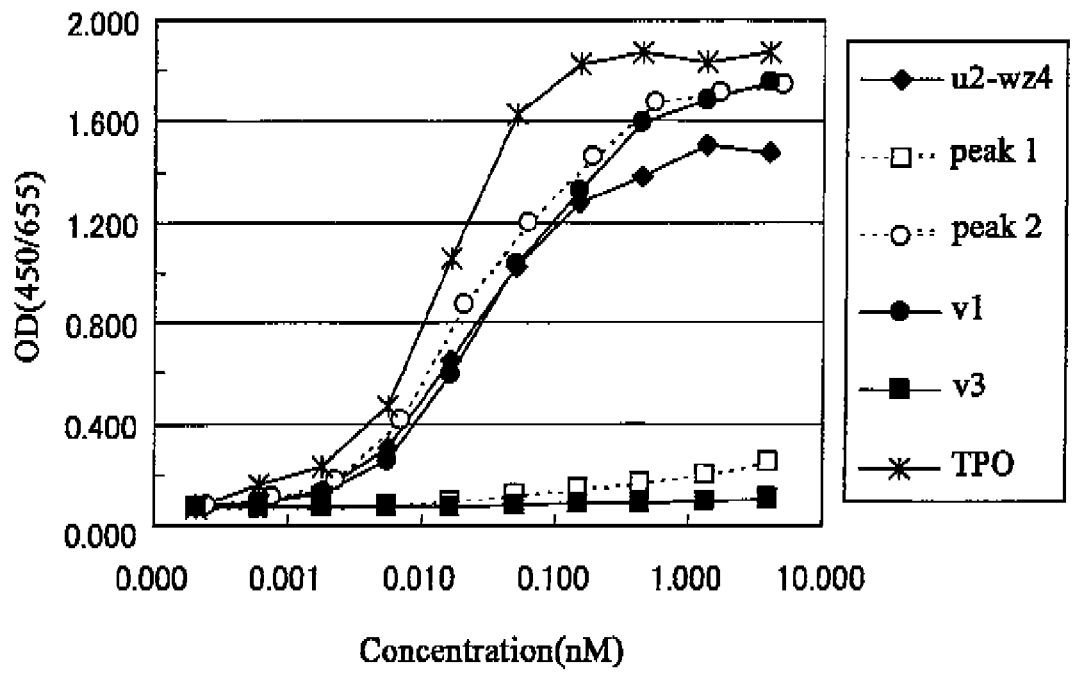

FIG. 24
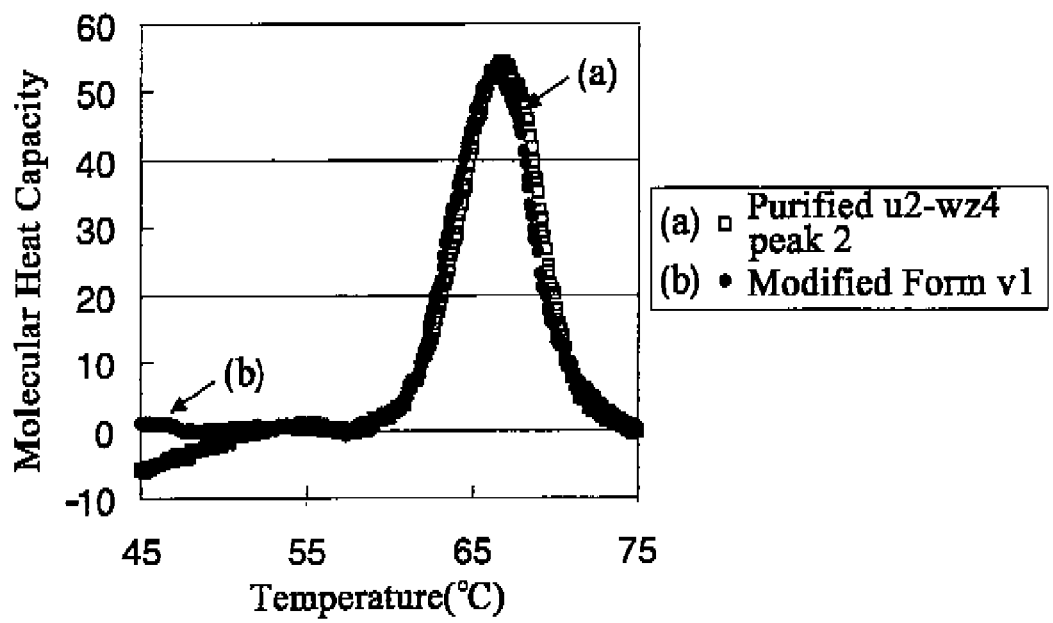
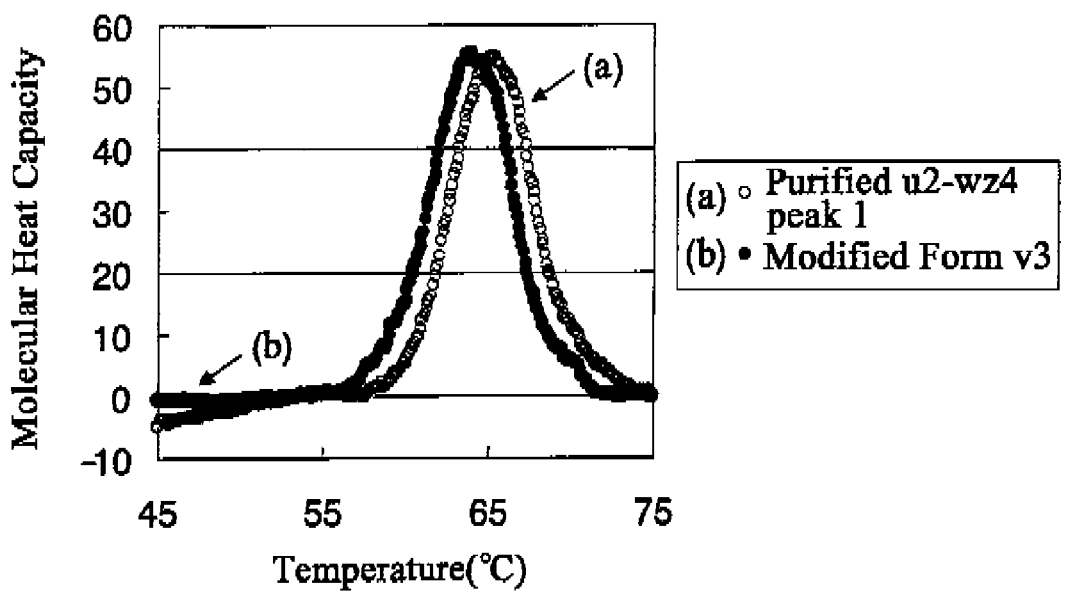

STRUCTURAL ISOMERS OF SC(FV)2

CROSS-REFERENCE TO RELATED APPLICATIONS

This application is the National Stage of International Application No. PCT/JP2006/306800, filed on Mar. 31, 2006, which claims the benefit of Japanese Patent Applications Ser. No. 2005/101711, filed on Mar. 31, 2005, and Ser. No. 2005/378467, filed on Dec. 28, 2005. The contents of all of the foregoing applications are hereby incorporated by reference in their entireties.

TECHNICAL FIELD

The present invention relates to pharmaceutical compositions comprising sc(Fv)2 and methods for producing the compositions.

BACKGROUND ART sc(Fv)2s are single-chain antibodies in which two light chain variable regions (VL) and two heavy chain variable regions (VH), four variable regions in total, are linked by linkers or such (Hudson et al., J. Immunol. Methods (1999) 231: 177-189).

For example, single-chain antibodies having the sequence $VH_1$-linker-$VL_2$-linker-$VH_3$-linker-$VL_4$ or $VL_2$-linker-$VH_1$-linker-$VL_4$-linker-$VH_3$ are known. Depending on the combination of Fv (a molecule in which VH and VL are non-covalently linked), two types of structural isomers of sc(Fv)2 would exist: sc(Fv)2 in which each set of Fv is formed by $VH_1$ and $VL_2$, and $VH_3$ and $VL_4$; and sc(Fv)2 in which each set of Fv is formed by $VH_1$ and $VL_4$, and $VH_3$ and $VL_2$.

However, since most previous studies on sc(Fv)2 dealt with bispecific sc(Fv)2s, to date there are almost no reports on structural isomers of sc(Fv)2.

Bispecific sc(Fv)2s are sc(Fv)2s in which the variable regions of $VH_1$ and $VL_4$, and $VH_3$ and $VL_2$ (or $VH_1$ and $VL_2$, and $VL_3$ and $VL_4$) in the $VH_1$-linker-$VL_2$-linker-$VH_3$-linker-$VL_4$ sequence derive from different monoclonal antibodies. In bispecific sc(Fv)2s, $VH_1$ and $VL_4$, or $VH_3$ and $VL_2$ (or $VH_1$ and $VL_2$, or $VH_3$ and $VL_4$) derive from an identical monoclonal antibody. In this case, the efficiency of Fv formation would be higher and therefore the occurrence of structural isomers is suppressed to some extent. In fact, the activity was reported to remain unchanged between bispecific sc(Fv)2s prepared using linkers whose lengths were 15-5-15 and 15-15-15 (Non-patent Document 5). Thus, there is a lack of detailed information regarding structural isomers of sc(Fv)2. For example, Non-patent Documents 3, 4, 8, and 9 indicate the existence of correct Fv combinations confirmed by measuring bispecific binding activities; however, neither a quantitative evaluation regarding the abundance of incorrect Fv combinations nor abundance ratio between the two has been described. Meanwhile, Non-patent Document 6 demonstrates that structural transition between the monomer and the dimer occurs by alteration of lengths of bispecific sc(Fv)2 linkers (alteration of the lengths of linkers at the two ends or in the middle). However, when it comes to structural isomers of sc(Fv)2, the document does not go beyond a discussion on a model-based molecular structure prediction, and describes neither the abundance ratio of the structural isomers nor structural identification in actual samples.

Furthermore, since no attention was focused on structural isomers of sc(FV)2, no close examination on regulating structural isomers was conducted. Non-patent Document 10 also predicts that structures of single chain diabody and bivalent scFv are formed when the length of the linkers are 5-15-5 and 15-5-15, respectively. This is because it has been generally reported in scFvs that adjacent VH and VL are unlikely to form an Fv (i.e., a monomer) when the length of the linker is 12 or shorter. However, Non-patent Document 2 reports that a small quantity of monomers is formed even when the length of the linker in the Fv is 10 or 5. Thus, in the case of Non-patent Document 10, where the linker length is 5-15-5 or 15-5-15, the obtained sc(Fv)2s are not always all in the structural form of single chain diabody or bivalent scFv.

Previous reports evaluated structural isomers by structural prediction based solely upon Fv combinations and linker length. No quantitative analysis of the structural isomer content ratio was conducted. In addition, the obtained structure was not confirmed/verified to see if it was the objective structure. Thus, structural isomers were neither evaluated nor regulated in a sufficient manner. Specifically, regardless of the length, the abundance ratio of the structural isomers of sc(Fv)2 is extremely difficult to predict based on Fv combinations and linker length. The presence of two types of structural isomers is a issue that has to be taken into consideration when sc(Fv)2 molecules comprise two pairs of VH and VL.

There are many known separation methods for optical isomers and geometric isomers of minibody compounds. However, to date there are no reported methods for separating protein isomers. Many methods for separating single amino acid variations in proteins have been previously reported; however, to date, no reports on methods for separating two structural isomers comprising a completely identical amino acid primary sequence is known. The same is true for structural isomers of sc(Fv)2s, and thus, no methods for separating and analyzing, or confirming the two types of structural isomers of sc(Fv)2 existed in prior art.

Since no method was available for separating structural isomers of sc(Fv)2, there are no reports focusing on difference in activity between the two types of structural isomers. In bispecific sc(Fv)2, the activity is obviously predicted to be significantly different between the correct and incorrect Fv combinations within the structural isomers. It is however difficult to predict activity differences between the structural isomers of monospecific sc(Fv)2s that are divalent as well. Non-patent Document 10 ignores the potential differences in activity between the two structural isomers and measures activity (binding activity) using a mixture of the structural isomers. This is because the activity between each structural isomer of sc(Fv)2 could not be strictly compared since highly purified structural isomers could not be prepared because of the difficulty in separation and purification of sc(Fv)2 structural isomers.

Even for sc(Fv)2s with altered linker length, until now it has also been impossible to "identify" (rather than "predict") each of the two types of structural isomers presumed from linker length and to quantitatively evaluate the content ratio of the structural isomers. Thus, to date, no quantitative evaluation has been performed to reveal the relationship between linker length and content ratio of the structural isomers in sc(Fv)2. Therefore, there are substantially no reports describing the regulation of content ratio of structural isomers by altering linker length.

Alteration of linker length results in the alternation of the distance between the two antigen-binding sites in sc(Fv)2, and thus, linker length has a possible influence on biological activity (agonistic activity such as receptor dimerization). It is thus preferable that the distance between the two antigen-binding sites be arbitrarily adjusted by the lengths of the linkers depending on the type of antigen. Furthermore, linker length has been reported to have a great influence on stability (Non-patent Documents 1 and 2) and the stability of scFvs is known to generally decrease as linkers get shorter. The same would be true for sc(Fv)2s. It is reported that dimers are easily formed by shortening the middle linker (Non-patent Document 6). For the preparation of a highly stable sc(Fv)2, linker lengths that can be arbitrarily adjustable are preferred. When sc(Fv)2s are developed as pharmaceuticals, it is thus preferable that target structural isomers be isolated by their arbitrary linker lengths. However, there are no previous reports describing the isolation of each of the two types of structural isomers, bivalent scFv and single chain diabody, from sc(Fv)2s with linkers of arbitrary lengths.

To develop sc(Fv)2s comprising structural isomers as pharmaceuticals, it is necessary to separate and purify only the targeted structural isomer and to manufacture a bulk drug which comprises only one of the structural isomers. Alternatively; when such a bulk drug is a mixture of structural isomers, it is required to determine the properties of the two types of structural isomers and to conduct a specification test to quantitatively analyze the content ratio of the respective structural isomers. However, to date, there are no known methods for separating and purifying, quantitatively analyzing, or identifying the structural isomers of sc(Fv)2s.

Meanwhile, some reports describe methods for controlling the abundance ratio of monomer/dimer/trimer/tetramer of scFv based on linker length. However, to date, there are no reports describing methods for controlling the abundance ratio of structural isomers by altering linker length because no methods for quantitatively analyzing the structural isomers of sc(Fv)2 have been discovered, as described above.

Non-patent Document 1: Protein Engineering, 1993, 6(8), 989-995
Non-patent Document 2: Protein Engineering, 1994, 7(8), 1027-1033
Non-patent Document 3: Journal of Immunology, 1994, 152, 5368-5374
Non-patent Document 4: Journal of Immunology, 1995, 154, 4576-4582
Non-patent Document 5: PNAS, 1995, 92, 7021-7025
Non-patent Document 6: Journal of Molecular Biology, 1999, 293, 41-56
Non-patent Document 7: Protein Engineering, 2001, 14(10), 815-823
Non-patent Document 8: Journal of Molecular Biology, 2003, 330, 99-111
Non-patent Document 9: Protein Eng Des Sel. 2004 April, 17(4), 357-66
Non-patent Document 10: Clinical Cancer Research, 2004, 10, 1274-1281
Non-patent Document 11: Int. J. Cancer, 1998, 77, 763-772

DISCLOSURE OF THE INVENTION

Problems to be Solved by the Invention

The present invention was achieved in view of such circumstances. An objective of the present invention is to provide, pharmaceutical compositions comprising as an active ingredient a specific structural isomer of sc(Fv)2, methods for producing the compositions, and methods for determining structure and specification testing of such structural isomers for developing pharmaceuticals. An alternative objective is to provide methods for increasing the proportion of a specific structural isomer in sc(Fv)2 compositions, methods for increasing the activity of sc(Fv)2 compositions using such methods, and methods for analyzing the structural isomers in sc(Fv)2 compositions.

Means for Solving the Problems

The structural isomers of human Mpl antibody and humanized anti-human Mpl antibody were confirmed to be of single chain diabody type and bivalent scFv type by separating the structural isomers from the sc(Fv)2 compositions and by cleaving the liner(s) or the region adjacent to the linker(s) of the obtained isomers. In addition, the agonistic activity was found to be markedly different between these structural isomers.

The present inventors also discovered that the content ratio of the structural isomers in sc(Fv)2 compositions can be regulated by altering the linker length of sc(Fv)2s.

The present invention provides the following [1] to [44]:
[1] a method for producing a pharmaceutical sc(Fv)2 composition comprising the steps of:
(a) separating structural isomers in the sc(Fv)2 composition, and
(b) obtaining a specific structural isomer from the separated structural isomers;
[2] a method for producing a pharmaceutical sc(Fv)2 composition comprising the steps of:
(a) pre-identifying a structural isomer with higher activity by comparing the activities of structural isomers of sc(Fv)2;
(b) separating structural isomers in the sc(Fv)2 composition; and
(c) obtaining the structural isomer with higher activity identified in step (a);
[3] a method for producing a pharmaceutical sc(Fv)2 composition comprising the steps of:
(a) determining a linker length so that the structural isomer ratio in an sc(Fv)2 composition would be of a preferred value;
(b) preparing a sc(Fv)2 composition that has the linker length determined in step (a);
(c) separating structural isomers in the prepared sc(Fv)2 composition; and
(d) obtaining a specific structural isomer from the separated structural isomers;
[4] a method for producing a pharmaceutical sc(Fv)2 composition comprising the steps of:
(a) preparing multiple sc(Fv)2 compositions with linkers of varying lengths;
(b) selecting an sc(Fv)2 with linker(s) that give a preferred of structural isomer ratio in an sc(Fv)2 composition;
(c) preparing an sc(Fv)2 composition in which the linker lengths are the same as those of sc(Fv)2 selected in step (b);
(d) separating the structural isomers in the prepared sc(Fv)2 composition; and
(e) obtaining a specific structural isomer from the separated structural isomers;
[5] the method of any one of [1] to [4] wherein the structural isomer is of single chain diabody type or bivalent scFv type;
[6] the method of any one of [1] to [5], wherein the structural isomer has an agonistic activity;
[7] the method of any one of [1] to [6], wherein a linker of sc(Fv)2 is 15 amino acids in length;

[8] a pharmaceutical composition prepared by the production method of any one of [1] to [7];
[9] a pharmaceutical composition, wherein the proportion of a specific structural isomer in an sc(Fv)2 composition is 80% or greater;
[10] the pharmaceutical composition of [9], wherein the structural isomer is of single chain diabody type or bivalent scFv type;
[11] the pharmaceutical composition of [9] or [10], wherein the structural isomer binds to a receptor;
[12] the pharmaceutical composition of any one of [9] to [11], wherein the structural isomer has an agonistic activity;
[13] the pharmaceutical composition of [9] to [12], wherein a her of sc(Fv)2 is 15 amino acids in length;
[14] a method for controlling the activity of an sc(Fv)2 composition comprising the step of altering the structural isomer proportion in the sc(Fv)2 composition;
[15] a method for increasing the activity of an sc(Fv)2 composition comprising the step of increasing the proportion of a specific structural isomer in the sc(Fv)2 composition;
[16] a method for increasing the activity of an sc(Fv)2 composition comprising the steps of:
(a) separating structural isomers in an sc(Fv)2 composition;
(b) obtaining a specific structural isomer from the separated structural isomers;
[17] a method for increasing the activity of an sc(Fv)2 composition comprising the steps of:
(a) pre-identifying a structural isomer with higher activity by comparing the activities of structural isomers of sc(Fv)2;
(b) separating structural isomers in the sc(Fv)2 composition; and
(c) obtaining the structural isomer with higher activity that was identified in step (a);
[18] a method for increasing the activity of an sc(Fv)2 composition comprising the steps of:
(a) applying an sc(Fv)2 composition onto an ion exchange column; and
(b) removing a specific structural isomer;
[19] the method of any one of [14] to [18], wherein the structural isomer is of single chain diabody type or bivalent scFv type;
[20] a method for increasing the content ratio of a specific structural isomer in an sc(Fv)2 composition which comprises the step of heating the sc(Fv)2 composition;
[21] the method of [20], wherein the structural isomer is of single chain diabody type or bivalent scFv type;
[22] a method for increasing the content ratio of the single chain diabody type in an sc(Fv)2 composition, comprising the step of incubating the sc(Fv)2 composition at 15° C. to 50° C.;
[23] a method for increasing the content ratio of a specific structural isomer in an sc(Fv)2 composition, which comprises the step of substituting, with a charged amino acid residue, an amino acid residue at the contact surface of heavy chain and light chain variable regions in the sc(Fv)2;
[24] a method for increasing the content ratio of a specific structural isomer in an sc(Fv)2 composition, which comprises the step of substituting the following amino acid residues with an amino acid residue having the same type of charge:
(1) the amino acid residue at position 39 in the heavy chain variable region of sc(Fv)2; and
(2) the amino acid residue at position 38 in the amino acid sequence of the light chain variable region of sc(Fv)2;

[25] a method for increasing the content ratio of a specific structural isomer in an sc(Fv)2 composition, which comprises the step of substituting the following amino acid residues with an amino acid residue having the same type of charge:
(1) the amino acid residue at position 45 in the amino acid sequence of the heavy chain variable region of sc(Fv)2; and
(2) the amino acid residue at position 44 in the amino acid sequence of the light chain variable region of sc(Fv)2;
[26] a method for increasing the content ratio of a specific structural isomer in an sc(Fv)2 composition, which comprises the step of substituting either one of the following ammo acid residues with a charged amino acid residue:
(1) the amino acid residue at position 45 in the amino acid sequence of the heavy chain variable region of sc(Fv)2; and
(2) the amino acid residue at position 44 in the amino acid sequence of the light chain variable region of sc(Fv)2;
[27] a method for increasing the activity of an sc(Fv)2 composition, which comprises the step of substituting, with a charged amino acid residue, an amino acid residue at the contact surface of heavy chain and light chain variable regions of sc(Fv)2;
[28] a method for increasing the activity of an sc(Fv)2 composition, comprising the step of substituting the following amino acid residues with an amino acid residue having the same type of charge:
(1) the amino acid residue at position 39 in the heavy chain variable region of sc(Fv)2; and
(2) the amino acid residue at position 38 in the amino acid sequence of the light chain variable region of sc(Fv)2;
[29] a method for increasing the activity of an sc(Fv)2 composition, comprising the step of substituting the following amino acid residues with an amino acid residue having the same type of charge:
(1) the amino acid residue at position 45 in the amino acid sequence of the heavy chain variable region of sc(Fv)2; and
(2) the amino acid residue at position 44 in the amino acid sequence of the light chain variable region of sc(Fv)2;
[30] a method for increasing the activity of an sc(Fv)2 composition comprising the step of substituting either one of the following amino acid residues with a charged amino acid residue:
(1) the amino acid residue at position 45 in the amino acid sequence of the heavy chain variable region of sc(Fv)2; and
(2) the amino acid residue at position 44 in the amino acid sequence of the light chain variable region of sc(Fv)2;
[31] a method for suppressing the isomerization of a structural isomer in an sc(Fv)2 composition, which comprises the step of substituting, with a charged amino acid residue, an amino acid residue at the contact surface of heavy chain and light chain variable regions of sc(Fv)2;
[32] a method for suppressing the isomerization of a structural isomer in an sc(Fv)2 composition, comprising the step of substituting the following amino acid residues with an amino acid residue having the same type of charge:
(1) the amino acid residue at position 39 in the heavy chain variable region of sc(Fv)2; and
(2) the amino acid residue at position 38 in the amino acid sequence of the light chain variable region of sc(Fv)2;
[33] a method for suppressing the isomerization of a structural isomer in an sc(Fv)2 composition, comprising the step of substituting the following amino residues with an amino acid residue having the same type of charge:
(1) the amino acid residue at position 45 in the amino acid sequence of the heavy chain variable region of sc(Fv)2; and
(2) the amino acid residue at position 44 in the amino acid sequence of the light chain variable region of sc(Fv)2;

[34] a method for suppressing the isomerization of a structural isomer in an sc(Fv)2 composition, comprising the step of substituting either one of the following ammo acid residues with a charged amino acid residue:
(1) the amino acid residue at position 45 in the amino acid sequence of the heavy chain variable region of sc(Fv)2; and
(2) the amino acid residue at position 44 in the amino acid sequence of the light chain variable region of sc(Fv)2;

[35] a method for controlling the proportion of a structural isomer in an sc(Fv)2 composition comprising the step of adjusting the length of a linker in sc(Fv)2;

[36] the method of [35], wherein the structural isomer is of a single chain diabody type or bivalent scFv type;

[37] a method for increasing the proportion of the single chain diabody type in an sc(Fv)2 composition, which comprises the step of adjusting the lengths of both end linkers of sc(Fv)2 to 0 to 12 amino acids and the length of the middle linker to 10 to 30 amino acids;

[38] a method for increasing the proportion of the bivalent scFv type in an sc(Fv)2 composition, which comprises the step of adjusting the lengths of both end linkers of sc(Fv)2 to 12 to 30 amino acids and the length of the middle linker to 0 to 10 amino acids;

[39] a method for producing an sc(Fv)2 composition in which the content ratio of a single chain diabody type is 80% or greater, which comprises the step of adjusting the lengths of both end linkers of sc(Fv)2 to 0 to 12 amino acids and the length of the middle linker to 0 to 10 amino acids;

[40] a method for producing an sc(Fv)2 composition in which the content ratio of bivalent scFv type is 80% or greater, which comprises the step of adjusting the lengths of both end linkers of sc(Fv)2 to 12 to 30 amino acids and the length of the middle linker to 0 to 10 ammo acids;

[41] a method for analyzing a structural isomer in an sc(Fv)2 composition, comprising the step of cleaving a linker or a region adjacent to the linker in sc(Fv)2:

[42] the method of [41], wherein the linker or the region nearby the linker is cleaved by a treatment with an enzyme;

[43] the method of [41] or [42], wherein the structural isomer is of a single chain diabody type or bivalent scFv type; and

[44] a method for analyzing a structural isomer in an sc(Fv)2 composition comprising the steps of:
(a) treating the sc(Fv)2 composition with an enzyme; and
(b) determining the molecular weight or structure of the product after treatment.

BRIEF DESCRIPTION OF THE DRAWINGS

FIG. 18 shows results of gel filtration analysis of peak 1 and peak 2 of hVB22B u2-wz4 sc(Fv)2 purified on a large scale.

FIGS. 23A and 23B show results of TPO-like agonistic activity assay for purified u2-wz4 peak 1 and peak 2, and the modified forms v1 and v3 using BaF cells and human Mpl (FIG. 23A) or monkey Mpl (FIG. 23B).

FIG. 24 shows results of DSC analysis of purified u2-wz4 peak 1 and peak 2, and the modified forms v1 and v3.

BEST MODE FOR CARRYING OUT THE INVENTION

Figure 1:
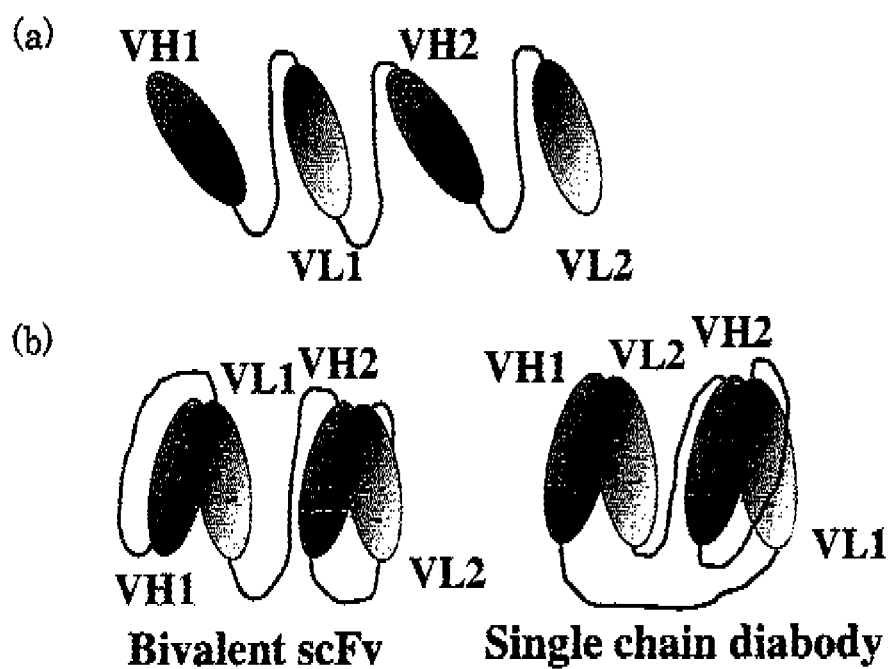
FIG. 1 shows in (a) a diagram illustrating VH1-linker-VL1-linker-VH2-linker-VL2 structure of VB22B sc(Fv)2, and in (0), a diagram showing the two types of structural isomers of the VH1-linker-VL1-linker-VH1-linker-VL2 structure. This diagram shows the bivalent scFv structure (left) in which nil is associated with VL1, and VH2 is associated with VL2; and the single chain diabody structure (right) in which VH1 is associated with VL2, and VH2 is associated with VL1.

In the course of analyzing structural isomers of sc(Fv)2s, the present inventors discovered that there were differences in activity between the structural isomers. Furthermore, the inventors found that the ratio of structural isomers in sc(Fv)2 compositions was adjustable and specific structural isomers could be separately obtained from the sc(Fv)2 compositions. The present invention was achieved based on these findings.

The present invention provides methods for producing pharmaceutical compositions, which comprise steps of separating structural isomers in the sc(Fv)2 compositions and obtaining specific structural isomers from the separated structural isomers.

In the present invention, sc(Fv)2 are single-chain low molecular weight antibodies produced by linking four or more antibody variable regions with linkers and such. The sc(Fv)2 includes, for example, antibodies with the following arrangement: [variable region 1] (linker 1)[variable region 2] (linker 2)[variable region 3] (linker 3)[variable region 4].

Generally, sc(Fv)2 is a single-chain antibody produced by linking two VHs and two VLs, four variable regions in total, with linkers and such (Hudson et al. J Immunol. Methods (1999) 231: 177-189). The two VHs and two VLs may derive from different monoclonal antibodies.

sc(Fv)2s can be produced by methods known to those skilled in the art, for example, by lining scFvs with linkers. scFv contains the VH and VL of an antibody, and these regions exist on a single polypeptide chain (for a review on scFv, see Pluckthun "The Pharmacology of Monoclonal Antibodies" Vol. 113, eds. Rosenburg and Moore, Springer Verlag, New York (1994) pp. 269-315).

The sc(Fv)2s of the present invention include antibodies in which two VHs and two VLs are arranged in the order of, VH, VL, VH, and VL ([VH] linker [VL] linker [(VH)] linker [VL]), starting from the N terminus of a single-chain polypeptide. However, the order of the two VHs and two VLs is not limited to the above arrangement, and may be arranged in any order. Examples of arrangements are listed below:
[VL] linker [VH] linker [VH] linker [VL]
[VH] linker [VL] linker [VL] linker [VH]
[VH] linker [VL] linker [VL] linker [VL]
[VL] linker [VL] linker [VH] linker [VH]
[VL] linker [VH] linker [VL] linker [VH]

The sc(Fv)2s of the present invention may also comprise amino acid sequences in addition to those of the antibody variable regions and linkers.

The variable regions of the antibody used in the present invention may be the entire variable region, or partial sequences of the variable region, as long as they retain antigen-binding activity. Furthermore, the amino acid sequences in the variable regions may be substituted, deleted, added, inserted, and such. For example, the variable regions may be chimerized or humanized to reduce antigenicity.

Other proteins, such as an Fc domain of an IgG, may be fused with the N or C terminus of the sc(Fv)2 of the present invention (Clinical Cancer Research (2004)10, 1274-1281). Such proteins to be fused can be suitably selected by those skilled in the art. The sc(Fv)2 of the present invention may be in the form of (sc(Fv)2-Fc in which two units of scFv are linked to the N terminus of each hinge of Fc and the antibody Fc region is used as the middle linker (linker 2) (J Immunol Methods (2005) 306(1-2):93-103).

The sc(Fv)2s of the present invention may be conjugated with carrier polymers, such as PEGs, or organic compounds, such as anticancer agents. Alternatively, sugar chains can be added by inserting a glycosylation sequence.

The linkers for linking the variable regions of an antibody can be arbitrary peptide linkers that can be introduced by genetic engineering, or synthetic linkers (for example, see Protein Engineering (1996) 9(3), 299-305); however, peptide linkers are preferred in the present invention. The length of the peptide linkers can be suitably selected by those skilled in the art, depending on the purpose, and is preferably five amino acids or more (the upper limit is not particularly limited; however, the length is typically 30 amino acids or less, preferably 20 amino acids or less), and more preferably 15 amino acids. When an sc(Fv)2 comprises three peptide linkers, the lengths of the peptide linkers may all be the same or different.

For example, such peptide linkers include:

```
Ser

Gly-Ser

Gly-Gly-Ser

Ser-Gly-Gly

Gly-Gly-Gly-Ser              (SEQ ID NO: 9)

Ser-Gly-Gly-Gly              (SEQ ID NO: 10)

Gly-Gly-Gly-Gly-Ser          (SEQ ID NO: 11)

Ser-Gly-Gly-Gly-Gly          (SEQ ID NO: 12)

Gly-Gly-Gly-Gly-Gly-Ser      (SEQ ID NO: 13)

Ser-Gly-Gly-Gly-Gly-Gly      (SEQ ID NO: 14)

Gly-Gly-Gly-Gly-Gly-Gly-Ser  (SEQ ID NO: 15)

Ser-Gly-Gly-Gly-Gly-Gly-Gly  (SEQ ID NO: 16)

(Gly-Gly-Gly-Gly-Ser (SEQ ID NO: 11))n (Ser-Gly-Gly-Gly-Gly (SEQ ID NO: 12))n
``` where n is an integer of one or more. The lengths and sequences of the peptide linkers can be suitably selected by those skilled in the art, depending on the purpose.

Synthetic linkers (chemical crosslinking agents) include crosslinking agents routinely used to crosslink peptides, for example, N-hydroxy succinimide (NHS), disuccinimidyl suberate (DSS), bis(succinimidyl) suberate (BS3), dithiobis (succinimidyl propionate) (DSP), dithiobis(succinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSOCOES), and bis[2-(succinimidoxycarbonyloxy)ethyl]sulfone (sulfo-BSOCOES). These crosslinking agents are commercially available.

In general, three linkers are required to link four antibody variable regions together. The linkers to be used may all be the same or different.

Herein, the sc(Fv)2 compositions refer to compositions comprising one or more structural isomers of sc(Fv)2.

sc(Fv)2 compositions can be prepared by methods known to those skilled in the art. For example, the sc(Fv)2 compositions can be prepared by introducing into a host cell a vector comprising DNA encoding sc(Fv)2 as a insert, expressing sc(Fv)2, and collecting the expression products.

The vectors are not particularly limited, and any vector can be used so long as it can stably carry the insert DNA. For example, when *Escherichia coli* (*E. coli*) is used as the host, various commercially available vectors may be used; however, preferred cloning vectors are pBluescript vector (Stratagene). When using vectors for the purpose of producing the sc(Fv)2 of the present invention, expression vectors are particularly useful. The expression vectors are not particularly limited so long as the vectors expresses the sc(Fv)2 in vitro, in *E. coli*, in culture cells, or in a body of an organism. For example, pBEST vector (Promega) is preferred for in vitro expression; pET vector (Invitrogen), for *E. coli*; pME18S-FL3 vector (GenBank Accession No. AB009864), for culture cells; and pME18S vector (Mol Cell Biol. 8:466-472 (1988)), for organisms. DNAs of the present invention can be inserted into the vectors by conventional methods, for example, by ligation using restriction sites (Current protocols in Molecular Biology, eds. Ausubel et al. 1987) Publish. John Wiley & Sons, Section 11.4-11.11).

The host cells described above are not particularly limited, and depending on the purpose, various host cells can be used. Cells for expressing sc(Fv)2 include, for example, bacterial cells (for example, *Streptococcus, Staphylococcus, E. coli, Streptomyces*, and *Bacillus subtilis*); fungal cells (for example, yeast and *Aspergillus*); insect cells (for example, *Drosophila* S2 and *Spodoptera* SF9); animal cells (for example, CHO, COS, HeLa, C127, 3T3, BHK, HEK293, and Bowes melanoma cell); and plant cells. The vectors can be introduced into host cells by known methods, for example, calcium-phosphate precipitation method, electroporation (Current protocols in Molecular Biology, eds. Ausubel et al. (1987) Publish. John Wiley & Sons, Section 9.1-9.9), lipofectamine method (GIBCO-BRL), and microinjection method.

When the sc(Fv)2 of the present invention is secreted into the culture media, the sc(Fv)2 compositions can be collected by collecting the culture media. Alternatively, when the scFv)2 is produced within cells, the cells are first lysed and then the sc(Fv)2 compositions are collected.

The sc(Fv)2 compositions of the present invention may be in any state, so long as they comprise one or more structural isomers of sc(Fv)2. The compositions include, for example, crude compositions such as recombinant cell cultures, and compositions in a purified state, but are not limited thereto.

In the present invention, structural isomers refer to proteins whose amino acid sequences are identical but the conformations (secondary or tertiary structures) are different from each other. In general, structural isomers are different in at least one of chemical, biological, or physical properties.

The structural isomers of sc(Fv)2 include, for example, structural isomers of single chain diabody type and bivalent scFv type.

Herein the single chain diabody type refers to sc(Fv)2 having a structure in which variable regions 1 and 4 are associated together, and variable regions 2 and 3 are associated together, when the sc(Fv)2 are in the following arrangement: [variable region 1] (linker 1)[variable region 2] (linker 2)[variable region 3] (linker 3)[variable region 4].

Herein, the bivalent scFv type refers to sc(Fv)2 having a structure in which variable regions 1 and 2 are associated together and variable regions 3 and 4 are associated together.

The single chain diabody type and bivalent scFv type include, for example, sc(Fv)2 having the structure shown in FIG. 1b. Whether a structural isomer of sc(Fv)2 has a single chain diabody type structure or bivalent scFv type structure can be determined by the methods for identifying structural isomers as described below. Alternatively, such an identification can be carried out by NMR analysis, crystal structure analysis, or such.

The structural isomers can be separated and obtained (purified) from sc(Fv)2 compositions, for example, by loading the sc(Fv)2 compositions onto an ion exchange or hydroxyapatite column and obtaining or removing specific structural isomers, but are not limited to these methods. The purification can also be carried out by methods known to those skilled in the art, such as various chromatographic columns, filtration, ultrafiltration, salting precipitation, solvent precipitation, solvent extraction, distillation, immunoprecipitation, SDS-polyacrylamide gel electrophoresis, isoelectric focusing, capillary isoelectric focusing, dialysis, and recrystallization.

Chromatographies include, for example, ion exchange chromatographies, adsorption chromatographies, isoelectric focusing, gel filtrations, reverse-phase chromatographies, and hydrophobic chromatographies (Strategies for Protein Purification and Characterization: A Laboratory Course Manual. Ed Daniel R. Marshak et al., Cold Spring Harbor Laboratory Press, 1996). Chromatographies can be carried out by using liquid phase chromatographies such as HPLC and FPLC.

When ion exchange chromatographies are used, the types of ion exchange columns to be used are not particularly limited. Both cation exchange columns and anion exchange columns may be used, and such columns can be suitably determined depending on the target antibody, structural isomer, or such. For example, SP ion exchange columns, Q ion exchange columns, and the like can be used, but are not limited thereto. Adsorption chromatographies include, for example, hydroxyapatite chromatography, but are not limited thereto.

Based on the present invention, purified samples of specific structural isomers can also be obtained using these purification methods.

The production methods of the pharmaceutical compositions of the present invention compares the activity between the structural isomers of sc(Fv)2 and pre-determines the structural isomer with a higher activity, when the structural isomers in sc(Fv)2 compositions are different in their activities. Thus they allow the separation and acquisition of a structural isomer with higher activity from structural isomers in sc(Fv)2 compositions. Furthermore, the production methods of the pharmaceutical compositions of the present invention enable the preparation of compositions of sc(Fv)2 having predetermined linker lengths, in which the linker lengths are determined to obtain a preferred ratio of structural isomers in the sc(Fv)2 compositions using the method described below, before separating the structural isomers from the sc(Fv)2 compositions. Alternatively, sc(Fv)2 compositions can also be prepared by the following steps: preparing multiple sc(Fv)2 compositions with varying linker lengths before separating the structural isomers from the sc(Fv)2 compositions; analyzing the ratio of the structural isomers by the methods of analyzing the ratio of structural isomers described below; selecting sc(Fv)2 having linkers that give a preferred ratio of structural isomers in sc(Fv)2 compositions, and preparing sc(Fv)2 compositions from the selected sc(Fv)2. Alternatively, sc(Fv)2 compositions can also be prepared from the selected sc(Fv)2 by modifying amino acid residues which form the contact surface of VH and VL, using the method described below.

Herein, the structural isomer with higher activity refers to structural isomers which have a high activity, preferably having the highest activity, when the structural isomers differ in their activities. For example, when two types of structural isomers exist, the structural isomer having higher activity is the present invention's structural isomer with higher activity.

Structural isomers with higher activity can be determined by methods known to those skilled in the art. The structural isomers with higher activity can be determined, for example, by isolating each structural isomer and by measuring their activities of interest under the same conditions.

The activity of the present invention may be any activity, such as binding activity, neutralizing activity, cytotoxic activity, agonistic activity, antagonistic activity, and enzymatic activity. The activity is not particularly limited; however, the activity is preferably an activity that quantitatively and/or qualitatively alters or influences living bodies, tissues, cells, proteins, DNAs, RNAs, and such., Agonistic activities are especially preferred.

"Agonistic activity" refers to an activity that induces a change in some physiological activity by transducing a signal into cells and such, due to the binding of an antibody to an antigen such as a receptor. Physiological activities include, but are not limited to, for example, proliferation activity, survival activity, differentiation activity, transcriptional activity, membrane transportation activity, binding activity, proteolytic activity, phosphorylation/dephosphorylation activity, oxidation/reduction activity, transfer activity, nucleolytic activity, dehydration activity, cell death-inducing activity, and apoptosis-inducing activity.

The antigens of the present invention are not particularly limited, and any antigen may be used. Examples of antigens include, receptors, tumor antigens, MHC antigens, and differentiation antigens. Examples of receptors include receptors belonging to receptor families such as the hematopoietic growth factor receptor family, the cytokine receptor family, the tyrosine kinase receptor family, the serine/threonine kinase receptor family, the TNF receptor family, the G protein-coupled receptor family, the GPI-anchored receptor family, the tyrosine phosphatase receptor family, the adhesion factor family, and the hormone receptor family. There are many documents that describe receptors belonging to these receptor families, and their characterstics, which include for example, Cooke B A, King R J B, van der Molen H J Eds. New Comprehensive Biochemistry Vol. 18B "Hormones and their Actions Part II" pp. 1-46 (1988) Elsevier Science Publishers BV, New York, USA; Patthy L. (1990) Cell, 61: 13-14; Ulrich A. et al. (1990) Cell, 61: 203-212; Massagul J. (1992) Cell, 69: 1067-1070; Miyajima A. et al. (1992) Annu, Rev. Immunol., 10: 295-331; Taga T. and Kishimoto T. (1992) FASEB J., 7: 3387-3396; Fantl W I. et al. (1993) Annu. Rev. Biochem., 62: 453-481; Smith C A., et al. (1994) Cell, 76: 959-962; Flower D R. (1999) Biochim. Biophys. Acta, 1422: 207-234; SAIBO KOGAKU (Cell Technology) Supplementary vol. Handbook series "Handbook for Adhesion factors" M. Miyasaka Ed. (1994) Shujunnsha, Tokyo, Japan, and so on.

Specific receptors belonging to the receptor families listed above include: human or mouse erythropoietin (EPO) receptor, human or mouse granulocyte-colony stimulating factor (G-CSF) receptor, human or mouse thrombopoietin (TPO) receptor, human or mouse insulin receptor, human or mouse Flt-3 ligand receptor, human or mouse platelet-derived growth factor (PDGF) receptor, human or mouse interferon (IFN)-α and -β receptor, human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, and human or mouse ciliary neurotrophic factor (CNTF) receptor (hEPOR: Simon, S. et al. (1990) Blood 76, 31-35; mEPOR: D'Andrea, A D. et al. (1989) Cell 57, 277-285; hG-CSFR: Fukunaga, R. et al. (1990) Proc. Natl. Acad. Sci. USA. 87, 8702-8706; mG-CSFR: Fukanaga, R. et al. (1990) Cell 61, 341-350; hTPOR: Vigon, I. et al. (1992) 89, 5640-5644; mTPOR: Skoda, R C. et al. (1993) 12, 2645-2653; hInsR: Ulrich, A, et al. (1985) Nature 313, 756-761; hFlt-3: Small, D. et al. (1994) Proc. Natl. Acad. Sci. USA. 91, 459-463; hPDGFR: Gronwald, R G K. et al. (1988) Proc. Natl. Acad. Sci. USA.

85, 3435-3439; hIFN α/β R: Uze, G. et al. (1990) Cell 60, 225-234, and Novick, D. et al. (1994) Cell 77, 391-400).

Tumor antigens, which are also called tumor-specific antigens, are expressed along with malignant transformation of cells. Furthermore, abnormal sugar chains displayed on cellular surface or protein molecules upon canceration of cells also serve as tumor antigens, and are called tumor-associated carbohydrate antigens in particular. Tumor antigens include, for example, CA19-9, CA15-3, sialyl SSEA-1 (SLX) and the like.

MHC antigens are broadly grouped under MHC class I and N antigens. MHC class I antigens include HLA-A, -B, -C, -E, -F, -G, and -H, while MHC class II antigens include HLA-DR, -DQ, and -DP.

Differentiation antigens include CD1, CD2, CD3, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130 and such.

There is no limitation as to the type of detection indicators to be used for determining the change in activity, as long as the indicator can monitor quantitative and/or qualitative changes. For example, it is possible to use cell-free assay indicators, cell-based assay indicators, tissue-based assay indicators, and in biological indicators.

Indicators that can be used in cell-free assays include enzymatic reactions, quantitative and/or qualitative changes in proteins, DNAs, or RNAs. Such enzymatic reactions include, for example, amino acid transfers, sugar transfers, dehydrations, dehydrogenations, and substrate cleavages. Alternatively, protein phosphorylations, dephosphorylations, dimerizations, multimerizations, hydrolyses, dissociations and such; DNA or RNA amplifications, cleavages, and extensions can be used as the indicator in cell-free assays. For example, protein phosphorylations downstream of a signal transduction pathway may be used as a detection indicator.

Alterations in cell phenotype, for example, quantitative and/or qualitative alterations in products, alterations in growth activity, alterations in cell number, morphological alterations, or alterations in cellular properties, can be used as indicators in cell-based assays. The products include, for example, secretory proteins, surface antigens, intracellular proteins, and miRNAs. The morphological alterations include, for example, alterations in dendrite formation and/or dendrite number, alteration in cell flatness, alteration in cell elongation/axial ratio, alterations in cell size, alterations in intracellular structure, heterogeneity/homogeneity of cell populations, and alterations in cell density. Such morphological alterations can be observed under a microscope. Cellular properties to be used as the indicator include anchor dependency, cytokine-dependent response, hormone dependency, drug resistance, cell motility, cell migration activity, pulsatory activity, and alteration in intracellular substances. Cell motility includes cell infiltration activity and cell migration activity. The alterations in intracellular substances include, for example, alterations in enzyme activity, mRNA levels, levels of intracellular signaling molecules such as Ca2+ and cAMP, and intracellular protein levels. When a cell membrane receptor is used, alterations in the cell proliferating activity induced by receptor stimulation can be used as the indicator.

Indicators to be used in tissue-based assays include functional alterations adequate for the subject tissue.

Alterations in tissue weight, alterations in the blood system (for example, alterations in blood cell counts, protein contents, or enzyme activities), alterations in electrolyte levels, and alterations in the circulating system (for example, alterations in blood pressure or heart rate) can be used as biological indicators.

The methods for measuring such detection indices are not particularly limited. For example, absorbance, luminescence, color development, fluorescence, radioactivity, fluorescence polarization, surface plasmon resonance signal, time-resolved fluorescence, mass, absorption spectrum, light scattering, and fluorescence resonance energy transfer may be used. These measurement methods are known to those skilled in the art and may be selected appropriately depending on the purpose.

For example, absorption spectra can be obtained by using a conventional photometer, plate reader, or such; luminescence can be measured with a luminometer or such; and fluorescence can be measured with a fluorometer or such. Mass can be determined with a mass spectrometer Radioactivity can be determined with a device such as a gamma counter depending on the type of radiation. Fluorescence polarization can be measured with BEACON (TaKaRa). Surface plasmon resonance signals can be obtained with BIACORE. Time-resolved fluorescence, fluorescence resonance energy transfer, or such can be measured with ARVO or such. Furthermore, a flow cytometer can also be used for measuring. It is possible to use one of the above methods to measure two or more different types of detection indices. A greater number of detection indices may also be examined by using two or more measurement methods simultaneously and/or consecutively. For example, fluorescence and fluorescence resonance energy transfer can be measured at the same time with a fluorometer.

In the present invention, agonistic activities can be assayed by methods known to those skilled in the art. For example, agonistic activities can be determined by methods using cell growth as an indicator, as described in the Examples. More specifically, an antibody whose agonistic activity is to be determined is added to cells which proliferate in an agonist-dependent manner, followed by incubation of the cells. Then, a reagent such as WST-8 which shows a coloring reaction at specific wavelengths depending on the viable cell count, is added to the culture and the absorbance is measured. Subsequently, the agonistic activity can be determined using the obtained absorbance as an indicator Cells that proliferate in an agonist-dependent manner can also be prepared by methods known to those skilled in the art. For example, when the antigen is a receptor capable of transducing cell growth signals, cells expressing the receptor may be used. Alternatively, when the antigen is a receptor that cannot transduce signals, a chimeric receptor consisting of the intracellular domain of a receptor that transduces cell growth signals and the extracellular domain of a receptor that does not transduce cell growth signals can be prepared for cellular expression. Receptors that transduce cell growth signals include, for example, G-CSF receptors, mpl, neu, GM-CSF receptors, EPO receptors, c-kit, and FLT-3. Cells that can be used to express a receptor include, for example, BaF3, NFS60, FDCP-1, FDCP-2, CTLL-2, DA-1, and KT-3.

Herein, pharmaceutical sc(Fv)2 compositions refer to sc(Fv)2 compositions aimed at administration to humans for treating or preventing diseases.

Specific structural isomers of sc(Fv)2 separated and obtained by the methods of the present invention or sc(Fv)2 compositions with an increased portion of specific structural isomers as described in the methods below can be mixed with pharmaceutically acceptable carriers or solvents that are inactive to the sc(Fv)2 to prepare pharmaceutical compositions. Specifically, the present invention also provides pharmaceutical compositions that comprise as an active ingredient a structural isomer of sc(Fv)2 separated and obtained by the methods described above or a sc(Fv)2 composition with an increased portion of a specific structural isomer.

Such pharmaceutically acceptable carriers and solvents include, for example, sterilized water, physiological saline, stabilizers, vehicles, antioxidants (ascorbic acid and such), buffers (phosphate, citrate, and other organic acids and such), preservatives, detergents (PEG and Tween and the like), chelating agents (EDTA and the like), and binders and the like. Alternatively, the pharmaceutically acceptable carries and solvents may comprise other low molecular weight antibody polypeptides; proteins, such as serum albumin, gelatin, and immunoglobulins; amino acids, such as glycine, glutamine, asparagine, arginine, and lysine; carbohydrates and sugars, such as polysaccharides and monosaccharides; and sugar alcohols, such as mannitol and sorbitol. When prepared as aqueous solutions for injection, the compositions can comprise, for example, physiological saline, an isotonic solution comprising glucose and other adjuvants, including, for example, D-sorbitol, D-mannose, D-mannitol, and sodium chloride, which can also be used in combination with an appropriate solubilizing agent, for example, alcohol (such as ethanol), polyalcohol (propylene glycol and PEG and such), and non-ionic detergent polysorbate 80 and HCO-50 and such).

If required, the agents may be encapsulated in microcapsules (microcapsules of hydroxymethylcellulose, gelatin, poly[methylmethacrylic acid] or such) or prepared as colloidal drug delivery systems (liposome, albumin microspheres, microemulsion, nano-particles, nano-capsules, and such) (see "Remington's Pharmaceutical Science 16th edition", Oslo Ed., 1980, and the like). Furthermore, methods for making agents into sustained-release agents are also known, and are applicable to the present invention (Langer et al., J. Biomed. Mater. Res. 1981, 15: 167-277; Langer, Chem, Tech, 1982, 12: 98-105; U.S. Pat. No. 3,773,919; European Patent Application No. (EP) 58,481; Sidman et al., Biopolymers 1983, 22: 547-556; and EP 133,988).

The sc(Fv)2 pharmaceutical compositions of the present invention can be prepared by methods known to those skilled in the art and are not limited to the methods described above.

Administration to patients may be performed either orally or parenterally, but preferably is performed parenterally. Specific examples include injections, nasal formulations, pulmonary formulations, and cutaneous formulations. For example, injections can be administered systemically or locally by intravenous injection, intramuscular injection, intraperitoneal injection, or subcutaneous injection. Furthermore, methods for administration can be suitably selected according to the age and symptoms of the patient. Dose to be given for example, can be selected from within the range of 0.0001 mg to 1,000 mg per kg of body weight for a single dose. Alternatively, the dose can be selected from within the range of 0.001 to 100,000 mg/body for each patient. However, the dose of an antibody of the present invention is not limited to these examples.

The present invention provides sc(Fv)2 compositions in which the content ratio of a specific structural isomer is 80% or greater, preferably 90% or greater, and more preferably 95% or greater. More specifically, sc(Fv)2 compositions in which the content ratio of single chain diabody type is 80% or greater, preferably 90% or greater; and more preferably 95% or greater, or sc(Fv)2 compositions in which the content ratio of bivalent scFv type is 80% or greater, preferably 90% or greater, and more preferably 95% or greater can be exemplified.

Herein, "the content ratio of a specific structural isomer is 80%" means that the proportion of a specific structural isomer to the total structural isomers in the sc(Fv)2 composition is 80%. For example, when an sc(Fv)2 composition comprises two types of structural isomers, single chain diabody type and bivalent scFv type, "the content ratio of the single chain diabody type is 80%" means that the ratio of the single chain diabody type and bivalent scFv type is 80:20.

In the present invention, the upper limit of the content ratio of 80% or greater, 90% or greater, or 95% or greater is not particularly limited; however, the limit is preferably 100% or close to 100%. The upper limit that is close to 100% includes, for example, 99.999%, 99.99%, 99.9%, 99%, or such, varying depending on the purification and/or analytical techniques of those skilled in the art. The content ratio of a structural isomer can be determined, for example, by separating the structural isomers using ion exchange chromatography, isoelectric focusing, capillary isoelectric focusing, and the like.

The present invention also provides pharmaceutical compositions comprising as an active ingredient an sc(Fv)2 composition in which the content ratio of a specific structural isomer is 80% or greater. When sc(Fv)2 is used as a pharmaceutical composition, in general, higher activities are preferred. Thus, the composition preferably comprises as an active ingredient an sc(Fv)2 composition in which the content ratio of a structural isomer with higher activity is 80% or greater. For example, the agonistic activity of an anti-Mpl antibody is higher when the antibody is in the form of a single chain diabody. Therefore, when sc(Fv)2 is used against Mpl as an agonist, such pharmaceutical compositions preferably comprises as an active ingredient an sc(Fv)2 composition in which the content ratio of single chain diabody type is 80% or greater.

The present invention provides methods for controlling the activity of sc(Fv)2 compositions, which comprise the steps of modifying the proportion of structural isomers in the sc(Fv)2 compositions.

Based on the finding that there are significant differences between the activities of structural isomers of sc(Fv)2, the present invention has discovered that the activity of sc(Fv)2 compositions can be controlled by altering the content ratio of a specific structural isomer in the sc(Fv)2 compositions. Specific methods for controlling the activity of sc(Fv)2 compositions include, for example, altering the ratio between the single chain diabody type and bivalent scFv type in the sc(Fv)2 compositions. The activity of sc(Fv)2 compositions can thus be controlled by this method.

The present invention also provides methods for increasing the activity of sc(v)2 compositions, which comprise increasing the proportion of a specific structural isomer in the sc(Fv)2 compositions. This can be performed by the above-described methods for separating and obtaining specific structural isomers from the sc(Fv)2 compositions.

For example, highly active sc(Fv)2 compositions can be produced by increasing the proportion of a structural isomer with higher activity in sc(Fv)2 compositions. In contrast, sc(Fv)2 compositions with a repressed activity can be produced by reducing the proportion of the structural isomer with higher activity in the sc(Fv)2 compositions.

When the activity of the single chain diabody type is higher than that of the bivalent scFv type, the activity of sc(Fv)2 compositions can be increased by increasing the content ratio of the single chain diabody type in sc(Fv)2 compositions, or the activity of sc(Fv)2 compositions can be reduced by increasing the content ratio of the bivalent scFv type. In contrast, when the activity of the bivalent scFv type is higher than that of the single chain diabody type, the activity of sc(Fv)2 compositions can be increased by increasing the content ratio of the bivalent scFv type in sc(Fv)2 compositions, or the activity of sc(Fv)2 compositions can be reduced by increasing the content ratio of the single chain diabody type. Whether the single chain diabody has the higher activity or whether the bivalent scFv has the higher activity depends on the type of activity of interest; however, the activity can be readily determined by methods known to those skilled in the art.

When sc(Fv)2s are used as pharmaceutical compositions, higher activities are often more preferred in general. Accordingly, the activity of pharmaceutical compositions can be increased by altering the content of a specific structural isomer in sc(Fv)2 compositions.

The method for increasing the activity of sc(Fv)2 compositions by increasing the content ratio of a specific structural isomer contained in the sc(Fv)2 compositions can be any method. For example, the content ratio of a specific structural isomer may be increased after obtaining the sc(Fv)2 composition or alternatively, DNA encoding sc(Fv)2 may be designed so that the content ratio of a specific structural isomer would be increased.

Specific methods for increasing the proportion of a specific structural isomer after obtaining sc(Fv)2 compositions include, for example, methods that isolate the target structural isomer from the obtained sc(Fv)2 compositions (or removing structural isomers other than the target structural isomer). Such an isolation of the target structural isomers can be performed by the above-described protein separation and acquisition methods known to those skilled in the art.

Furthermore, the content ratio of a specific structural isomer can also be increased, for example, by heating sc(Fv)2 compositions. The present inventors discovered that the content ratio of the single chain diabody type could be increased by incubating sc(Fv)2 compositions at a constant temperature. Thus, the content ratio of the single chain diabody type can be increased by incubating sc(Fv)2 compositions at 15 to 50° C., preferably at 20 to 40° C., more preferably at 25 to 35° C. The increased content ratio of the single chain diabody type would be maintained even when the incubated sc(Fv)2 compositions are returned to the original temperature.

Methods for designing DNA encoding sc(Fv)2 to increase the content ratio of a specific structural isomer include, for example, the above described methods for designing DNA such that the linker is of appropriate length.

Furthermore, the content ratio of a specific structural isomer in sc(Fv)2 compositions can be increased by controlling the association of the variable regions of sc(Fv)2. Specifically, DNA encoding sc(Fv)2 is modified so that amino acid residues which form the contact surface of the sc(Fv)2 variable regions are modified.

Herein, "association" may in other words refer to the state of interaction between the variable regions of the sc(Fv)2, for example.

Herein, "controlling the association" means controlling to achieve a desired state of association, more specifically controlling to prevent an unfavorable association formed in the sc(Fv)2.

Herein, "contact surface" generally refers to the association surface when the association (interaction) takes place. Amino acid residues that form the contact surface generally refer to one or more amino acid residues in the variable regions of sc(Fv) 2, which participate in the association, and more preferably refer to amino acid residues that come close together and are involved in the interaction when association takes place. Specifically, such interactions include hydrogen bonding, electrostatic interaction, and salt bridging of amino acid residues that come close together upon association.

Herein, the "amino acid residues that form the contact surface" specifically describes the amino acid residues in the variable regions of sc(Fv)2 that constitute the contact surface.

Specifically, the "modification" of amino acid residues in the methods of the present invention refers to substituting the original amino acid residues (before modification) with other amino acid residues, deleting the original amino acid residues, or newly adding some amino acid residues, but preferably refers to substituting other amino acid residues for the original amino acid residues.

"Modifying the DNA" in the above-described methods of the present invention means to modify a DNA so that it corresponds to the amino acid residues to be introduced by the "modification" of the present invention. More specifically, "Modifying the DNA" means that a DNA encoding the original amino acid residues is modified to a DNA encoding the amino acid residues with a modification introduced. This generally implies inserting, deleting, or substituting at least one nucleotide of the original DNA by gene manipulation or mutagenesis, to create a codon that encodes the target amino acid residue. Specifically, the codon encoding the original amino acid residue is replaced with a codon encoding an amino acid residue introduced by modification. Such a DNA modification can be suitably carried out by techniques known to those skilled in the art for example, the site-directed mutagenesis method, or PCR mutagenesis method.

In a preferred embodiment of the present invention, for example, mutations are introduced at amino acid residues on the contact surface so that the charges of two or more amino acid residues forming the contact surface in the variable regions of sc(Fv)2 are of the same kind. As a result of such modification of two or more amino acid residues involved in the association on the contact surface to have the same kind of charge, the association of the amino acid residues are inhibited by the repulsive force between the charges. Thus, such amino acid residues to be modified by the methods described above are preferably two or more amino acid residues that come close to each other upon association of the variable regions of sc(Fv)2 to form the contact surface.

The amino acid residues that come close together upon association can be found, for example, by analyzing the tertiary structure of sc(Fv)2 and examining the amino acid sequences of the variable regions that form the contact surface upon association of the sc(Fv)2. Such amino acid residues that come close together at the contact surface are preferred targets for "modification" by the methods of the present invention.

Some amino acids are known to be charged. Generally known amino acids with a positive charge (positively-charged amino acids) include lysine (K), arginine (R), and histidine (H). Known amino acids with a negative charge (negatively charged amino acids) include aspartic acid (D)

and glutamic acid (E) and such. Thus, in the present invention, "amino acid residues with the same kind of charge" preferably means amino acid residues with a positive charge, or those with a negative charge.

In the present invention, amino acid residues that form the contact surface are preferably modified to have the same kind of charge. Identical amino acids are more preferred among amino acid residues with the same kind of charge. For example, amino acid residues after modification may be lysine and arginine, more preferably the residues are two lysines or two arginines.

When multiple amino acid residues are introduced by modification, the amino acid residues may include a few non-charged amino acid residues.

There is no limitation as to the number of amino acid residues to be modified by the methods of the present invention. However, to avoid the reduction of binding activity to the antigen, preferably the number of amino acid residues modified is as few as possible. The above-mentioned "few" means, for example, about 1 to 10, preferably about 1 to 5, more preferably about 1 to 3, and still more preferably 1 or 2.

In a preferred embodiment of the present invention, when an amino acid residue (X) that forms the contact surface in the original sc(Fv)2 is already a charged amino acid, or forms a hydrogen bond, an amino acid residue that comes close to amino acid residue (X) at association, and which corresponds to the amino acid residue (X) at association, is modified to an amino acid residue identical to amino acid residue (X) (or a amino acid residue with the same kind of charge as that of amino acid residue (X). In this embodiment, one of the amino acid residues that form the contact surface may be modified.

In another preferred embodiment of the present invention, mutations are introduced at amino acid residues on the contact surface so that the modification of amino acid residues forming the contact surface of the variable regions in sc(Fv)2 allows the amino acid residues forming the hydrophobic core on the contact surface to become charged amino acid residues.

In general, "hydrophobic core" refers to a part formed as a result of hydrophobic amino acid side chains assembling to the inner side of associated polypeptides. Hydrophobic amino acids include, for example, alanine, isoleucine, leucine, methionine, phenylalanine, proline, tryptophan, and valine and such. In addition, amino acid residues other than the hydrophobic amino acid residues (for example, tyrosine) may be involved in the formation of the hydrophobic core. Together with the hydrophilic surface in which side chains of hydrophilic amino acids are exposed outside, the hydrophobic core can be a driving force to promote association of water-soluble polypeptides. When hydrophobic amino acids of two different domains are at the molecule surface and are exposed to water molecules, the entropy is increased, resulting in increase of free energy. Accordingly, the two domains associate with each other to decrease the free energy for stabilization, and thus hydrophobic amino acids on the contact surface are buried inside the molecule, forming the hydrophobic core.

When amino acid residues forming the hydrophobic core which was formed by the association of polypeptides are modified to charged polar amino acids, the hydrophobic core formation would be inhibited, resulting in the inhibition of the polypeptide association. Similarly in sc(Fv)2, which is a polypeptide, the hydrophobic core is formed upon association of the variable regions. Thus, the association of the variable regions can be controlled by replacing these amino acid residues in the hydrophobic core with charged amino acids.

By analyzing the desired sc(Fv)2 amino acid sequence, those skilled in the art can find out whether a hydrophobic core exists, where the core is formed (regions), and so on.

Furthermore, knobs-into-holes technology can be used (Japanese Patent Kohyo Publication No, (JP-A) 2001-523971 (unexamined Japanese national phase publication corresponding to a non-Japanese international publication)) to promote a desirable association of amino acid residues that form the contact surface of the variable regions. The knobs-into-holes method is a method applicable to the present invention for introducing a specific and complementary interaction between the contact surfaces of the first and second polypeptides, which promotes heteromultimer formation and suppresses homomultimer formation (for example, introducing a residue containing a free thiol into both the first and second polypeptides at positions corresponding to the contact surfaces, so that a non-natural disulfide bond is formed between the first and second polypeptides). Knobs-into-holes is an already known technique to those skilled in the art. Those skilled in the art can suitably apply such a method to sc(Fv)2s In addition, the above-described methods can also be used in combination.

In general, three CDRs and four FR regions constitute the variable region. In a preferred embodiment of the present invention, amino acid residues to be "modified" can be suitably selected, for example, from amino acid residues in the CDRs or FR region. In general, modification of amino acid residues in the CDRs may sometimes result in reduction of the binding activity to antigens. Thus, although such amino acid residues to be "modified" are not particularly limited, it is preferable that they be suitably selected from the amino acid residues in the FR region.

With respect to the desired sc(Fv)2 the association of which is to be controlled by the methods of the present invention, those skilled in the art can suitably know the types of amino acid residues that come close together on the contact surface of FR upon association.

Such amino acid residues that come close together on the contact surface of FR upon association include, for example, glutamine (Q) at position 39 (FR2 region) in VH and glutamine (Q) at position 38 (FR2 region) in VL facing (contacting) each other. Another preferred example include leucine O) at position 45 (FE) in VH and proline (P) at position 44 (FR2) in VL facing (contacting) each other. The numbering for these sites is based on the methods of Kabat et al. (Kabat E A et al. 1991. Sequence of Proteins of Immunological Interest. NIH).

These amino acid residues are known to be highly conserved between human and mouse (J, Mol. Recognit. (2003) 16: 113-120). Thus, the association of variable regions of sc(Fv)2s other than the ones described in the Examples can also be controlled by modifying the amino acid residues corresponding to the amino acid residues listed above.

Example of methods for increasing the content ratio of the single chain diabody type in an sc(Fv)2 having the arrangement of [variable region 1] (linker 1)[variable region 2] (linker 2)[variable region 3] (linker 3)[variable region 4] are described below.

When bivalent scFv type occurs in the sc(Fv)2, substitution mutations are introduced at the amino acid residues which form the contact surfaces of the variable regions to suppress the association between variable regions 1 and 2, and between variable regions 3 and 4, but not to suppress (to enhance) the association between variable regions 1 and 4, and between variable region 2 and 3.

When structural isomers having a structure where variable regions 1 and 3 are associated and variable regions 2 and 4 are associated occur in the sc(Fv)2, substitution mutations are introduced at the amino acid residues that form the contact surfaces of the variable regions to suppress the association described above but not to suppress (to enhance) the association between variable regions 1 and 4, and the association between variable regions 2 and 3.

When structural isomers having a structure where variable regions 1 and 3 are associated occur in the sc(Fv)2, substitution mutations are introduced at the amino acid residues that form the contact surfaces of the variable regions to suppress the association described above but not to suppress (to enhance) the association between variable regions 1 and 4, and between variable regions 2 and 3.

When structural isomers having a structure where variable regions 2 and 4 are associated occur in the sc(Fv)2, substitution mutations are introduced at the amino acid residues that form the contact surfaces of the variable regions to suppress the association described above but not to suppress (to enhance) the association between variable regions 1 and 4, and between variable regions 2 and 3.

Alternatively, examples of methods for increasing the content ratio of the bivalent scFv type is described below in an sc(Fv)2 having the arrangement of [variable region 1] (linker 1)[variable region 2] (linker 2)[variable region 3] (linker 3)[variable region 4].

When the single chain diabody type occurs in the sc(Fv)2, substitution mutations are introduced at the amino acid residues that form the contact surfaces of the variable regions to suppress association between variable regions 1 and 4, and between variable regions 2 and 3, but not to suppress (to enhance) the association between variable regions 1 and 2, and between variable region 3 and 4.

When structural isomers having a structure where variable regions 1 and 3 are associated and variable regions 2 and 4 are associated occur in the sc(Fv)2, substitution mutations are introduced at the amino acid residues that form the contact surfaces of the variable regions to suppress the association described above but not to suppress (to enhance) the association between variable regions 1 and 2, and the association between variable regions 3 and 4.

When structural isomers having a structure where variable regions 1 and 3 are associated occur in the sc(Fv)2, substitution mutations are introduced at the amino acid residues that form the contact surfaces of the variable regions to suppress the association described above but not to suppress (to enhance) the association between variable regions 1 and 2, and between variable regions 3 and 41

When structural isomers having a structure where variable regions 2 and 4 are associated occur in the sc(Fv)2 form, substitution mutations are introduced at the amino acid residues that form the contact surfaces of the variable regions to suppress the association described above but not to suppress (to enhance) the association between variable regions 1 and 2, and between variable regions 3 and 4.

More specific examples are described below, but are not limited thereto.

For example, for decreasing the percentage of the bivalent scFv type and increasing the percentage of the single chain diabody type in an sc(Fv)2 having the arrangement of [VH1] linker [VL2] linker [VH3] linker [VL4], for example, amino acid residues that form the contact surfaces of VH1 and VL2 are substituted with amino acid residues having the same kind of charge. Furthermore, amino acid residues that form the contact surfaces of VH3 and VL4 are substituted with amino acid residues having the same kind of charge, which are not repulsive to (preferably having affinity to) the amino acid residues introduced into VH1 and VL2. Alternatively, for example, the amino acid side chains forming the contact surface of VH1 and VL2 are substituted with larger side chains (knobs), and amino acid side chains forming the contact surface of VH3 and VL4 are substituted with smaller side chains (holes). Such a substitution allows a regulation such that the association between VH1 and VL2, and between VH3 and VL4 is suppressed, but the association between VH1 and VL4, and between VL2 and VH3 is not suppressed (enhanced).

Alternatively, when decreasing the percentage of the single chain diabody type and increasing the percentage of the bivalent scFv type in sc(Fv)2 having the arrangement of: [VH1] linker [VL2] linker [VH3] linker [VL4], for example, amino acid residues that form the contact surface of VH1 and VL4 are substituted with amino acid residues having the same kind of charge. Furthermore, amino acid residues that form the contact surface of VH3 and VL2 are substituted with amino acid residues with the same kind of charge, which are not repulsive to preferably having affinity to) the amino acid residues introduced into VH1 and VL4. Moreover, for example, amino acid side chains that form the contact surface of VH1 and VL4 are substituted with larger side chains (knob), and amino acid side chains that form the contact surface of VH3 and VL2 are substituted with smaller side chains (hole). Such a substitution allows a regulation such that the association between VH1 and VL4 is suppressed, but the association between VH1 and VL2, and between VH3 and VL4 is not suppressed (enhanced).

In a preferred embodiment of the present invention, the present invention provides methods for increasing the content ratio of specific structural isomers in sc(Fv)2 compositions, which comprise the step of substituting the following amino acids residues (1) and (2), or (3) and (4) with amino acid residues of the same kind of charge.

(1) an amino acid residue in the VH of sc(Fv)2, which corresponds to the amino acid residue at position 39 in the heavy chain amino acid sequence
(2) an amino acid residue in the VL of sc(Fv)2, which corresponds to the amino acid residue at position 38 in the heavy chain amino acid sequence
(3) an amino acid residue in the VH of sc(Fv)2, which corresponds to the amino acid residue at position 45 in the heavy chain amino acid sequence
(4) an ammo acid residue in the VL of sc(Fv)2, which corresponds to the amino acid residue at position 44 in the heavy chain amino acid sequence The present invention also provides methods for increasing the content ratio of specific structural isomers in sc(Fv)2 compositions, which comprise the step of substituting a charged amino acid residue for an amino acid residue of either (1) or (2), or either (3) or (4).

(1) an amino acid residue in the VH of sc(Fv)2, which corresponds to the amino acid residue at position 39 in the heavy cha amino acid sequence
(2) an amino acid residue in the VL of sc(Fv)2, which corresponds to the amino acid residue at position 38 in the heavy chain amino acid sequence
(3) an amino acid residue in the VH of sc(Fv)2, which corresponds to the amino acid residue at position 45 in the heavy chain amino acid sequence
(4) an amino acid residue in the VL of sc(Fv)2, which corresponds to the ammo acid residue at position 44 in the heavy chain amino acid sequence In human and mouse, the amino acid residues of (1) to (4) above are in general: (1) glutamine (Q), (2) glutamine (Q), (3) leucine (L), and (4) proline (P), respectively, but are not limited thereto. Other amino acids equivalent to these may be used. For example, an amino acid corresponding to the amino acid residue at position 38 in the amino acid sequence of VL may be, for example, histidine (K) in human. Those skilled in the art can know the type of amino acid residue that corresponds to an amino acid residue at an arbitrary position by referring to previously published documents and such (for example, J. Mol. Recognit. (2003) 16: 113-120).

The isomerization of the structural isomers in sc(Fv)2 compositions, which is described below, ca also be suppressed by substituting amino acid residues that form the contact surface of the heavy chain and light chain variable regions of sc(Fv)2 with charged amino acid residues. The present invention also provides methods for suppressing the isomerization of the structural isomers in sc(Fv)2 compositions, which comprise the step of substituting amino acid residues that form the contact surface of heavy chain and light chain variable regions of sc(Fv)2 with charged no acid residues. A specific embodiment of the step of substituting amino acid residues that form the contact surface of heavy chain and light chain variable regions of sc(Fv)2 with charged amino acid residues is described above.

The present invention provides methods for controlling the ratio of structural isomers in sc(Fv)2 compositions by adjusting the lengths of two end linkers and/or middle liner of sc(Fv)2. In the present invention, the two end linkers are linkers 1 and 3, and the middle liner is linker 2, when sc(Fv)2 has the arrangement of [variable region 1] (liner 1)[variable region 2] (linker 2)[variable region 3] (linker 3)[variable region 4].

Specifically, the ratio of the single chain diabody type in sc(Fv)2 compositions can be increased by adjusting the length of two end linkers to 0 to 12 amino acids and the length of middle linker to 10 to 30 amino acids. Alternatively, the ratio of the bivalent scFv type in sc(Fv)2 compositions can be increased by adjusting the length of two end linkers to 12 to 30 amino acids and the length of middle linker to 0 to 10 amino acids.

Furthermore, the present invention provides methods for producing sc(Fv)2 compositions in which the content ratio of the single chain diabody type is 80% or higher, preferably 90% or higher, and more preferably 95% or higher by adjusting the lengths of the two end linkers and/or the middle linker. Furthermore, the present invention provides methods for producing sc(Fv)2 compositions in which the content ratio of the bivalent scFv type is 80% or higher, preferably 90% or higher, and more preferably 95% or higher by adjusting the lengths of the two end linkers and/or the middle linker.

Specifically, sc(Fv)2 compositions in which the content ratio of the single chain diabody type is 80% or higher can be produced by adjusting the length of two end linkers to 0 to 12 amino acids, and the length of middle linker to 0 to 10 amino acids. Alternatively, sc(Fv)2 compositions in which the content ratio of the bivalent scFv type is 80% or higher can be produced by adjusting the length of two end linkers to 12 to 30 amino acids and the length of middle linker to 0 to 10 amino acids.

The present invention also provides methods for identifying the structures of structural isomers in sc(Fv)2 compositions, which comprise the step of cleaving the linker portions of sc(Fv)2.

Herein, the linker portion refers to a portion comprising a linker and its adjacent region. The adjacent linker region refers to a region consisting of 20 amino acids from the amino acid next to the linker up to the 20th amino acid towards the variable region side. Thus, the linker portion is a portion in which a region consisting of 20 amino acids is linked to each end of a linker.

This method is relatively convenient than methods for analyzing single chain diabody and bivalent scFv types based on chromatography or such. Chromatography allows the separation of the structural isomers, but cannot identify the structures of separated sc(Fv)2. The method of the present invention allows the identification of structural isomers separated by chromatography or such.

The single chain diabody type and bivalent scFv type are different in tertiary structure. Therefore, when any one of the three linker portions is cleaved by an enzyme or such, the products after cleavage differ between the single chain diabody type and bivalent scFv type.

Specifically, when sc(Fv)2 has the arrangement of [variable region 1] (linker 1)[variable region 2] (linker 2)[variable region 3] (linker 3)[variable region 4], the cleavage in the portion of linker 1 or 3 does not result in the dissociation of the bivalent scFv type into two scFv units since the four variable regions are linked together via covalent or non-covalent bonds. However, the cleavage in the portion of linker 2 results in the dissociation of two scFv units: scFv comprising variable regions 1 and 2, and scFv comprising variable regions 3 and 4. The single chain diabody type does not dissociate into two units of scFv even when cleaved at any of the linker portions 1, 2, and 3 because the four variable regions are linked together via covalent or non-covalent bonds (see FIG. 4).

Thus, when the bivalent scFv type is cleaved at any one of the tree linker portions, it gives two types of products, one containing four variable regions and the other containing two variable regions. In contrast, when the single chain diabody type is cleaved at any one of the three linker portions, it only gives products containing four variable regions.

As described above, it is possible to examine whether an sc(Fv)2 is of a single chain diabody type or bivalent scFv type by cleaving one of the linker portions of sc(v) with an enzyme or such, and comparing the resulting products after cleavage. Thus, the present invention provides methods for analyzing the types of the structural isomers in sc(Fv)2 compositions, which comprise the step of cleaving the linker portions of scFv).

Specifically, such methods comprise the steps of:
(a) cleaving linker portions of sc(Fv) in sc(Fv)2 compositions; and
(b) determining the molecular weight or structure of the products after cleavage.

Generally, the linker portions of sc(Fv)2 are known to be sensitive to proteases and such, because the linker portions do not form a higher order structure (Hoedemaeker et al., J Biol Chem (1997) 272: 29784-29789). The method for cleaving the linkers is not particularly limited, however cleavage by enzymes is preferred and cleavage by proteases is particularly preferred. Proteases to be used are not particularly limited. Any exopeptidase or endopeptidase can be used; however, endopeptidases are preferred for the purpose of cleaving linkers. Any endopeptidase, including serine protease, thiol peptidase, acidic protease, and metalloprotease, can be used. Those skilled in the art can suitably select an endopeptidase depending on the amino acid sequence and linker type. Such serine proteases include, for example, trypsin that specifically hydrolyzes the C terminal side of Arg or Lys residue and subtilisin that non-specifically hydrolyzes proteins and peptides. Alternatively, thiol proteases such as pyroglutamate aminopeptidase that specifically hydrolyzes pGlu residue at the N terminus of proteins and peptides, and papain that non-specifically hydrolyzes proteins and peptides can be used.

The number of linkers to be cleaved is not limited; however it is preferably one. Conditions for cleaving a single linker can be determined by methods known to those skilled in the art.

Furthermore, the molecular weight or structure of the products after cleavage are preferably determined while retaining non-covalent bonds between the variable regions. For example, native PAGE and gel filtration can be used.

All prior art documents cited herein are incorporated herein by reference in their entirety.

EXAMPLES

The present invention is specifically illustrated below using Examples, but it is not to be construed as being limited thereto Example 1

Separation of Structural Isomers of VB22B sc(Fv)2, Determination of their Structures, and Activity Assay 1-1. Preparation of Anti-Human Mpl Antibody VB22B sc(Fv)2

The anti-human Mpl antibody VB22B sc(Fv)2 was prepared as described in PCT/JP2004/18506 (International Patent Application WO2005/56604). Specifically, cDNA for the antibody variable region from mouse hybridoma VB228 producing anti-human Mpl antibody was cloned. A DNA comprising the nucleotide sequence (SEQ ID NO: 3) having the arrangement of VH-linker sequence-VL-linker sequence-VH-linker sequence-VL-Flag tag sequence was prepared using the nucleotide sequence encoding the linker sequence (GlyGlyGlyGlySer)×3 (SEQ ID NO: 1) and the nucleotide sequence encoding a FLAG sequence (Asp-TyrLysAspAspAspAspLys) (SEQ ID NO: 2). This DNA fragment was cloned into the expression vector pCXND3 to construct an expression vector for VB22B sc(Fv)2. This vector was introduced into CHO-DG44 cells, and thus a stably expressing cell line was prepared. Specifically, a mixture of the expression vector (25 µg) and 0.75 ml of CHO-DG44 cells ($1\times10^7$ cells/ml) suspended in PBS was cooled on ice for 10 minutes, and transferred into a cuvette. The mixture was then pulsed at 1.5 kV and 25 µFD using Gene PulserII (BioRad). After 10 minutes of recovery at room temperature, the cells treated by electroporation were added to CHO-S-SFMII medium (Invitrogen) containing 500 µg/ml Geneticin (Invitrogen). Then, a VB22B sc(Fv)2-producing CHO cell line was established through selection.

Then, the culture supernatant of this cell line was loaded onto a Macro-Prep Ceramic Hydroxyapatite Type I (Bio-Rad) column equilibrated with a 20 mM phosphate buffer (pH6.8), and VB22B sc(Fv)2 was eluted in a stepwise manner with 250 mM phosphate buffer (pH6.8). The eluted fraction was concentrated on an ultrafilter, and then fractionated by gel filtration chromatography using a HiLoad 26/60 Superdex 200 pg (Amersham Biosciences) column, and a fraction corresponding to the molecular weight range of about 40 kD to 70 kD was obtained. The fraction was loaded onto an Anti-Flag M2 Affinity Gel column (Sigma-Aldrich) equilibrated with a 50 mM Tris-HCl buffer (pH7.4) containing 150 mM NaCl and 0.05% Tween 20. The absorbed antibody was eluted with 100 mM glycine-HCl (pH3.5). The eluted fraction was immediately neutralized with 1 M Tris-HCl (pH8.0), and loaded onto a HiLoad 26/60 Superdex 200 pg (Amersham Biosciences) column for gel filtration chromatography. 20 mM acetate buffer (pH6.0) containing 150 M NaCl and 0.01% Tween 80 was used in the gel filtration chromatography.

1-2. Separation of Structural Isomers of VB22B sc(Fv)2

VB22B sc(Fv)2 is an sc(Fv)2 comprising the sequence of $VH_1$-linker-$VL_2$-linker-$VH_3$-linker-$VL_4$. Therefore, depending on the combinations of Fv (a molecule in which VH and VL are non-covalently linked), there would be two types of structural isomers: the bivalent scFv type in which each set of $VH_1$ and $VL_2$, and VH3 and VL4 form an Fv; and the single chain diabody type in which each set of $VH_1$ and $VL_4$, and $VH_2$ and $VL_3$ form an Fv (FIG. 1). As a result of examining structural isomer separation of VB22B sc(Fv)2, the inventors succeeded in separating various structural isomers of VB22B sc(Fv)2 by using anion exchange chromatography MONO Q (Amersham Biosciences) under the following elution conditions.

<Elution Conditions>
Mobile phase A: 20 mM Tris-HCl, pH 8.0
Mobile phase B: 20 mM Tris-HCl, 500 mM NaCl, pH 8.0
Flowrate: 1.0 ml/min
Gradient: B0%→B35% (30 min)

Figure 2:
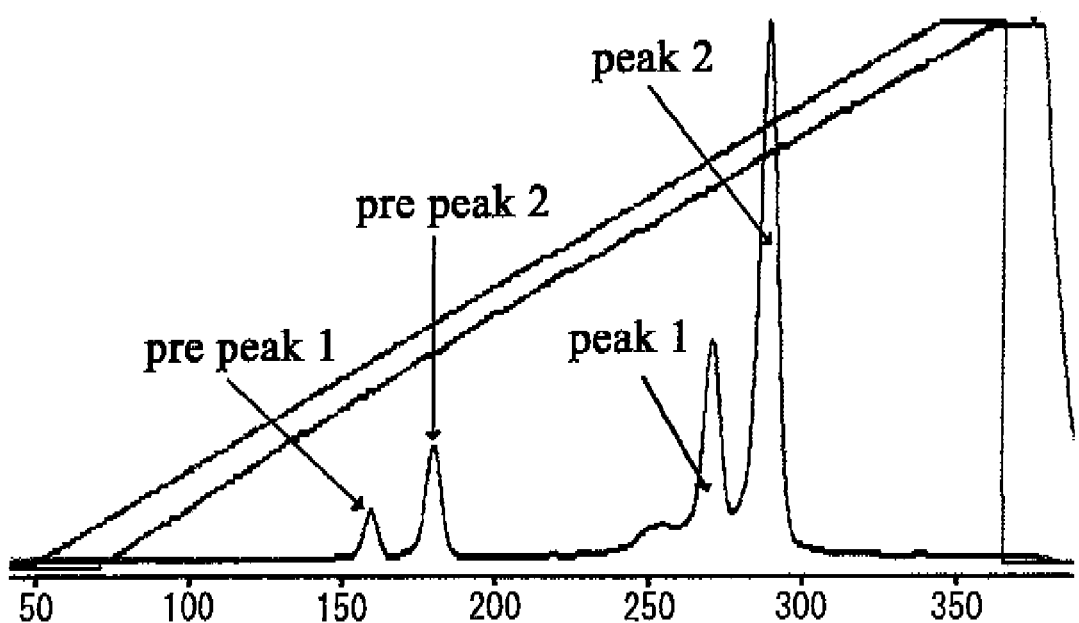
FIG. 2 shows results of separation of peak 1 and peak 2 in anion exchange chromatography.

Under the conditions described above, VB22B sc(Fv)2 was separated into four peaks. The chromatogram shown in FIG. 2 was obtained. The peaks were named pre peak 1, pre peak 2, peak 1, and peak 2 sing from the peak with the shortest retention time.

Sample solutions for peak 1 and peak 2 were introduced into Q-TOF mass spectrometer (Q Tof Ultima, Micro Mass) by infusion. Appended software (MassLynx) was used for a deconvolution of the obtained multivalent ion spectra (+). The result showed that the molecular weights were 54115 Da for peak 1 and 54112 Da for peak 2. This suggests that the molecular weights for peak 1 and peak 2 are the same.

Peak 1 and peak 2 were suggested to be structural isomers (conformational isomers) since VB22B sc(Fv)2 was not glycosylated and moreover, peak 1 and peak 2 had an identical amino acid primary structure but different tertiary structures that were separated by ion exchange chromatography. Previously published documents suggested the presence of such structural isomers; however, the finding described above allowed separation of structural isomers for the first time.

1-3. Determination of the Structures of the Structural Isomers of VB22B sc(Fv)2

VB22B sc(Fv)2 is an sc(Fv)2 comprising the sequence of $VH_1$-linker-$VL_2$-linker-$VH_3$-linker-$VL_4$. Therefore, depending on the combinations of Fv (a molecule in which VH and VL are non-covalently linked), two types of structural isomers are predicted to exist: the bivalent scFv type in which each set of $VH_1$ and $VL_2$, and $VH_3$ and $VL_4$ forms a Fv; and the single chain diabody type in which each set of $VH_1$ and $VL_4$, and $VH_2$ and $VL_3$ forms a Fv. Thus, peak 1 and peak 2 would be of those structural isomers described above.

Through investigations described herein, a protease-based limited proteolysis method was found as an analytical method for identifying the two types of structural isomers. The linker portions of sc(Fv)2 are thought to have a relatively flexible structure and thus be less tolerant to proteases.

Figure 3:
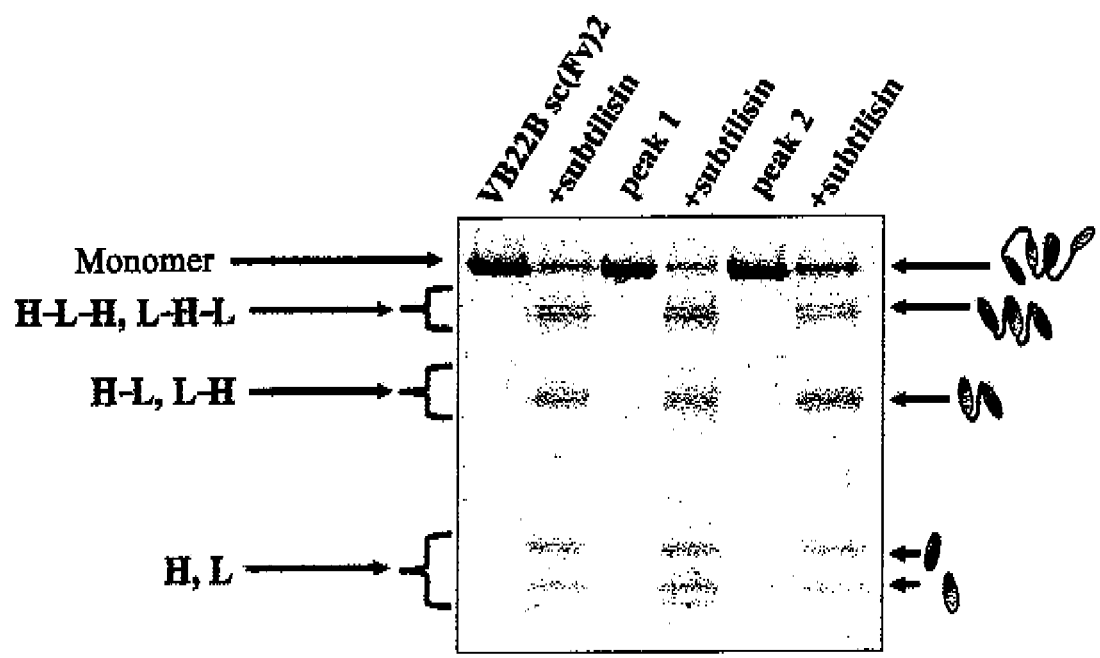
FIG. 3 shows the result of reducing SDS-PAGE of peak 1, peak 2, and VB22B sc(Fv)2 before and after subtilisin treatment. The putative structures for the obtained bands are shown on the right.

Peak 1, peak 2, and VB22B bulk (peak 1: peak 2=1:3) were reacted with subtilisin A, a type of protease, under the following conditions.
<Reaction Conditions>
20 mM sodium citrate, 150 mM NaCl, pH 7.5
VB22B sc(Fv)2 peak 1 or peak 2: 0.14 mg/ml
Subtilisin A: 1 μg/ml
37° C., 30 min Following the reaction described above, reducing SDS-PAGE was carried out using TrisGlycine SDS gel (12%). As a result VB22B bulk prior to separating the structural isomers), peak 1 and peak 2 all showed the same band pattern (FIG. 3). A band specific to each fragment resulting from the cleavage of VB22B sc(Fv)2 at the three linker portions was obtained. This indicated that the linker portions of VB22B sc(Fv)2 can be partially and limitedly degraded using the above-described reaction conditions.

Figure 4:
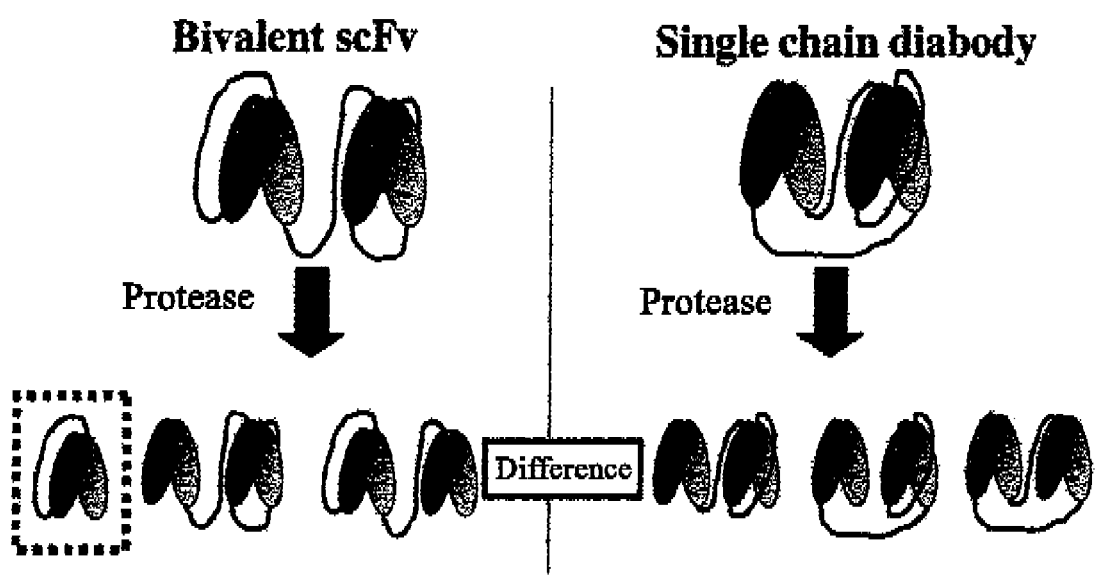
FIG. 4 shows a diagram illustrating the difference in the proteolytic pattern after limited proteolysis by subtilisin. The difference results from the structural difference between the bivalent scFv and single chain antibody. In the case of bivalent scFv structure, the low molecular weight antibody fragment is formed, which is boxed with a dotted line.
Figure 5:
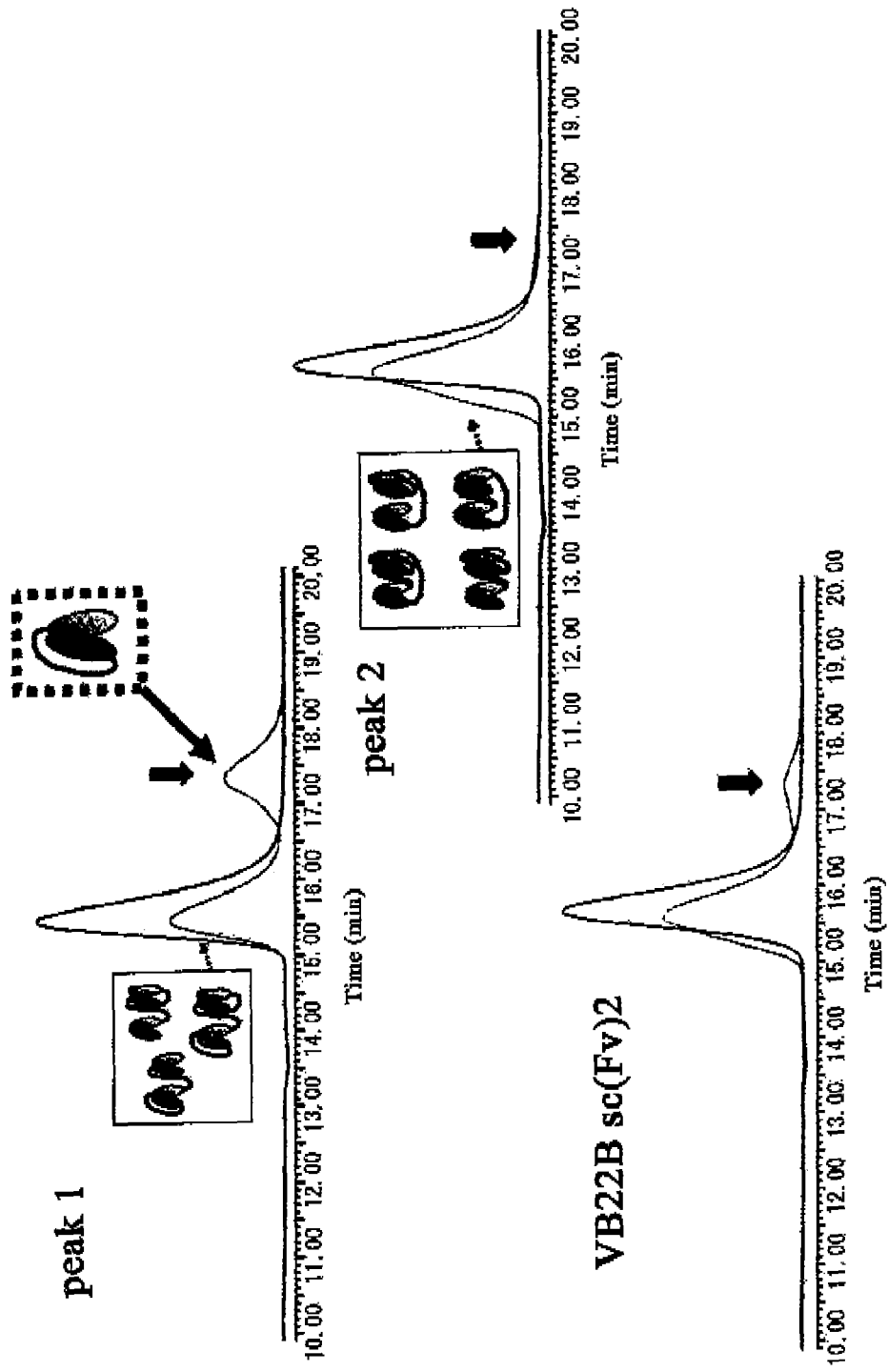
FIG. 5 shows a result of gel filtration chromatography after limited proteolysis of peak 1, peak 2, and VB22B sc(Fv)2 by subtilisin. The elution position of the low molecular weight antibody peaks are indicated by the arrows.

As shown in FIG. 4, when cleavage occurs at one of the three linkers in the two types of structural isomers, in the non-denatured state, cleavage at any of the three linkers does not alter the apparent molecular weight in the structure of single chain diabody type in which VH and VL are non-covalently linked together. However, when cleavage at the middle linker of the bivalent scFv type occurs, molecular species with half the molecular weight is produced. Thus, VB22B sc(Fv)2 bulk, peak 1, and peak 2 after partial linker cleavage under the reaction conditions described above were analyzed by gel filtration chromatography using TSK Super2000 (TOSOH). Gel filtration chromatography was carried out using the following conditions:
Mobile phase. DPBS(−) pH 7.4
Flow rate: 0.2 ml/min As shown in FIG. 5, the result showed no low molecular weight antibody peak in peak 2, while a low molecular weight antibody peak (about one half of the original molecular weight) was found in peak 1. VB22B sc(Fv)2 bulk, a mixture of peak 1 and peak 2, was also found to give a low molecular weight antibody peak with a level relevant to the abundance of peak 1. Thus, peak 1 and peak 2 were identified as bivalent scFv type and single chain diabody type, respectively.

This series of procedures enable the separation of structural isomers contained in VB22B sc(Fv)2 and identification of their structures. Previously published documents predict the structures of structural isomers based on model prediction. The present investigation discovered methods for identifying the structures of separated structural isomers. Furthermore, it allowed quantitative evaluation of the abundance ratio of the structural isomers—the bivalent scFv and single chain diabody structures contained in VB22B sc(Fv)2—from the peak areas of ion exchange chromatography.

1-4. Biological Activity Assay of the Structural Isomers of VB22B sc(Fv)2

A document (Blood (2005) 105:562-566) has reported that anti-human Mpl antibody VB22B sc(Fv)2 exhibits a TPO-like agonistic activity. Thus, TPO-like agonistic activity of the separated structural isomers was assessed using BaF3-human Mpl or BaF3-monkey Mpl that proliferate in a TPO-dependent manner.

Cells from each cell line were washed twice with RPMI 1640/1% FBS (fetal bovine serum) (Invitrogen), and then suspended in RPMI 1640/10% FBS to a concentration of $4 \times 10^5$ cells/ml. Cell suspensions were aliquoted at 60 μl/well into a 96-well plate. Various concentrations of rhTPO (R&D) and samples of the structural isomers were prepared, and a 40-μl aliquot was added into each well. The plates were then incubated at 37° C. under 5% $CO_2$ for 24 hr. Immediately after an addition of 10-μl aliquot of WST-8 reagent (Cell Count Reagent SF; Nacalai Tesque) into each well, absorbance was measured at 450 nm (and at 655 nm as a control) using Benchmark Plus. After two hours of incubation, absorbance was measured at 450 am (and at 655 nm as a control) again. The WST-8 reagent changes colors at 450 nm in a color reaction that reflects the viable cell count, TPO-like agonistic activity was assessed using the change in absorbance during the two-hour incubation as an index.

Figure 6:
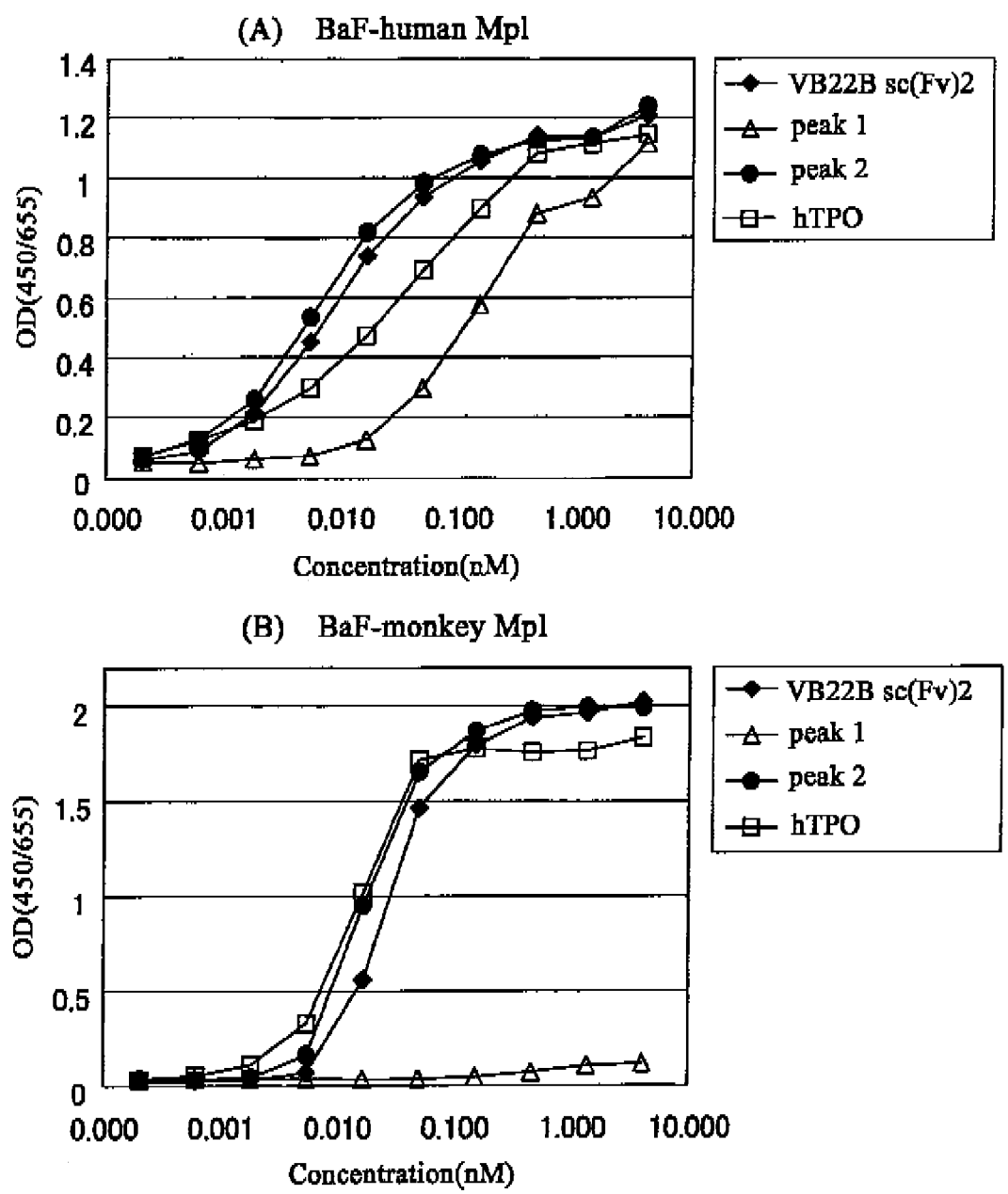
FIGS. 6A and 6B show results of a TPO-like agonistic activity assay of VB22B sc(Fv)2 structural isomers using BaF cells and human Mpl (FIG. 6A or monkey Mpl (FIG. 6B).

Purified structural isomers of VB22B sc(Fv)2 were assayed for their TPO-like agonistic activity using BaF3-human Mpl and BaF3-monkey Mpl. The results are shown in FIG. 6. The comparison of agonistic activities between the structural isomers of peak 1 and peak 2 revealed that peak 2 exhibits a significantly higher activity. This suggests that anti-Mpl antibody sc(Fv)2 needs to form a single chain diabody structure in order to exert the TPO-like agonistic activity.

Example 2

Separation of Structural Isomers of hVB22B u2-wz4 sc(Fv)2, Identification of their Structures, and Activity Assay 2-1. Preparation of Humanized Anti-Human Mpl Antibody hVB22B u2-wz4 sc(Fv)2

Humanized antibodies were prepared by grafting a complementarity-determining region (hereinafter abbreviated as "CDR") into the framework regions (hereinafter abbreviated as "FR1") of variable regions of VB22B sc(Fv)2 prepared in Example 1. Specifically, synthetic oligo DNAs of about 50 nucleotides were designed so as to make about 20 nucleotides available for hybridization. The synthetic oligo DNAs was also designed such that the resulting gene will have a nucleotide sequence (SEQ ID NO, 4) having the arrangement of VH-linker-sequence-VL-linker sequence-VH-linker sequence-VL, using a nucleotide sequence encoding the linker sequence (GlyGlyGlyGlySer)×3 (SEQ ID NO: 1). These synthetic oligo DNAs were assembled together by PCR to prepare the gene encoding the respective variable regions. To express the obtained gene in animal cells, an expression vector was constructed, the cell line CHO-DG44 constitutively expressing the antibody was prepared, and culture supernatants were collected by the same method as that described in Example 1-1. The humanized antibody hVB22B u2-wz4 sc(Fv)2, which is not Flag-tagged, was purified from culture supernatants using a fusion protein of GST and MG10 (Gln213 to Ala231 in the amino acid sequence of human Mpl), which is an epitope recognized by VB22B sc(Fv)2.

The MG10-GST fusion protein was purified using Glutathione Sepharose 4B (Amersham Biosciences) according to the supplier's protocol. Then the purified MG10-GST fusion protein was immobilized onto a HiTrap NHS-activated HP Column (Amersham Biosciences) to prepare an affinity column, according to the supplier's protocol. The culture supernatant of CHO cells expressing the humanized antibody hVB22B u2-wz4 sc(Fv)2 was loaded onto the MG10-GST fusion protein-immobilized column. The adsorbed humanized antibody hVB22B u2-wz4 sc(Fv)2 was eluted with 100 mM glycine-HCl (pH3.5)/0.01% Tween 80. Immediately after elution, the eluted fraction was neutralized with 1 M Tris-HCl (pH7.4), and was further subjected to gel filtration chromatography using a HiLoad 16/60 Superdex 200 pg (Amersham Biosciences). 20 mM citrate buffer pH7.5) containing 300 mM NaCl and 0.01% Tween 80 was used in the gel filtration chromatography.

2-2. Separation and Purification of Structural Isomers of hVB22B u2-wz4 sc(Fv)2 hVB22B u2-wz4 sc(Fv)2 is an sc(Fv)2 comprising the sequence of $VH_1$-linker-$VL_2$-linker-$VH_3$-linker-$VL_4$. Therefore, as is the case of VB22B sc(Fv)2, depending on the combinations of Fv (a molecule in which VH and VL are non-covalently linked), there would be two types of structural isomers: the bivalent scFv type in which each set of $VH_1$ and $VL_2$, an $VH_3$ and $VL_4$ form a Fv; and the single chain diabody type in which each set of $VH_1$ and $VL_4$, and $VH_2$ and $VL_3$ form a Fv (FIG. 1).

The separation of structural isomers of hVB22B u2-wz4 sc(Fv)2 was examined. The result suggested that various components of hVB22B u2-wz4 sc(Fv)2 can be separated using cation exchange chromatography BioAssist S (TOSOH) under the following elution conditions:
Mobile phase A: 20 mM sodium phosphate, pH 7.5
Mobile phase B: 20 mM sodium phosphate, 500 mM NaCl, pH 7.5
Flow rate: 0.8 ml/min
Gradient: B0%→B35% (30 min)

Figure 7:
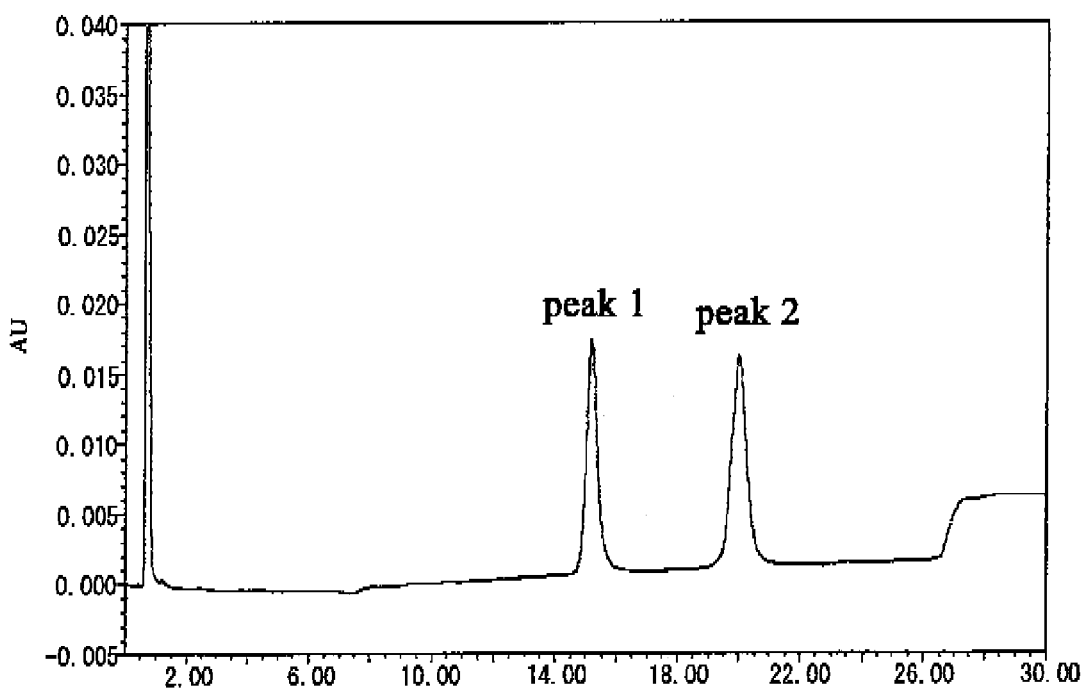
FIG. 7 shows results of separating peak 1 and peak 2, using cation exchange chromatography.

Under the conditions described above, hVB22B u2-wz4 sc(Fv)2 was separated into two peaks. The chromatogram shown in FIG. 7 was obtained. The peaks were named peak 1 and peak 2 starting from the peak with the shorter retention time.

The molecular weights for peak 1 and peak 2 were determined using Q-TOF mass spectrometer (Q Tof Ultima, Micro Mass). Sample solutions were introduced into Q-TOF by infusion. Appended software (MassLynx) was used for deconvolution of the obtained multivalent ion spectra (+). The result showed that the molecular weights were 53768 Da for peak 1, and 53769 Da for peak 2. Accordingly, the molecular weights for peak 1 and peak 2 were found to be identical.

Figure 8:
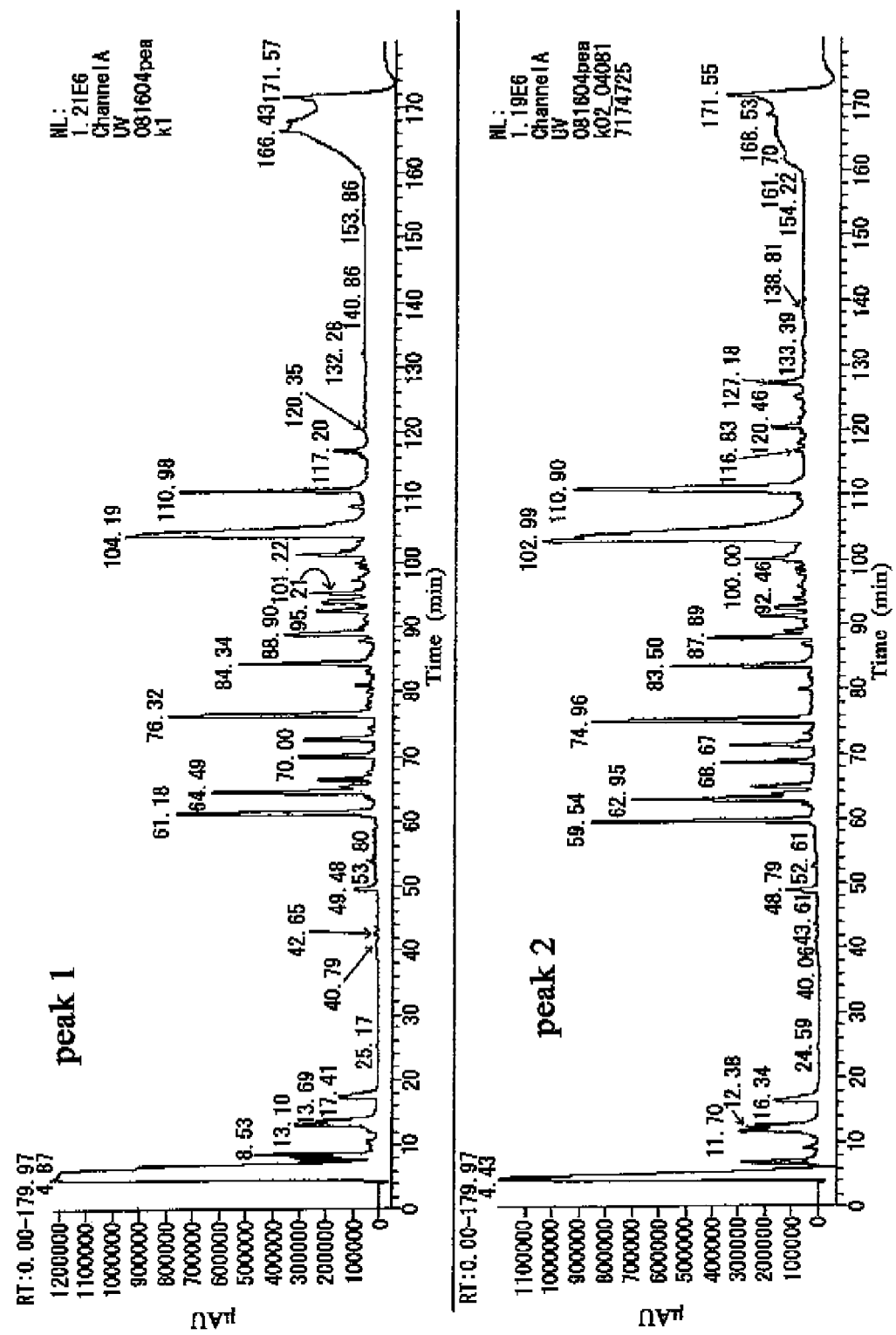
FIG. 8 shows peptide mapping of peak 1 and peak 2 which were separated by cation exchange chromatography.

Peptide mapping for peak 1 and peak 2 was carried out. After reduction and denaturation followed by carboxymethylation, the samples were degraded into peptide fragments using trypsin, and peptide maps were obtained using reversed-phase chromatography (YMC-Pack-OLDS). The peptide maps for peak 1 and peak 2 were compared, which revealed that the mapping patterns of peak 1 and peak 2 were identical, as shown in FIG. 8. Thus, the amino acid primary structures were found to be identical to each other.

hVB22B u2-wz4 sc(Fv)2 was not glycosylated, and the molecular weights for peak 1 and peak 2 were identical when determined by TOF-MASS. I addition, the mapping patterns for peak 1 and peak 2 were identical to each other. Accordingly, these findings show that peak 1 and peak 2 are structural isomers (conformational isomers) having different tertiary structures.

hVB22B u2-wz4 sc(Fv)2 is an sc(Fv)2 comprising the sequence of $VH_1$-linker-$VL_2$-linker-$VH_3$-linker-$VL_4$, as shown in FIG. 1. Therefore, depending on the combinations of Fv (a molecule in which VH and VL are noncovalently linked), there would be two types of structural isomers: the bivalent scFv type in which each set of $VH_1$ and $VL_2$, and $VH_3$ and $VL_4$ forms a Fv; and the single chain diabody type in which each set of $VH_1$ and $VL_4$, and VH2 and $VL_3$ forms a Fv. Thus, each of peak 1 and peak 2 would have the structure of either bivalent scFv type or single chain diabody type.

Figure 9:
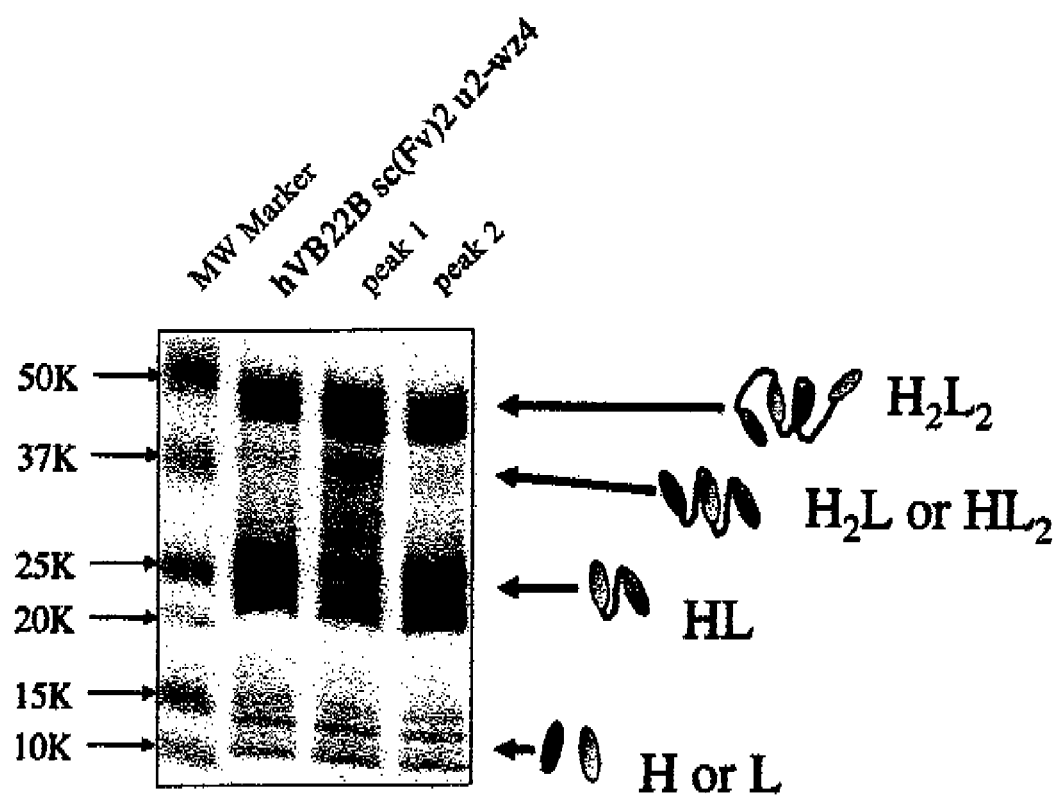
FIG. 9 shows results of reducing SDS-PAGE of peak 1, peak 2, and hVB22B u2-wz4 sc(Fv)2 after subtilisin treatment. The structures of the obtained bands are shown on the right.

A protease-based limited proteolysis method was found as an analytical method for identifying the two types of structural isomers. The linker portions of sc(Fv)2 are thought to be relatively flexible in their structures and thus be less tolerant to proteases. Peak 1, peak 2, and hVB22B u2-wz4 sc(Fv)2 (peak 1:peak 2=1:4) were incubated with subtilisin A, a type of protease, under the following conditions:
20 µM sodium citrate, 150 mM NaCl, pH 7.5
hVB22B u2-wz4 sc(Fv)2 peak1 or peak2: 0.15 mg/ml
Subtilisin A: 10 µg/ml
37° C., 30 min After the reaction, reducing SDS-PAGE was carried out using 12.5% Phastgel Homogeneous. According to the result, all of hVB22B u2-wz4 sc(Fv)2 bulk, peak1, and peak2 showed the same band pattern, as shown in FIG. 9. A band specific to each fragment that resulted from the cleavage of hVB22B u2-wz4 sc(Fv)2 at the three linker portions was obtained. This indicated that the linker portions of hVB22B u2-wz4 sc(Fv)2 can be degraded partially and limitedly using the reaction condition described above.

Figure 10:
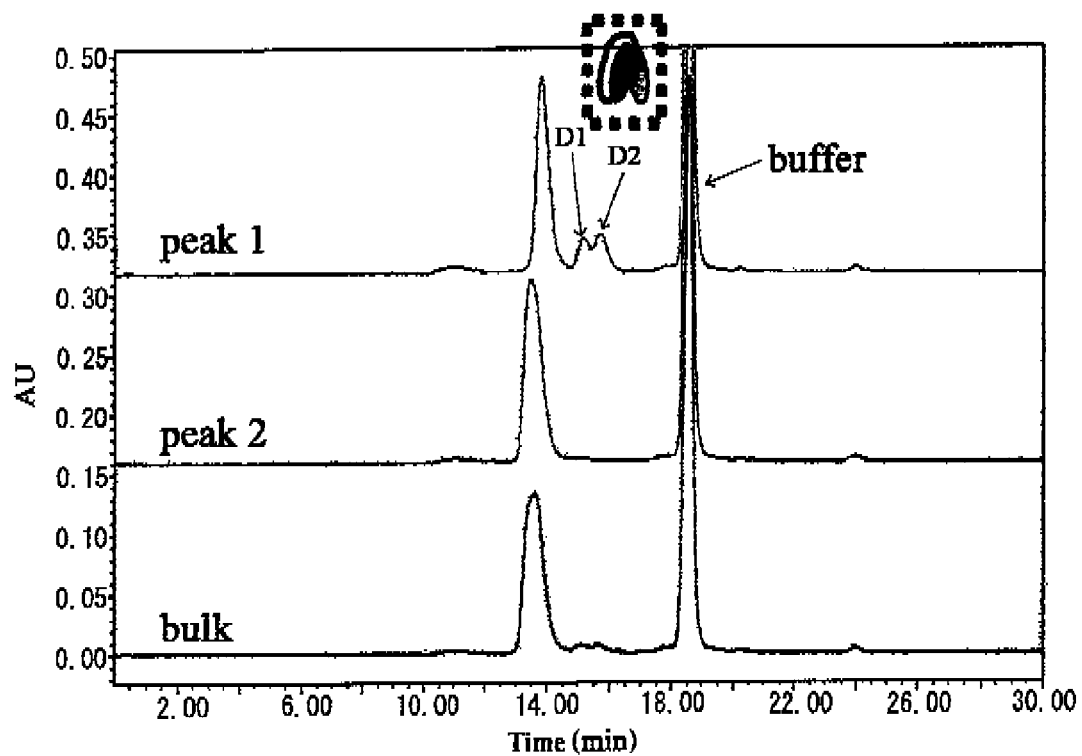
FIG. 10 shows results of gel filtration chromatography after limited proteolysis of peak 1, peak 2, and hVB22B u2-wz4 sc(Fv)2 by subtilisin. The elution position of the low molecular weight antibody peak is indicated by the arrows.

As shown in FIG. 4, when cleavage occurs at one of the three linkers in the structures of bivalent scFv type and single chain diabody type, in the non-denatured state, cleavage at any of the three linkers does not alter the apparent molecular weight in the structure of single chain diabody type in which VH and VL are non-covalently linked together. However, when cleavage at the middle linker of the bivalent scFv type occurs, molecular species with half the molecular weight are produced. Thus, hVB22B u2-wz4 sc(Fv)2 bulk, peak 1, and peak 2 after partial linker cleavage under the reaction conditions described above were analyzed by gel filtration chromatography using TSK Super2000 (TOSOH). Gel filtration chromatography was carried out under the following conditions:
Mobile phase: DPBS(−) pH 7.4
Flow rate: 0.2 ml/min As shown in FIG. 10, the result showed that there was no low molecular weight antibody peak in peak 2, while there was one in peak 1 (about one half of the original molecular weight). hVB22B sc(Fv)2 u2-wz4 bulk, a mixture of peak 1 and peak 2, was also found to give a low molecular weight antibody peak with a level relevant to the abundance of peak 1. Thus, based on the result, peak 1 and peak 2 were identified as the bivalent scFv type and single chain diabody type, respectively.

2-3. Binding Activity Assay of the Structural Isomers of hVB22B u2-wz4 sc(Fv)2

The binding activities of hVB22B u2-wz4 sc(Fv)2, and peak 1 and peak 2 separated from hVB22B u2-wz4 sc(Fv)2 were evaluated as described below. Sensor Chip CM5 Biacore) was placed in Biacore 3000 (Biacore), and a fusion protein of MG10 (Gln213 to Ala231 of human Mpl) and GST described in Section 2-1 was immobilized onto the chip by the amine-coupling method. HSS-EP Buffer (Biacore) was used as the running buffer for the measurement. The flow rate was 20 µl/min. Six concentrations of each of humanized VB22B u2-wz4 sc(Fv)2 bulk, peak 1, and peak 2 within about 5 to 150 nM were prepared using HBS-EP Buffer. Each of the samples was injected over the above-described MG10-immobilized cell for 2 minutes to reveal the binding region. Then, the measurement was conducted for 2 minutes to reveal the dissociation region. VB22B sc(Fv)2 bound to the MG10-GST fusion protein was removed by injecting 20 mM HCl for 1 minute to recover the immobilized cell. The association rate constant (ka) and dissociation rate constant (kd) were calculated from the obtained sensorgram using the BIAevaluation Version 3.1 (Alacore) software applying the bivalent analyte model. The result showed that the dissociation constants (KD) for hVB22B u2-wz4 sc(Fv)2 bulk, peak 1, and peak 2 were 1.02×10$^{-8}$ M, 1.24×10$^{-8}$ M, 9.92×10$^{-9}$ M, respectively, as shown in Table 1. The two types of structural isomers were found to have comparable binding activities.

TABLE 1

|  | ka(l/Ms) [×10$^5$] | kd(l/s) [×10$^{-3}$] | KD (nM) |  |
|---|---|---|---|---|
| VB22B peak1 | 5.86 ± 0.06 | 7.27 ± 0.25 | 12.4 ± 0.05 | n = 3 |
| VB22B peak2 | 5.71 ± 0.17 | 5.66 ± 0.24 | 9.92 ± 0.53 | n = 3 |
| VB22B bulk | 6.08 ± 0.30 | 6.17 ± 0.23 | 10.2 ± 0.8 | n = 3 |

2-4. Agonistic Activity Assay of Structural Isomers of hVB22B u2-wz4 sc(Fv)2

Figure 11:
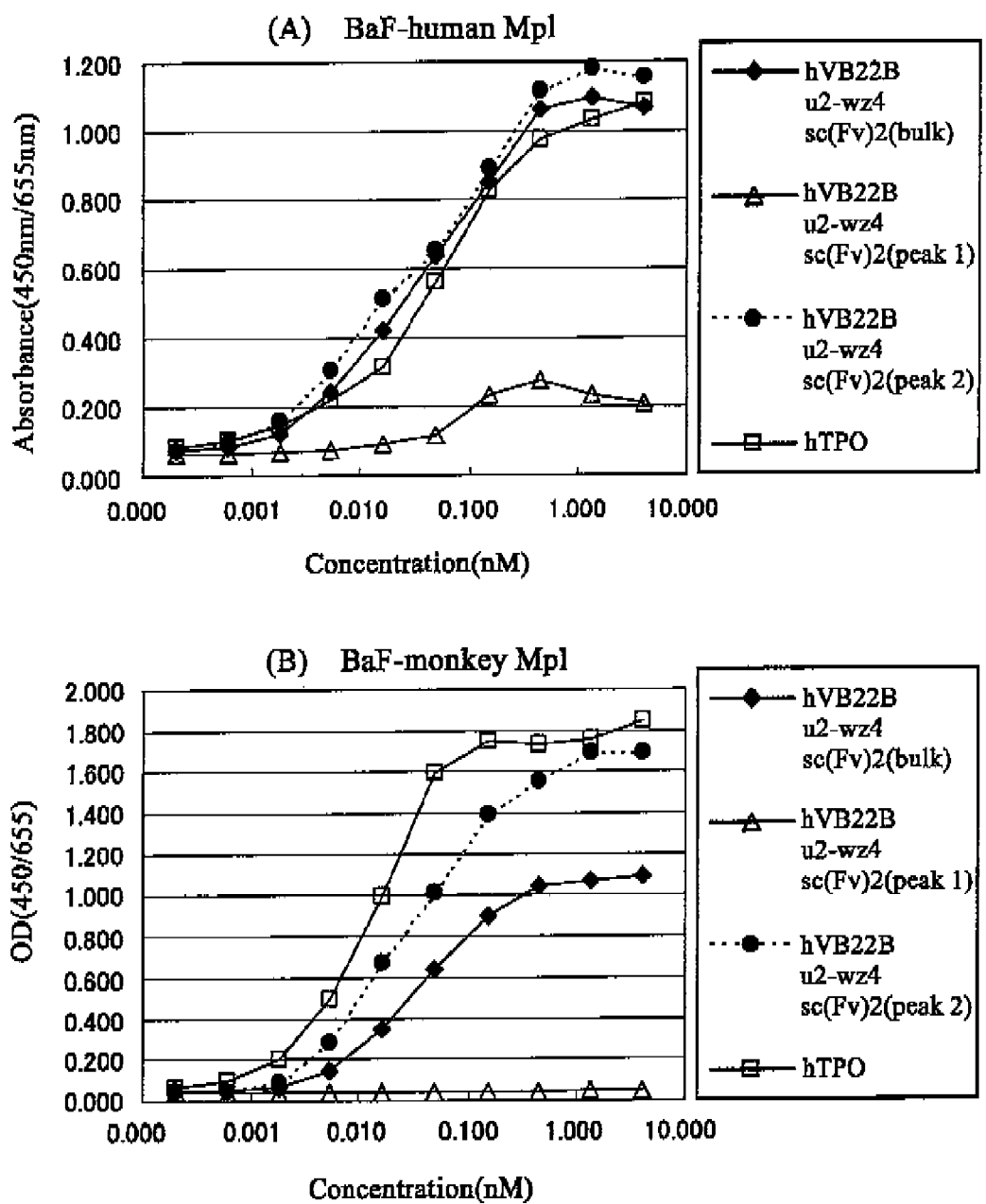
FIGS. 11A and 11B show results from a TPO-like agonistic activity assay of hVB22B u2-wz4 sc(Fv)2 structural isomers using BaF cells and human Mpl (FIG. 11A) or monkey Mpl (FIG. 11B).

Peak 1, peak 2, and hVB22B u2-wz4 sc(Fv)2 were evaluated for their agonistic activities. As shown in FIG. 11, the agonistic activity was markedly different between the structural isomers. While peak 2 for the single chain diabody structure exhibited exceedingly high agonistic activity, the activity was extremely low in peak 1 for the bivalent scFv structure. The binding activity was comparable between the two types of structural isomers; however in contrast, their agonistic activities were significantly different. Neither separation nor identification of the structural isomers was carried out in previously published documents. The investigation described herein discovered for the first time that biological activities between the two types of the structural isomers differ.

The separation of the structural isomers in hVB22B u2-wz4 sc(Fv)2 and identification of their structures can be carried out by this Example. Furthermore, the abundance ratio of the structural isomers each having the bivalent scFv structure or single chain diabody structure in hVB22B u2-wz4 sc(Fv)2 can be quantitatively analyzed based on chromatographic peak areas. The agonistic activity was found to be significantly different between the bivalent scFv structure and single chain diabody structure of hVB22B u2-wz4 sc(Fv)2. Standardization tests to determine properties of the two types of structural isomers of hVB22B u2-wz4 sc(Fv)2 and to quantitatively analyze the content ratio of each structural isomer are essential in the development of hVB22B u2-wz4 sc(Fv)2 comprising the structural isomers with significantly different activity as pharmaceuticals.

Example 3

Analysis of the Abundance Ratio of Structural Isomers of VB22B sc(Fv)2 with Modified Linkers and Regulation of the Ratio of Structural Isomers VB22B sc(Fv)2 is an sc(Fv)2 comprising the sequence of VH$_1$-linker-VL$_2$-linker-VH$_3$-linker-VL$_4$. Therefore, depending on the combinations of Fv (a molecule in which VH and VL are non-covalently linked), there would be two types of structural isomers: the bivalent scFv type in which each set of VH$_1$ and VL$_2$, and VH$_3$ and VL$_4$ form a Fv; and the single chain diabody type in which each set of VH$_1$ and VL$_4$, and VH2 and VL$_3$ form a Fv.

Figure 12:
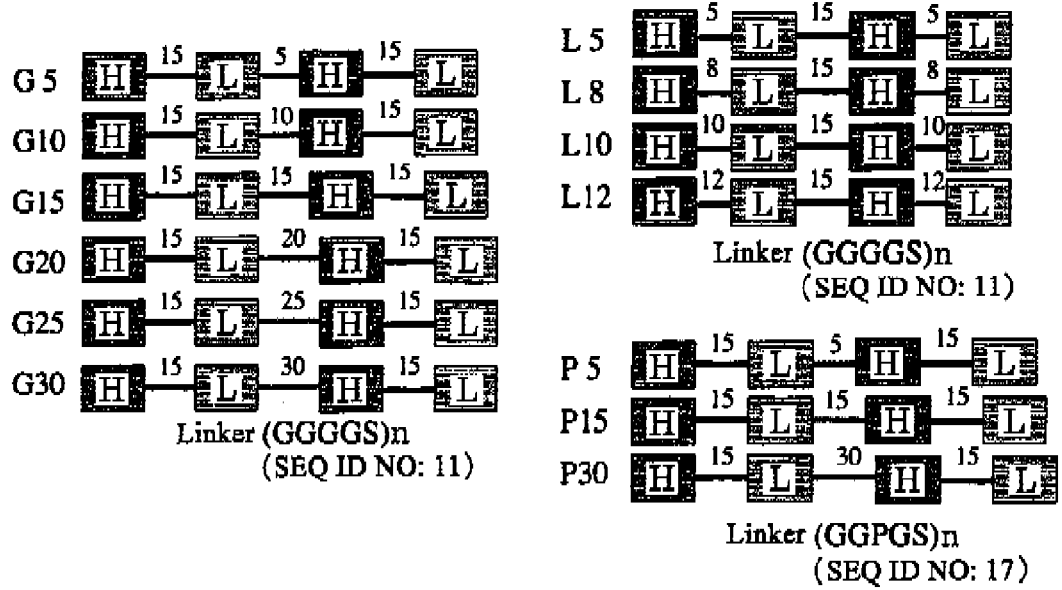
FIG. 12 shows a diagram illustrating each construct with modified linker forms. Gxx represents a construct where the length of middle linker is m. Lxx is a construct where the length of end linkers are xx; the (GGGGS (SEQ ID NO; 11))n sequence was used for each linker. L8 represents a construct where the GGGGSGGS sequence (SEQ ID NO: 20) is used for both end linkers whose length is 8. L12 represents a construct where the GGGGSGGGGSGS sequence (SEQ ID NO: 21) is used for both end linkers whose length is 12. Pxx represents a construct where the length of middle linker is made into xx using the (GGPGS (SEQ ID NO: 17))n sequence as a linker.

The linker in the middle is designated as the middle linker, and the linkers at the two ends are designated as end linkers. Various VB223 sc(Fv)2 with the middle linker or end linkers of varying lengths were prepared as shown in FIG. 12, and the abundance ratio of the structural isomers was quantitatively analyzed under the following conditions:

Column: MONO Q (Amersham biosciences)
Mobile phase A: 20 mM Tris-HCl, pH 8.0
Mobile phase B: 20 mM Tris-HCl, 500 mM NaCl, pH 8.0
Flow rate: 1.0 ml/min
Gradient: B0%→B35% (30 min)

Figure 13:
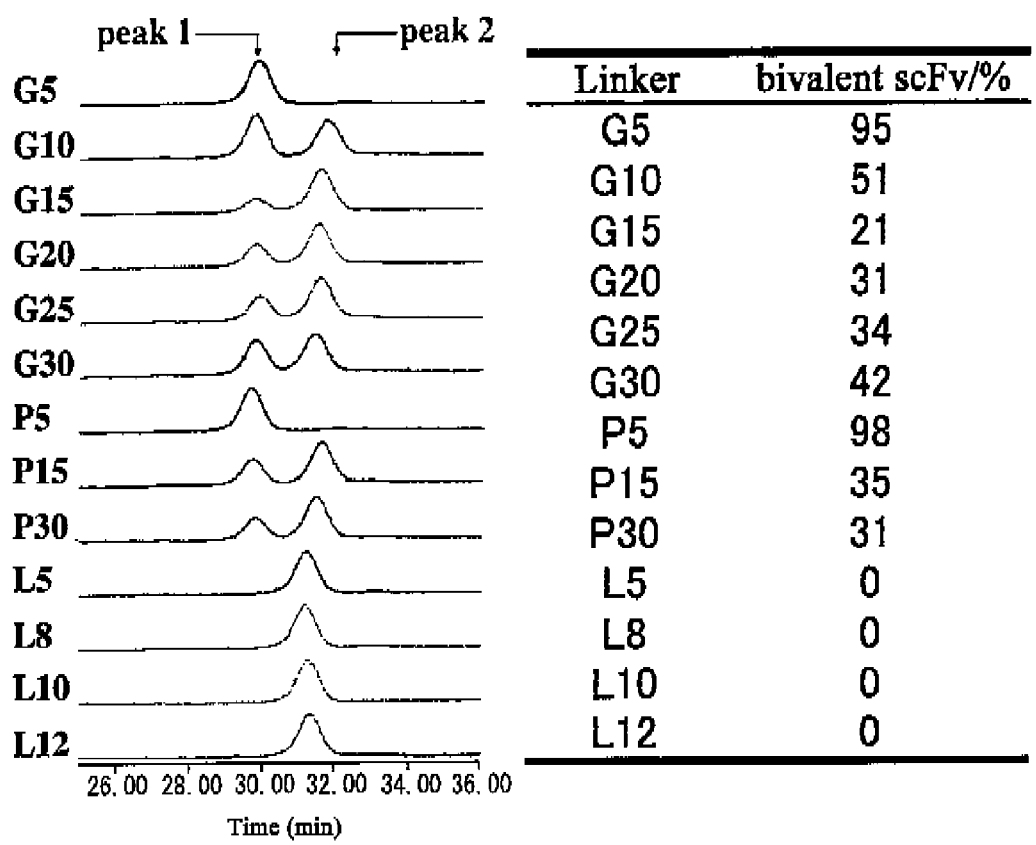
FIG. 13 shows results of anion exchange chromatography analysis of each modified linker form and the abundance ratio of the obtained structural isomers. The percentage of the bivalent scFv type structure is shown.

As a result, as shown in FIG. 13, the two types of structural isomers with linkers of arbitrary lengths were separated by the analytical method described in Example 2, and the abundance ratio of the structural isomers was determined. It was found that the bivalent scFv type and single chain diabody type ratio can be controlled by linker length. The use of this analytical method enables the design of linkers with adequate linker lengths to obtain structural isomers at a desired ratio.

Previously published documents were unable to quantitatively evaluate linker length-dependent abundance ratio of structural isomers since neither methods for identifying the structures of the two types of structural isomers nor quantitative analytical methods were available. Protein Engineering, (1993) 6(8), 989-995, Protein Engineering, (1994) 7(8), 1027-1033, and other documents have reported that in general, an adjacent pair of VH and VL hardly forms a Fv when linker length is 12 or less. The investigation described herein revealed that when G5 or G10 was used, the single chain diabody type structure, in which the adjacent pairs of VH and VL have formed a Fv, was present albeit in a small amount. Thus, the two types of structures (specifically, the structural isomers) are likely to exist irrespective of the type of linker. Quantitative analyses of the abundance ratio of structural isomers would thus be necessary to develop sc(Fv)2 type molecules as pharmaceutics when using any linker. This suggests that the methods of separation and analysis of the present invention, which allow quantitative analysis of the abundance ratio of the structural isomers and separation and purification of the isomers, are extremely useful in developing sc(Fv)2 type pharmaceutical molecules.

Example 4

Large Scale Purification of Structural Isomers Using Cation Exchange Chromatography (Source 15S)

hVB22B u2-wz4 sc(Fv)2 was purified from culture supernatant of hVB22B u2-wz4 sc(Fv)2-expressing CHO cells used in Example 2-1. The culture supernatant was diluted three times with purified water, and then was adjusted to pH 6.0 using 1 M acetic acid. Then, the resulting supernatant was loaded onto SP Sepharose Fast Flow column (Amersham Biosciences) equilibrated with 20 mM sodium acetate buffer (pH 6,0). The column was washed with the same buffer, and then the polypeptide adsorbed onto the column was eluted with a linear gradient of 0 to 0.5 M NaCl in the same buffer (Step 1). The resulting fractions were analyzed by reducing SDS-PAGE using TrisGlycine SDS gel (12%). Fractions containing hVB22B u2-wz4 sc(Fv)2 were collected.

Figure 14:
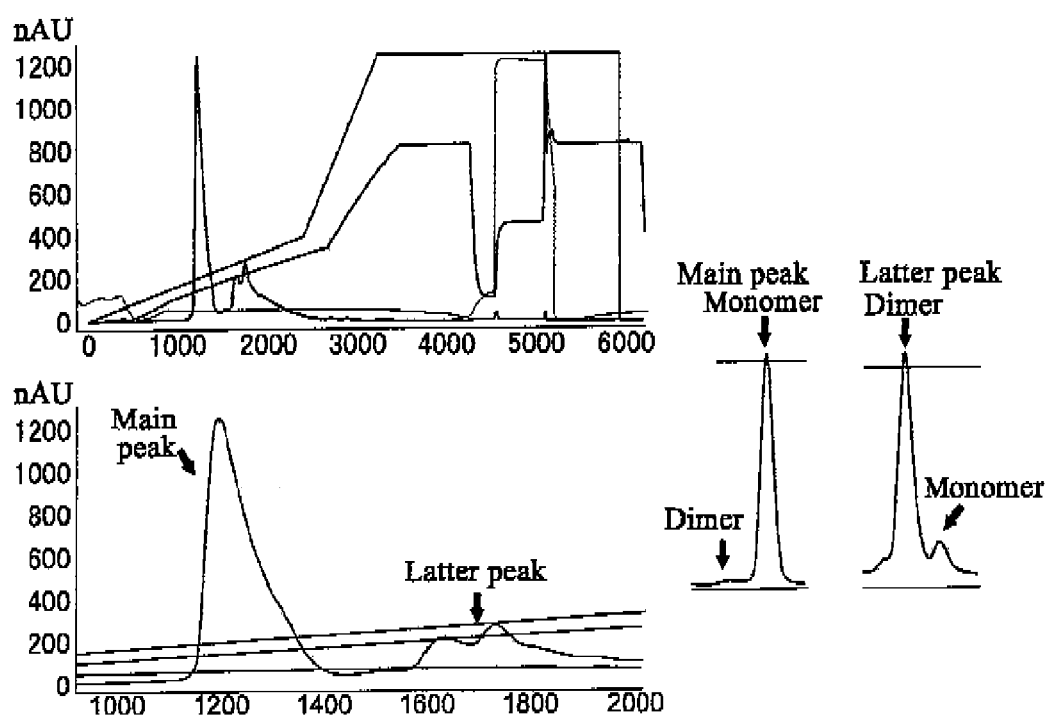
FIG. 14 shows chromatograms of hydroxyapatite column and graphs indicating the result of gel filtration chromatography analysis of the purified fractions.

The hVB22B u2-wz4 sc(Fv)2 fraction in step 1 was loaded onto a hydroxyapatite column (type I, 20 μm; BIO-RAD) equilibrated with 10 mM phosphate buffer OH 6.8). The column was washed with the same buffer. The concentration of the phosphate buffer (pH 6.8) was raised linearly up to 160 mM to elute the polypeptide adsorbed to the column (FIG. 14). Small elution peaks appeared after the main peak. SDS-PAGE analysis revealed that these peaks were all from hVB22B u2-wz4 sc(Fv)2. As shown in the right panel of FIG. 14, analytical gel filtration using a Superdex 200 PC 3.2/30 column (Amersham Biosciences) revealed that the main peak contained mostly hVB22B u2-wz4 sc(Fv)2 monomers and the latter peaks correspond to aggregate fractions for dimers and higher multimers of hVB222B u2-wz4 sc(Fv)2. This indicates that the monomer fraction of hVB22B u2-wz4 sc(Fv)2 can be separated in this step.

Figure 15:
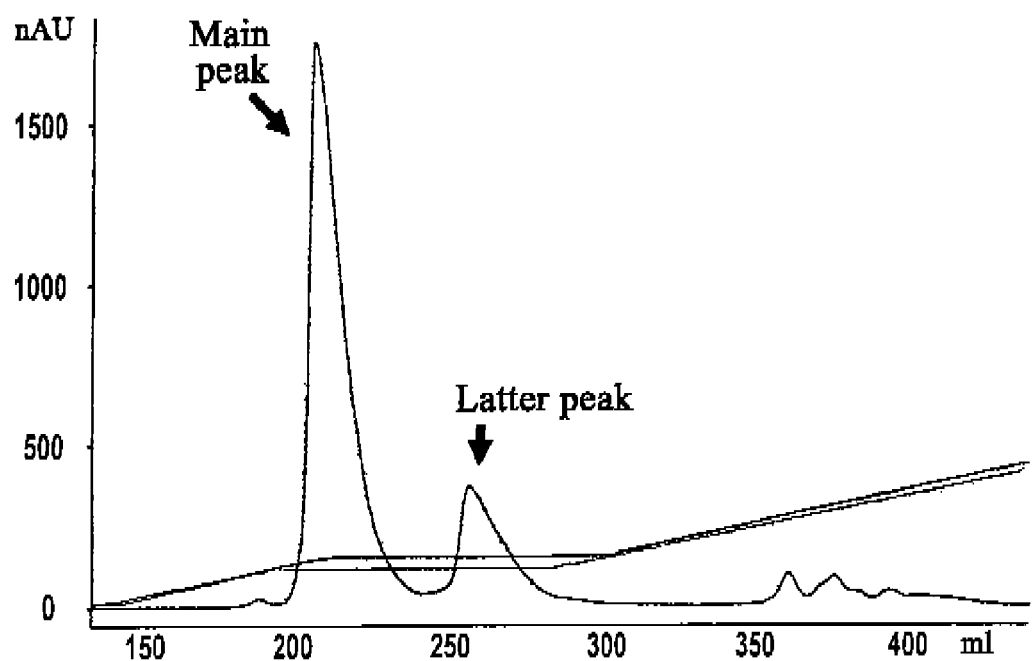
FIG. 15 shows results of chromatographic analysis using SOURCE 15S column.
Figure 16:
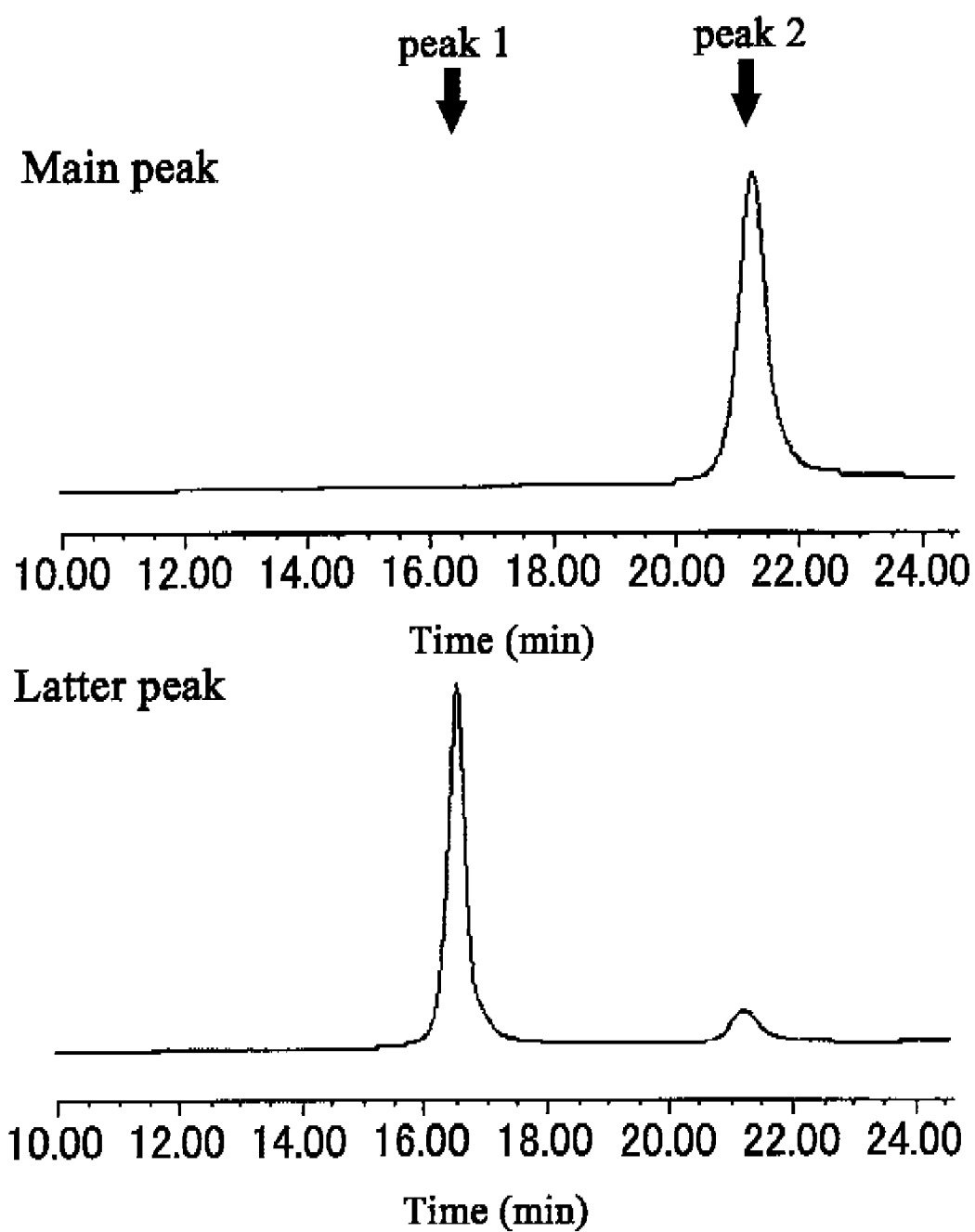
FIG. 16 shows results of cation exchange chromatography analysis.

The monomer fraction for hVB22B u2-wz4 sc(Fv)2 obtained in step 2 was diluted five times with purified water, and then loaded onto SOURCE 15S column (Amersham Biosciences) equilibrated with 20 mM sodium phosphate buffer (pH 7.0). The column was washed with the same buffer. The NaCl concentration was increased linearly from 0 mM up to 36 mM in the same buffer. Then, the NaCl concentration was fixed at 36 mM to maximize the separation of the two peaks during elution. As shown in FIG. 15, after elution of the two peaks of hVB22B u2-wz4 sc(Fv)2, the NaCl concentration was raised again, the polypeptide more strongly adsorbed to the column was eluted, and the column was washed. Analysis using the BioAssist S column described in Section 2-2 revealed that, of these two peaks, the main peak to be eluted first is peak 2, and the one to be eluted next is peak 1 (FIG. 16).

Figure 17:
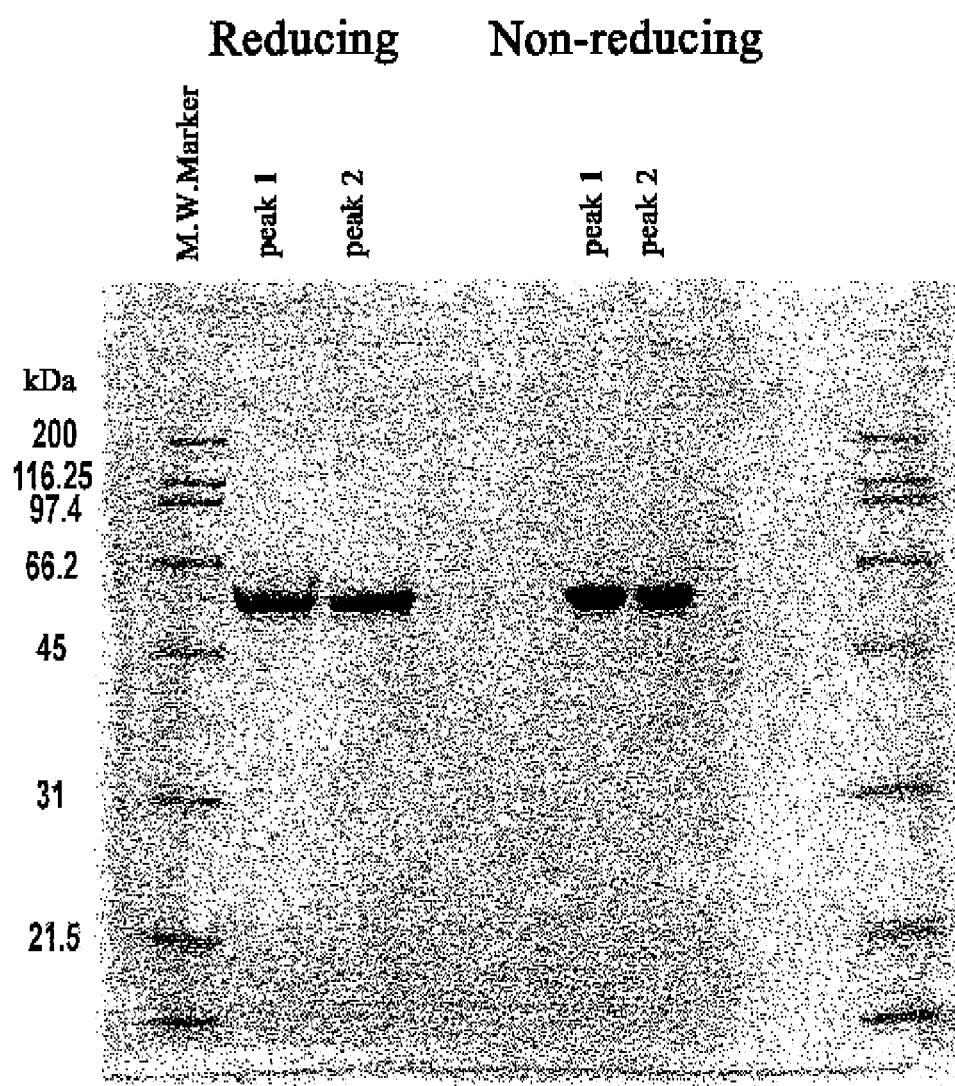
FIG. 17 is a photograph presenting results of SDS-PAGE analysis of peak 1 and peak 2 of hVB22B u2-wz4 sc(Fv)2 purified on a large scale.

Both purified peak 1 and peak 2 for hVR22B u2-wz4 sc(Fv)2 were observed as single bands with a molecular weight of about 55 kDa in SDS-PAGE analyses using the above-described SDS gel under reducing and non-reducing conditions (FIG. 17). Furthermore, peak 1 and peak 2 for hVB22B u2-wz4 sc(Fv)2 each gave a single peak with apparent molecular weight of about 50 kDa in gel filtration chromatography analysis using the TSK Super2000 column described in Sections 1-3 (FIG. 18).

Thus, the present inventors succeeded in developing a method for purifying only the desired monomers of structural isomer of hVB22B u2-wz4 sc(Fv)2 without using gel filtration chromatography that is inadequate for large scale purification.

Example 5

Preparation of VH/VL Contact Surface Modified sc(Fv)2 Type, and Analysis and Identification of Structural Isomers Thereof 5-1. Preparation of VH/VL Contact Surface Modified sc(Fv)2 Type Gln at position 39 of VH (at position 39 in the amino acid sequence of SEQ ID NO; 289 shown in WO 2005/56604) and Gln at position 38 of VL (at position 43 in the amino acid sequence of SEQ ID NO: 291 in WO 2005/56604), which are the amino acids that form the VH/VL contact surface in hVB22B u2-wz4 sc(Fv)2 (hereinafter abbreviated as u2-wz4) prepared in Example 2, were modified by the following procedure. u2-wz4 has the arrangement of: [VH1] linker [VL2] linker [VH3] linker [VL4], which are linked with the amino acid linker sequence (GlyGlyGlyGlySer)$_{x3}$ (SEQ ID NO: 1)), and transcribed and translated from the nucleotide sequence of SEQ ID NO: 4. First, modified hVB22B u2-wz4(v1) sc(Fv)2 gene (hereinafter abbreviated as v1; the nucleotide sequence is shown in SEQ ID NO: 5; the amino acid sequence is shown in SEQ ID NO: 6) with the following modifications was prepared.
Substitution with:
Glu (genetic codon: GAG) for Gln (genetic codon: CAG) at position 39 in VH1;
Glu (genetic codon: GAG) for Gln (genetic codon: CAG) at position 38 in VL2;

Lys (genetic codon: AAG) for Gln (genetic codon: CAG) at position 39 in VH3, and Lys (genetic codon: AAG) for Gln (genetic codon: CAG) at position 38 in VL4. Furthermore, modified hVB22B u2-wz4(v3) sc(Fv)2 gene hereinafter abbreviated as v3; the nucleotide sequence is shown in SEQ ID NO: 7; and the amino acid sequence is shown in SEQ ID NO: 8) with the following modifications was prepared.
Substitution with:
Glu (genetic codon: GAG) for Gln (genetic codon: CAG) at position 39 in VH1;
Lys (genetic codon: AAG) for Gln (genetic codon: CAG) at position 38 in VL2;
Lys (genetic codon: AAG) for Gln (genetic codon: CAG) at position 39 in VH3, and Glu (genetic codon: GAG) for Gln (genetic codon: CAG) at position 38 in VL4. The modification of the gene was carried out by introducing point mutations using QuikChange Site-Directed Mutagenesis Kit (STRATAGENE) according to the manufacturer's protocol. After determination of the nucleotide sequence of each gene, the resulting DNA fragments were cloned into the expression vector pCXND3 to construct expression vectors. These vectors were introduced into CHO-DG44 cells, and thus cell lines stably expressing the DNA fragments were prepared. Specifically, the expression vectors (20 µg) were combined with 0.75 ml of CHO-DG44 cells (1×10$^7$ cells/ml) suspended in PBS. The resulting mixtures were cooled on ice for 10 minutes, and transferred into cuvettes. The mixtures were then pulsed at 1.5 kV and 25 µFD using Gene Pulser Xcell (BioRad). After 10 minutes of recovery at room temperature, the cells treated by electroporation were added to CHO-S-SFMII medium (Invitrogen) containing 500 µg/ml Geneticin (Invitrogen). Then, v1-producing CHO cell line and v3-producing CHO cell line were established through selection.

Figure 19:
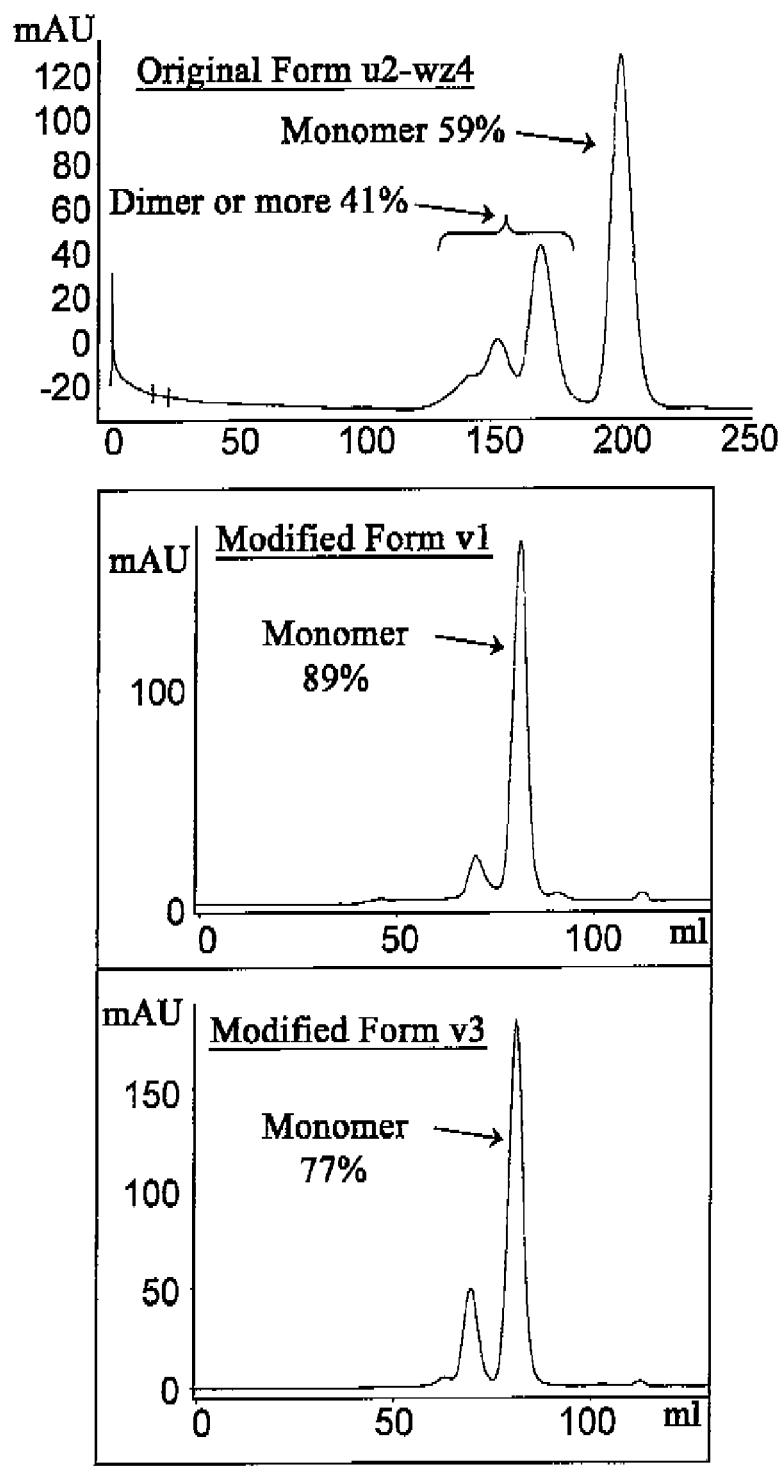
FIG. 19 shows results of gel filtration chromatography of u2-wz4, and the modified forms v1 and v3

The VH/VL contact surface-modified sc(Fv)2 type are not Flag-tagged. Thus, the antibodies were purified from culture supernatants using a fusion protein of GST with MG10 (Gln213 to Ala231 in the amino acid sequence of human Mpl) which is an epitope recognized by VB22B sc(Fv)2. The MG10-GST fusion protein was purified using Glutathione Sepharose 4B (Amersham Biosciences) according to the manufacturer's protocol. Furthermore, an affinity column was prepared by immobilizing the purified MG10-GST fusion protein onto HiTrap NHS-activated HP (Amersham Biosciences) according to the manufacturer's protocol. A culture supernatant of v1-expressing CHO cell line or v3-expressing CHO cell line was loaded onto MG10-GST fusion protein-immobilized column to adsorb v1 or v3. Elution was carried out using 100 mM Glycine-HCl (pH 3.5)/0.01% Tween80. The elution fractions were immediately neutralized with 1 M Tris-HCl (pH 7.4). The monomer molecules was purified by gel filtration chromatography using HiLoad 16/60 Superdex200 pg (Amersham Biosciences). The buffer used in the gel filtration chromatography was 20 mM citrate buffer (pH 7.5)/300 mM NaCl/0.01% Tween 80. The result of gel filtration chromatography shown in FIG. 19 revealed that, modified forms v1 and v3 in culture supernatants has a decreased proportion of aggregates that we dimer or higher multimers. However, the monomer ratios for v1 (89%) and v3 (77%) were increased in comparison with that of u2-wz4 before modification (59%). The modification of Amino acids on the VH/VL contact surface in the modified forms of v1 and v3 are inferred to have inhibited unfavorable association due to the electrostatic repulsion and enhanced favorable association. As described above, the inventors succeeded in efficiently expressing monomer molecules by controlling the association.

5-2. Analysis and Identification of Structural Isomers of Modified VH/VL Contact Surface sc(Fv)2 Type The obtained modified VH/VL contact surface form, v1 and v3, and the original form u2-wz4 were analyzed for the abundance ratio of the structural isomers by cation exchange chromatography and isoelectrofocusing. Furthermore, structural identification was carried out using the protease-based limited proteolysis method.

Cation exchange chromatography was performed as described below.
Column: TSK-gel Bioassist S; 4.6 mmϕ×50 mm (TOSOH)
Flow rate: 0.8 ml/min
Detection wavelength: 220 nm
Elution conditions:
Eluent A: 20 mmol/l Phosphate buffer (pH 7.0)
Eluent B: 20 mmol/l Phosphate buffer/500 mmol/l NaCl (pH 7.0) Gradient:

| Time (min) | B % |
|---|---|
| 0 | 0 |
| 5 | 0 |
| 25 | 30 |
| 25.1 | 100 |
| 35 | 100 |
| 35.1 | 0 |

Isoelectric focusing was carried out as described below. PhastGel Dry IEF gel (Amersham Biosciences) was swollen in the gel swelling buffer described below for 30 minutes or longer. Samples were added to the pre-swollen gel, and electrophoresed using PhastSystem under the following electrophoresis conditions. After electrophoresis, the gel was soaked in 20% TCA solution for 30 minutes, and then washed three times or more with milliQ water, for 5 minutes each. The gel was stained by Coomassie or silver staining depending on the protein concentrations of the samples. Coomassie staining was carried out using 0.02% CBB containing 0.1% $CuSO_4$ (w/v) as the s g solution, and de-staining was carried out using 30% methanol containing 10% acetic acid. Silver staining was carried out using Silver Stain kit, Protein (Amersham Biosciences) according to the standard protocol appended to the kit.

| <Gel swelling solution> | |
|---|---|
| Pharmalyte 8.5-10 | 80 μl |
| Biolyte 7-9 | 10 μl |
| Biolyte 3-9 | 10 μl |
| 20% Glycerol | 2.0 ml |

| <Electrophoresis program> | | | | | |
|---|---|---|---|---|---|
| SAMPLE APPLICATION DOWN AT step2 | | | | | 0 Vh |
| SAMPLE APPLICATION UP AT step3 | | | | | 0 Vh |
| Step 1 | 2000 V | 2.5 mA | 3.5 W | 15° C. | 75 Vh |
| Step 2 | 200 V | 2.5 mA | 3.5 W | 15° C. | 15 Vh |
| Step 3 | 2000 V | 2.5 mA | 3.5 W | 15° C. | 410 Vh |

Figure 20:
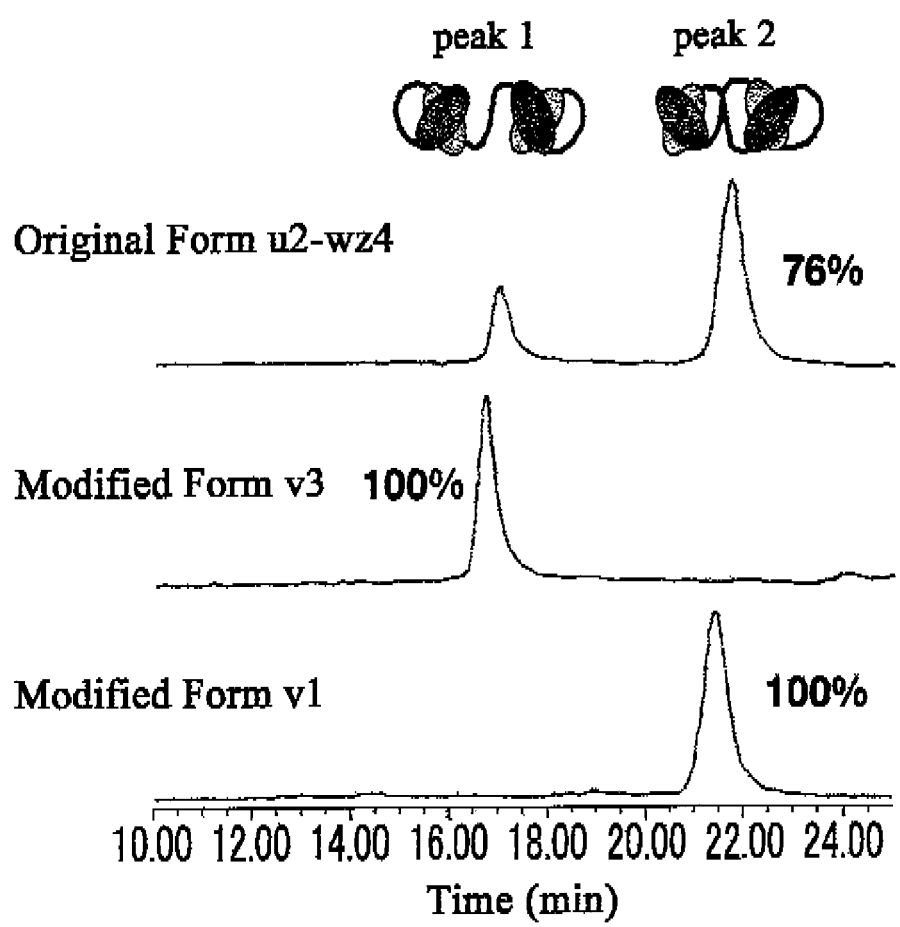
FIG. 20 shows results of cation exchange chromatography of u2-wz4, and the modified forms v1 and v3.
Figure 21:
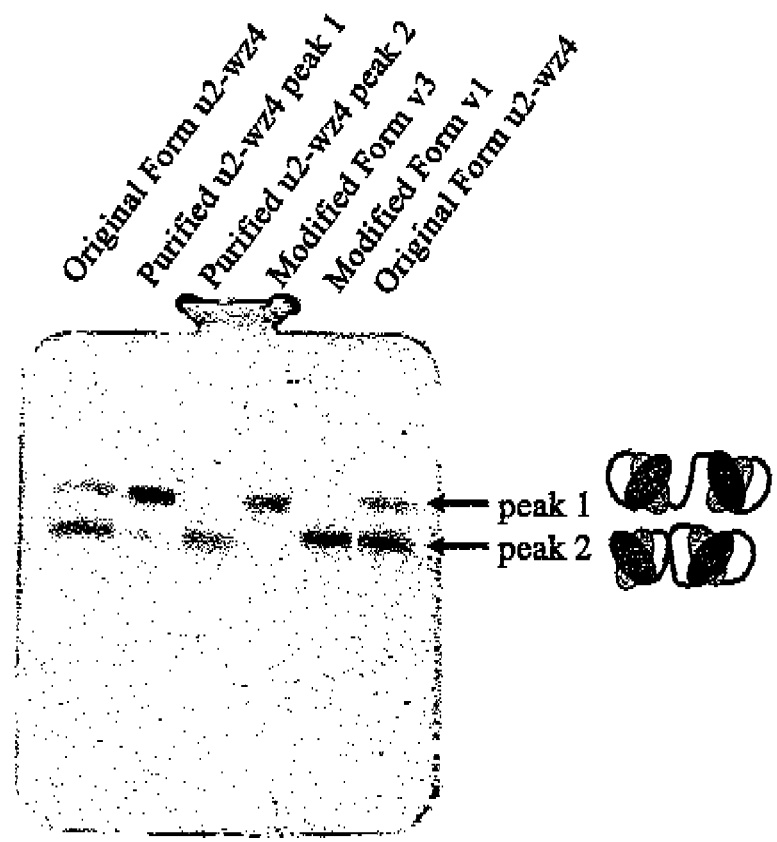
FIG. 21 is a photograph presenting results of isoelectric focusing of u2-wz4, purified u2-wz4 peak 1 and peak 2, and the modified forms v1 and v3.
Figure 22:
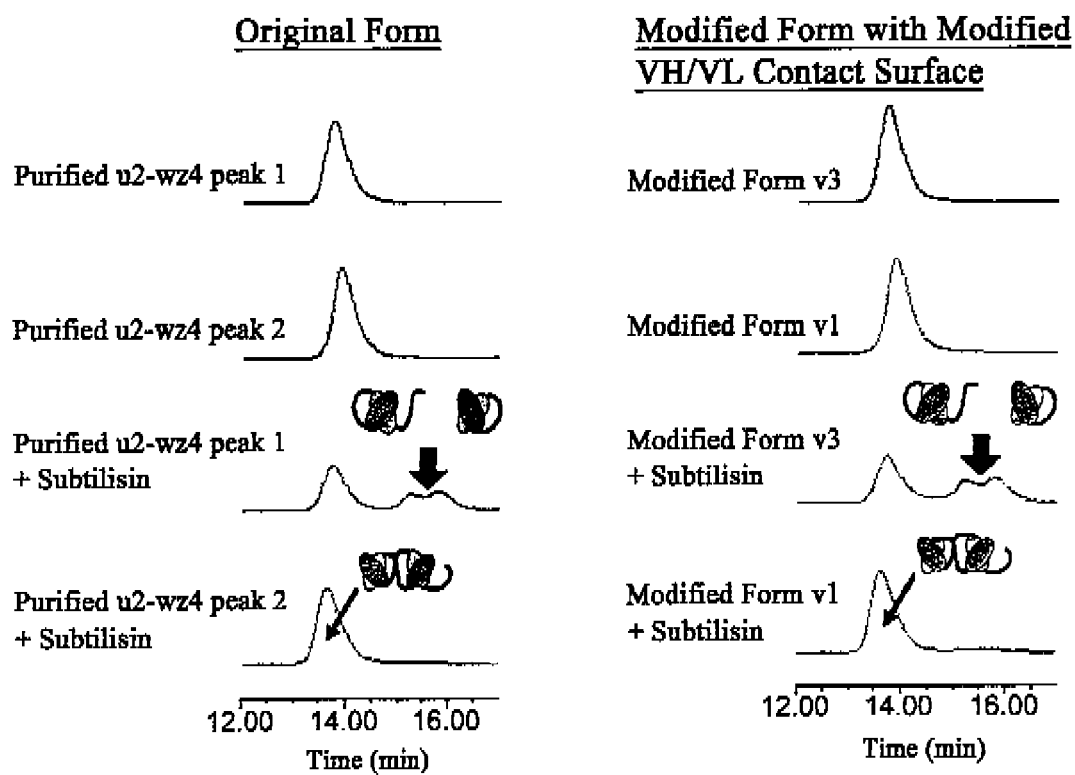
FIG. 22 shows results of gel filtration chromatography analysis of purified u2-wz4 peak 1 and peak 2, and the modified forms v1 and v3 after limited proteolysis using protease.

The structural identification using protease-based limited proteolysis method was performed under the condition indicated below. Each of purified u2-wz4 peak 1 and peak 2, and modified forms v1 and v3 was reacted with subtilisin A under the following conditions:

20 mM sodium citrate, 150 mM NaCl, pH 7.5
hVB22B u2-wz4 sc(Fv)2 peak 1 or peak 2: 0.15 mg/ml
Subtilisin A: 10 μg/ml
37° C., 30 nm The resulting reaction solution was analyzed by gel filtration chromatography under the following conditions:
Column: TSKgel Super2000sw (TOSOH)
Eluent: 50 mM sodium phosphate, 300 mM KCl, pH 7.0
Flow rate: 0.2 ml/min
Detection: 220 nm The results of analyses of structural isomers using cation exchange chromatography and isoelectric focusing, which are shown in FIGS. 20 and 21, revealed that 100% of the modified form v1 was expressed as a structural isomer of the single chain diabody type and 100% of the modified form v3 was expressed as a structural isomer of the bivalent scFv type whereas u2-wz4 expressed a mixture of the two structural isomers which contain bivalent scFv type (24%) and single chain diabody (76%). As shown in FIG. 22, the result of protease-based limited proteolysis also revealed that alike purified u2-wz4 peak 1, the modified form v3 gave a low molecular weight antibody peak whereas modified form v1 gave no low molecular weight antibody peak as in the purified u2-wz4 peak 2. This shows that modified form v1 is expressed as a structural isomer of the single chain diabody type while modified form v3 is expressed as a structural isomer of the bivalent scFv type.

Example 6

Activity Assay and Stability Assay of the VH/VL Contact Surface-Modified sc(Fv)2

6-1. Biological Activity Assay of sc(Fv)2 with Modified VH/VL Contact Surface

Forms v1 and v3 with modified VH/VL contact surface were assayed for their agonistic activity by the method shown in Example 1. The agonistic activity was markedly different between the structural isomers. As shown in FIG. 11, peak 2 with the single chain diabody structure exhibited very high agonistic activity while the activity of peak 1 with the bivalent scFv structure was extremely low. As shown in FIG. 23, the activity of modified form v1 was comparable to that of peak 2 and the activity of modified form v3 was comparable to that of peak 1. This finding in terms of the biological activity also demonstrates that the modified form v1 has a single chain diabody structure, and the modified form v3 has a bivalent scFv structure.

6-2. Stability Assay of sc(Fv)2 with Modified VH/VL Contact Surface

To evaluate the stability of purified u2-wz4 peak 1 and peak 2, and the modified forms v1 and v3, denaturation temperature (Tm) was measured by differential scanning calorimetry under the following conditions:
DSC: N-DSCII (Applied Thermodynamics)
Solution: 20 mM sodium citrate, 300 mM NaCl, pH 7.0
Protein concentration: 0.1 mg/ml
Scanning speed: 1° C./min Results of each DSC measurement are shown in FIG. 24. Tm values of the purified u2-wz4 peak 2 and the modified form v1 are comparable to that of the original form, suggesting that their stabilities are comparable to each other. The stability of the modified form v3 was slightly lower than that of purified u2-wz4 peak 1. It has been reported that regulating the contact surface by methods using knobs-into-hole technology markedly lowers the Tm value, thereby reducing the stability (Acta Pharmacologica Sinica, 2005, 26, 649-658). For example, Tm value of the original CH3 domain is 80.4° C. when using this method, while Tm of the modified CH3 domain is 69.4° C. in heterologous association of CH3 domain of IgG. In contrast, the present invention allowed regulation of the association without reducing the stability.

Next the stability of purified u2-wz4 peak 1 and peak 2, and the modified form v1 and v3 with modified VH/VL contact surface, were evaluated by heat acceleration test under the following conditions.

<Conditions of Heat Acceleration>
Solution: 20 mM sodium citrate, pH 6.0
Protein concentration: 0.25 mg/ml
Acceleration condition: 40° C.-6 days, 12 days
Samples treated by heat acceleration were analyzed by gel filtration chromatography and cation exchange chromatography under the conditions described below.

Figure 25:
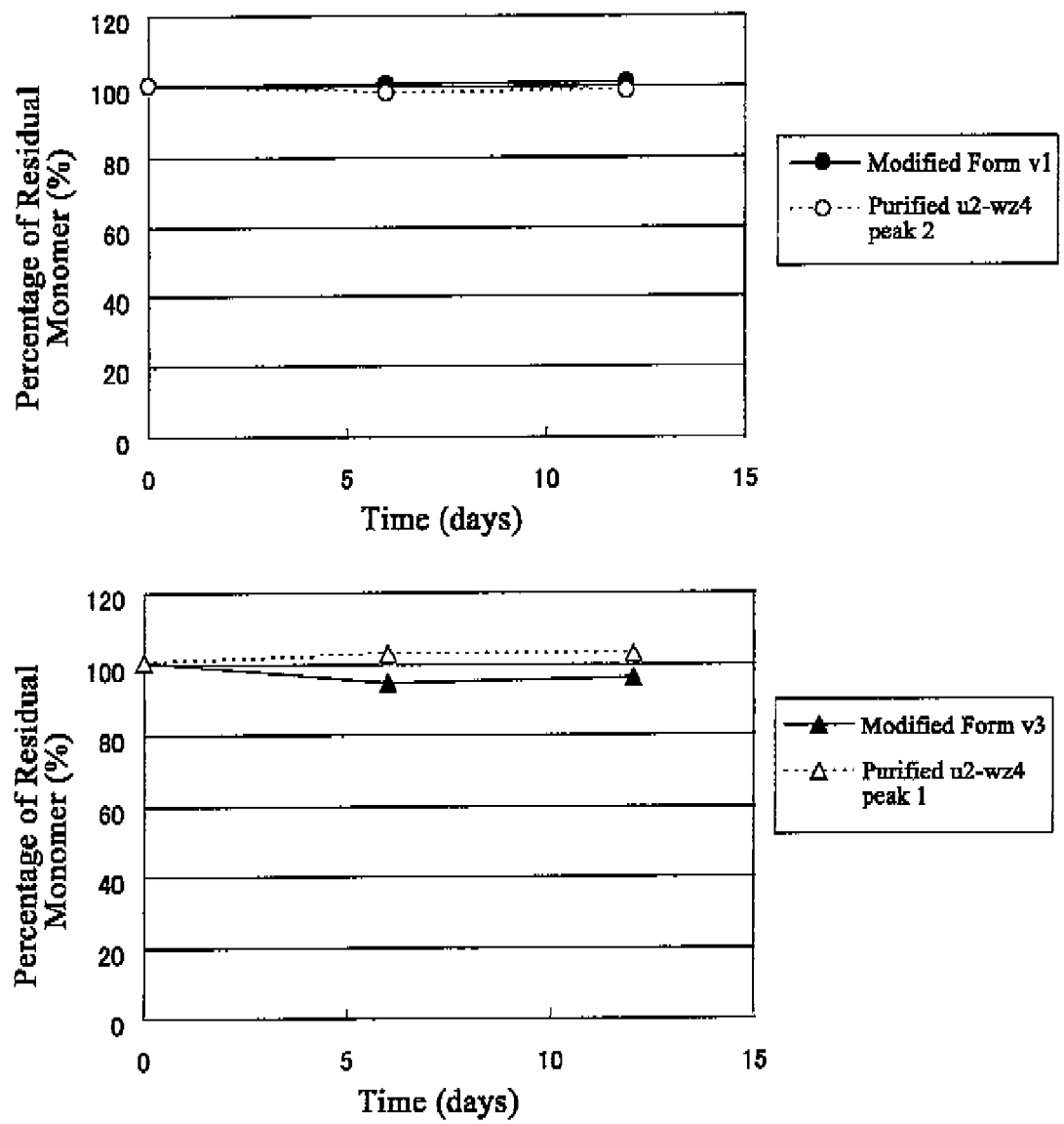
FIG. 25 shows results of gel filtration chromatography analysis in the heat accelerated test of purified u2-wz4 peak 1 and peak 2, and the modified forms v1 and v3.

As shown in FIG. 25, the result of gel filtration chromatography analysis confirmed that the percentages of residual monomer were comparable between purified u2-wz4 peak 2 and the modified form v1, and thus the stability in association was comparable between the two. Furthermore, the percentage of residual monomer was almost the same between the purified u2-wz4 peak 1 and the modified form v3, confirming that the association stability is comparable between the two structural isomers.

Figure 26:
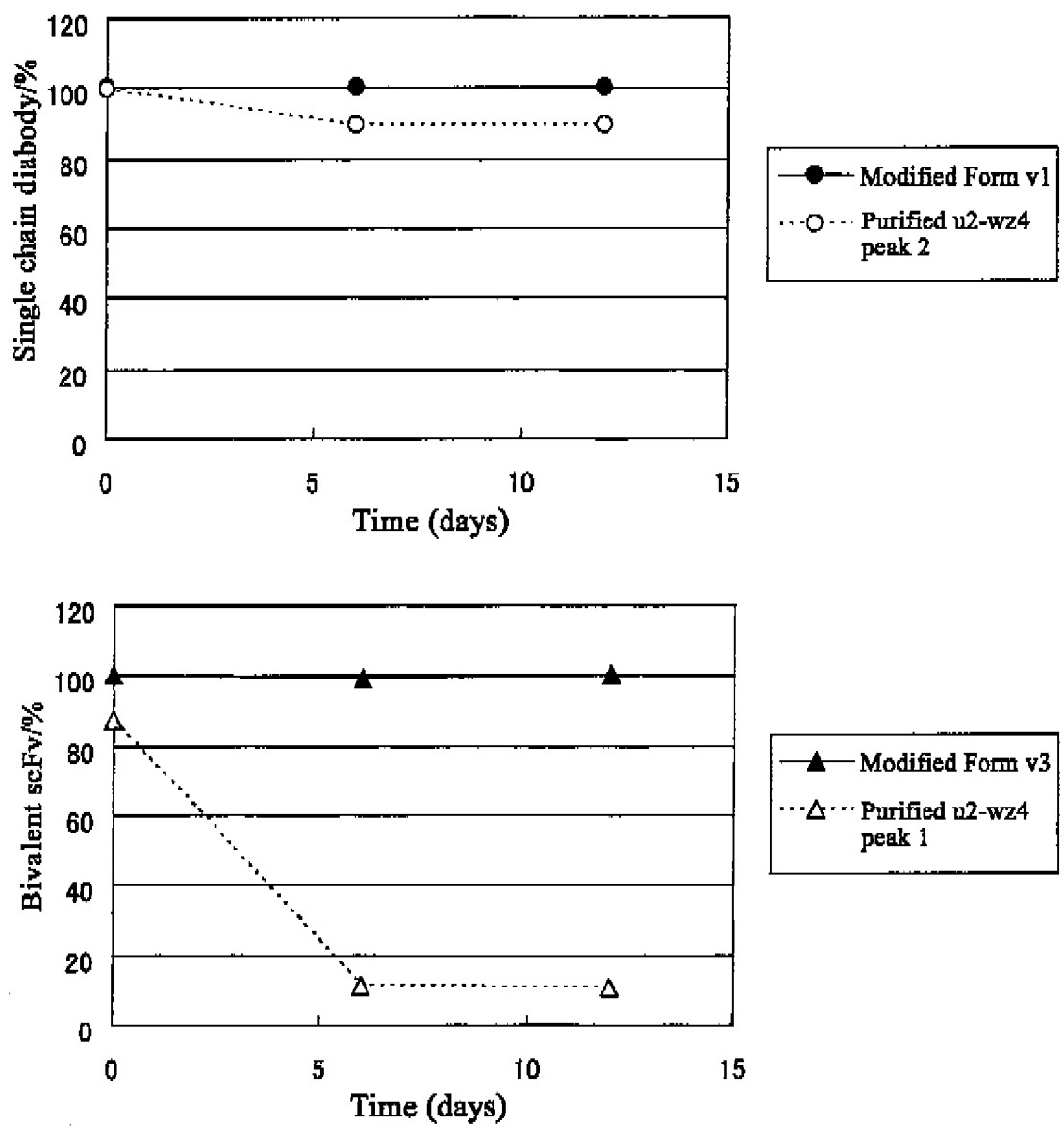
FIG. 26 shows results of cation exchange chromatography in the heat accelerated test of purified u2-wz4 peak 1 and peak 2, and the modified forms v1 and v3.

As shown in FIG. 26, the result of cation exchange chromatography analysis showed that neither form v1 nor form v3 with modified VH/VL contact surface has undergone isomerization even after heating acceleration. In contrast, purified peak 1 of the original form isomerized to peak 2 and purified peak 2 of the original form isomerized to peak 1 through isomerization reaction. It was found that in addition to allowing expression of only one of the two types of structural isomers at 100%, each obtained structural isomer can be stably preserved without isomerization, by applying the modification of the VH/VL contact surface.

In this example, it was found that only one of the two types of structural isomers can be expressed at the rate of 100% through such modification of VH/VL contact surface applied for v1 and v3. As for controlling the VH/VL contact surface to obtain single chain antibodies having the desired structure, method for controlling the structure of bispecific diabodies using knobs-into-hole technology (Protein Sci. 1997 Apr. 6(4):781-8, Remodeling domain interfaces to enhance heterodimer formation., Zhu Z, Presta L G; Zapata C, Carter P.) is known. This method reports that the rate of formation of the target heterodimer structure increased from 72% to up to 92% through modification of a total of four amino acids per VB4L contact surface. Meanwhile, the present invention succeeded in obtaining desired structures at the rate of 100% without reducing thermal stability and stability of the structural isomers by modifying four amino acids (two amino acids per VH/VL contact surface).

Example 7

Separation of Structural Isomers of Humanized Anti-Human IL-6 Receptor Antibody sc(Fv)2 and Identification of their Structures 7-1. Preparation of Humanized Anti-Human IL-6 Receptor Antibody sc(Fv)2

An sc(Fv)2 gene (the amino acid sequence, SEQ ID NO, 18; the nucleotide sequence, SEQ ID NO: 19) having the arrangement of VH-linker sequence-VL-linker sequence-VH-linker sequence-VL was linked using a gene encoding the linker sequence (GlyGlyGlyGlySer)×3 (SEQ ID NO: 1) was prepared using the VH and VL of humanized anti-human IL-6 receptor antibody reported by Sato K. et al. (Cancer Research (1993) 53:851-856). The obtained gene was inserted into the expression vector pMCDN to express the gene in animal cells. The vector construction procedure for the vector pMCDN is described below. The enhancer and promoter of mouse cytomegalovirus (mCMV), and the late polyadenylation site of simian virus 40 (SV40) were inserted into vector pUC19 and was named pMC. Next, DBFR-ΔE-rVH-PM1-f (see WO 92/19759) was digested at EcoRI and SmaI restriction sites to separate the antibody H chain gene from the vector. After recovery of the vector alone, an EcoRI-NotI-BamHI adaptor (Takara Shuzo Co. Ltd.) was cloned into the vector. This vector was named pCHOI. The DBFR gene expressing region of pCHOI and the expression region of the Neomycin resistance gene of pCXN (Niwa et al., Gene (1991) 108: 193-200) were inserted into the pMC vector. This vector was named pMCDN. The constructed expression vector for the humanized anti-human IL-6 receptor antibody sc(Fv)2 was linearized using restriction enzymes, and then introduced into CHO-DG44 cells by gene transfer. Thus, an antibody-expressing cell line was established.

The cell line stably expressing the antibody was prepared by the procedure described below. Gene transfer to cells was achieved by electroporation using GenePulserXcell (Bio-Rad). Each antibody expression vector was mixed with 0.75 ml of CHO cells suspended in PBS (1×10$^7$ cell/ml). After being cooled on ice for 10 minutes, the mixtures were transferred into cuvettes and then pulsed at 1.5 kV and 25 μFD. After 10 minutes of recovery at room temperature, the cells treated by electroporation were suspended in 40 ml of CHO-S-SFMII medium (Invitrogen) supplemented with 1×HT supplement (Invitrogen). The cell suspensions were diluted 10 to 50 times with the same medium, and the resulting dilutes were aliquoted at 100 μl/well into wells of 96-well culture plates. The cells were incubated in a $CO_2$ incubator (5% $CO_2$) for 24 hours, and then Geneticin (Invitrogen) was added at a concentration of 0.5 mg/ml. The cells were then cultured for 2 weeks. Colonies of drug resistant transformant cells were successively scaled-up, and the high-producing cell lines established were cultured on a large scale to obtain culture supernatants.

Utilizing the fact that the L chain of humanized anti-human IL-6 receptor antibody binds to Protein L, culture supernatants of CHO cells expressing the humanized anti-human IL-6 receptor antibody sc(Fv)2 were loaded onto a column filled with Protein L (Actigen) to adsorb the humanized anti-human L-6 receptor antibody sc(Fv)2. The antibody was eluted with 100 mM Glycine-HCl (pH 2.7). The eluted fractions were immediately neutralized with 1 M Tris-HCl (pH 8.5), and loaded onto a HiLoad 26/60 Superdex 200 pg (Amersham Biosciences) column for gel filtration chromatography. Dulbecco PBS was used in the gel filtration chromatography.

7-2. Separation and Purification of the Structural Isomers of Humanized Anti-Human IL-6 Receptor Antibody sc(Fv)2

The humanized anti-human IL-6 receptor antibody sc(Fv)2 is an sc(Fv)2 comprising the sequence of $VH_1$-linker-$VL_2$-linker-$VH_3$-linker-$VL_4$. Therefore, as is the case of VB2213 in Example 1 and hVB22B in Example 2, depending on the combinations of Fv (a molecule in which VH and VL are non covalently linked), there would be two types of structural isomers of sc(Fv)2: the bivalent scFv type in which each set of $VH_1$ and $VL_2$, and $VH_3$ and $VL_4$ form a Fv; and the single chain diabody type in which each set of $VH_1$ and $VL_4$, and $VH_2$ and $VL_3$ (FIG. 1) form a Fv. The inventors investigated the separation of the structural isomers of humanized anti-human IL-6 receptor antibody sc(Fv)2, and as a result succeeded in separating the structural isomers of humanized anti-human IL-6 receptor antibody sc(Fv)2 by cation exchange chromatography using BioAssist S (TOSOH) under the following elution conditions.

<Elution Conditions>
Mobile phase: 20 mM Tris-HCl, pH 8.5, 75 mM NaCl
Flow rate: 0.8 ml/min
Gradient: isocratic (without gradient)

Figure 27:
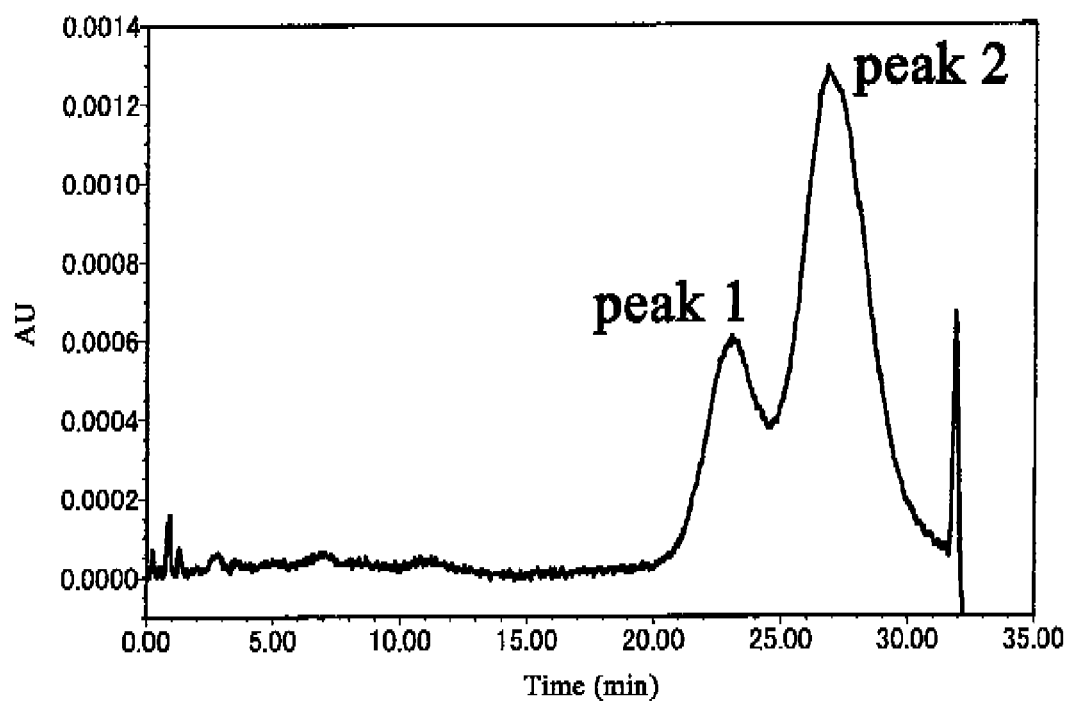
FIG. 27 shows results of separation of peak 1 and peak 2 of humanized anti-human IL-6 receptor antibody sc(Fv)2 using cation exchange chromatography.
Figure 28:
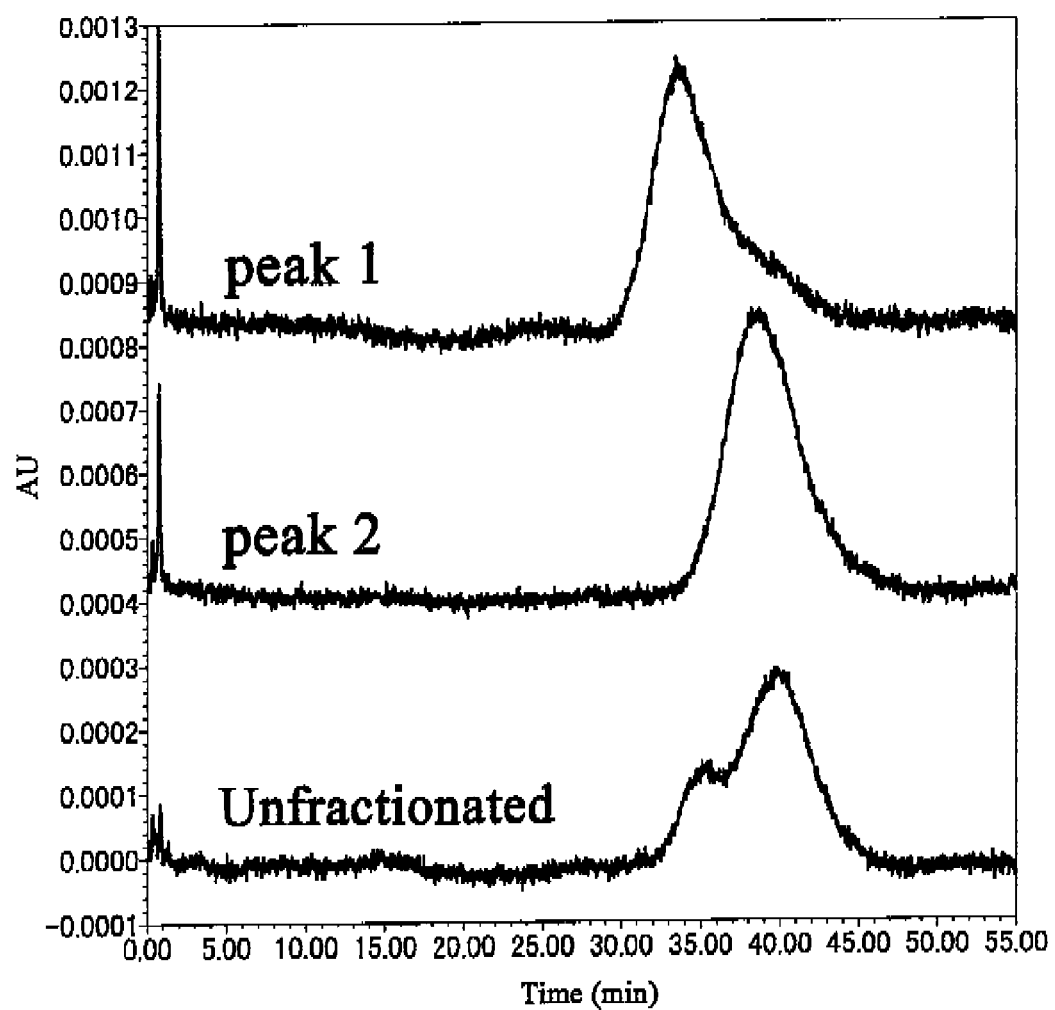
FIG. 28 shows results of cation exchange chromatography analysis of purified peak 1 and peak 2 of humanized anti-human IL-6 receptor antibody sc(Fv)2.

Under the conditions described above, the hazed anti-human IL-6 receptor antibody sc(Fv)2 was separated into two peaks. The chromatogram shown in FIG. 27 was obtained. The peaks with short and long retention time were named peak 1 and peak 2, respectively, Peak 1 and peak 2 can be purified by the method described above. The result of cation exchange chromatography analysis of purified peak 1 and peak 2 is shown in FIG. 28.

7-3. Identification of Structural Isomers of Humanized Anti-Human IL-6 Receptor Antibody sc(Fv)2

Figure 29:
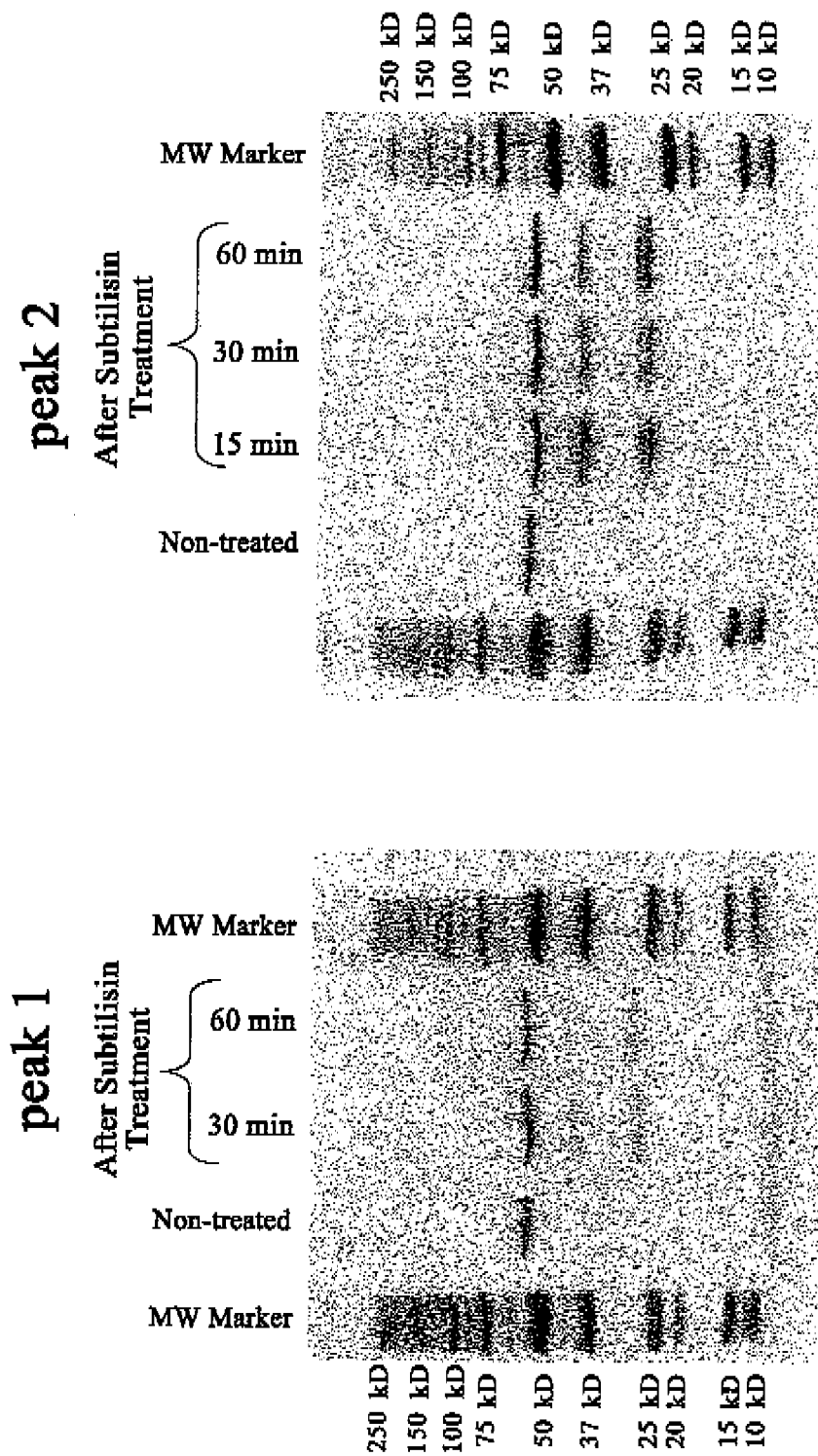
FIG. 29 shows results of reducing SDS-PAGE of peak 1 and peak 2 of humanized anti-human IL-6 receptor antibody sc(Fv)2 after subtilisin treatment. Putative structures of the obtained bands are given on the right.
Figure 30:
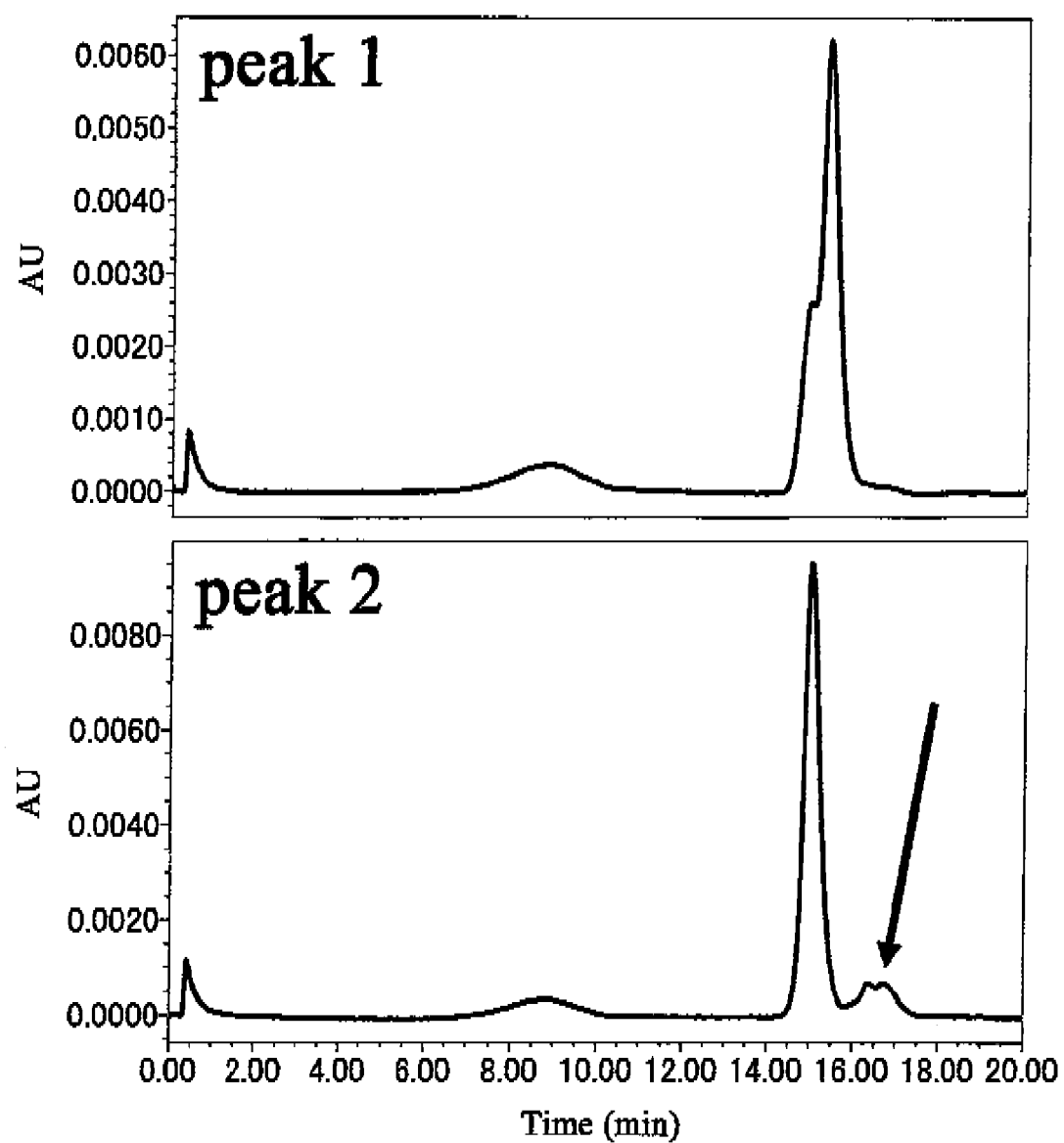
FIG. 30 shows results of gel filtration chromatography after limited proteolysis of peak 1 and peak 2 of humanized anti-human IL-6 receptor antibody sc(Fv)2 with subtilisin. The elution position of the low molecular weight antibody peak is indicated by an arrow.

Since the fractionated Peak 1 and peak 2 of the humanized anti-human IL-6 receptor antibody sc(Fv)2, were considered to be structural isomers, the same protease-based limited proteolysis method as used in Examples, 1, 2, and 3 was used as an analytical method for identifying the two types of structural isomers. Peak 1 and peak 2 of the humanized anti-human IL-6 receptor antibody sc(Fv)2 were reacted with Subtilisin under the following conditions:
PBS (pH 7.4)
humanized anti-human IL-6 receptor antibody sc(Fv)2 peak 1 or peak 2: 0.05 mg/ml
Subtilisin A: 0.5 µg/ml
37° C., 60 min Following the incubation described above, reducing SDS-PAGE was carried out using 12.5% Phastgel Homogeneous. According to the result, peak 1 and peak 2 both showed the same band pattern, as shown in FIG. 29. Peak 1 and peak 2 after partial linker cleavage under the reaction condition described above were analyzed by gel filtration chromatography using TSK Super2000 (TOSOH) under the following conditions:
Mobile phase: 50 mM sodium phosphate, 300 mM KCl, pH 7.0
Flow rate: 0.2 ml/min As shown in FIG. 30, the result showed that peak 1 gave no low molecular weight antibody peak, while peak 2 did (a low molecular weight antibody peak of about one half of the original molecular weight). According to the result described above, peak 1 and peak 2 were thus identified as the single chain diabody and bivalent scFv types, respectively. FIG. 27 indicates that the content of peak 2 is greater than that of peak 1 in the humanized anti-human IL-6 receptor antibody sc(Fv)2, and therefore the bivalent scFv type is the major component and the single chain diabody type is the minor component in the humanized anti-human IL-6 receptor antibody sc(Fv)2. In VB2213 sc(Fv)2 of Example 1 and hVB22B u2-wz4 sc(Fv)2 of Example 2, the single chain diabody type was the major component. Separating structural isomers and identifying their structures would be important when sc(Fv)2s are developed as pharmaceuticals, because the content ratio of a structural isomer greatly varies depending on the differences in the sequences of variable regions in sc(Fv)2.

Example 8

Activity Assay of the Structural Isomers of Humanized Anti-Human IL-6 Receptor Antibody sc(Fv)2

8-1. Establishment of BaF3 Cell Line Coexpressing Human gp130-Expressing BaF3 Cell Line and Human gp130/Human IL-6 Receptor As described below, a human gp130-expressing BaF3 cell line was established to obtain a cell line that proliferates in an IL-6 dependent manner.

A full-length human gp130 cDNA (Hibi et al, Cell (1990) 63: 1149-1157 (GenBank Accession No. NM_002184)) was amplified by PCR, and cloned into the expression vector pCOS2Zeo to construct pCOS2Zeo/gp130. The expression vector pCOS2Zeo was constructed by removing the DHFR gene expressing region from pCHOI (Hirata et al., FEBS Letter (1994) 356:244-248) and the expression region of Zeocin resistance gene was inserted.

Ten µg of pCOS2Zeo/gp130 was mixed with BaF3 cells ($0.8 \times 10^7$ cells) suspended in PBS, and the mixture was pulsed at 0.33 kV and 950 µFD using Gene Pulser (Bio-Rad). BaF3 cells treated by electroporation for gene transfer were cultured in RPMI1640 medium (Invitrogen) including 0.2 ng/ml mouse interleukin-3 (Peprotech) and 10% Fetal Bovine Serum (hereinafter abbreviated as FBS; HyClone) for a day ad night. RPMI1640 medium containing 100 ng/ml human interleukin 6 (R&D), 100 ng/ml soluble human interleukin 6 receptor (R&D systems), and 10% FBS was added for selection. Thus, a human gp130-expressing BaF3 cell line (hereinafter abbreviated as BaF3/gp130) was established.

8-2. Human IL-6-Neutralization Activity Assay of the Structural Isomers of Humanized Anti-Human IL-6 Receptor Antibody sc(Fv) 2

IL-6-neutralization activity was assayed as described below using BaF3/gp130 that proliferates in an IL-6 dependent manner. Purified structural isomers of humanized anti-human IL-6 receptor antibody sc(Fv)2 were diluted to 10 µg/ml using RPMI1640 containing 10% FBS. A 3-fold dilution series (3, 6, 9, 12, 15 and 18 times), were prepared using each of these solutions, and a 50-µl aliquot was added to each well of 96-well plates (FALCON). Next, BaF3/gp130 were washed three times with RPMI1640 medium containing 10% FBS (HyClone), and then suspended at $5 \times 10^4$ cells/ml in RPMI1640 medium including 60 ng/ml human interleukin-6 (R&D systems), 60 ng/ml soluble human IL-6 receptor (a preparation of the inventors company), and 10% FBS. A 50-µl aliquot of these was added to the antibody sample in each well. The soluble human IL-6 receptor was prepared by the procedure described below. A gene encoding the amino acids from position 1 to 344 of soluble human IL-6 receptor (Yamasaki et al., Science (1988) 241: 825-828 (GenBank No.X12830)) was introduced into CHO cells, and then the receptor was purified from the culture supernatants for preparation.

After 72 hours of culturing at 37° C. and with 5% $CO_2$, 20 µl of WST-8 reagent (Cell Counting Kit-S; DOJINDO LABORATORIES) diluted two folds with PBS was added to each well. Immediately after that, absorbance at 450 nm (reference wavelength: 620 nm) was measured using SUNRISE CLASSIC (TECAN). After two hours of culture, absorbance at 450 nm (reference wavelength: 620 nm) was measured again and the IL-6 neutralization activity was evaluated using the absorbance change during the two hours as an index.

Figure 31:
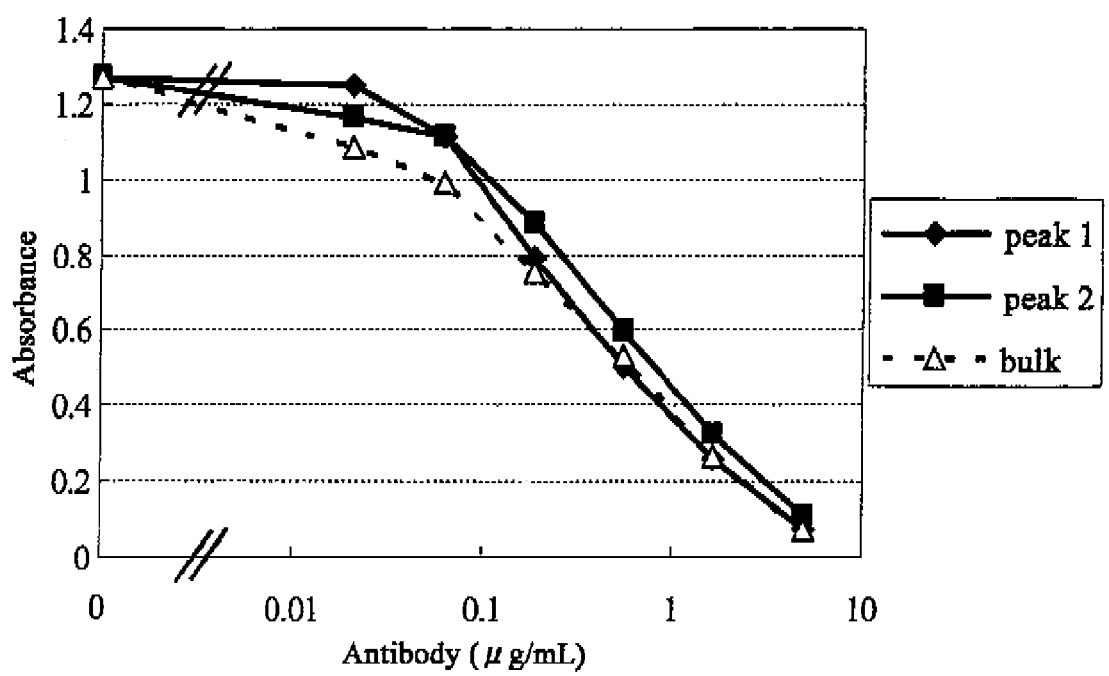
FIG. 31 shows results of IL-6-neutralizing activity assay for peak 1 and peak 2 of humanized anti-human IL-6 receptor antibody sc(Fv)2 in BaF3/gp130.

As shown in FIG. 31, the neutralization activities of the structural isomers (peak 1 and peak 2) of humanized anti-human IL-6 receptor antibody sc(Fv)2 were comparable to those of the purified samples (bulk) before fractionation. The activity was found to be markedly different between the two types of structural isomers of VB22B sc(Fv)2 in Example 1 and the same of hVB22B sc(Fv)2 in Example 2. There was no difference in the neutralization activity between the two types of isomers of the humanized anti-human IL-6 receptor antibody sc(Fv)2 of this present Example. Thus, the activity difference between the two types of structural isomers of sc(Fv)2 would vary depending on the type of target antigen and the amino acid sequence of the sc(Fv)2 molecule. For this reason, to develop sc(Fv)2 molecules as pharmaceuticals, separation of the structural isomers, structural identification, and regulation of the structural isomers are considered important. As described in Example 6, each structural isomer can undergo isomerization during storage. Therefore, separation and identification of the structural isomers, and regulation of the structural isomers are also important from the view point of quality standardization of sc(Fv)2 preparations.

Example 9

Method for Obtaining Single Chain Diabody of VB22B sc(Fv)2 with a High Yield

Figure 32:
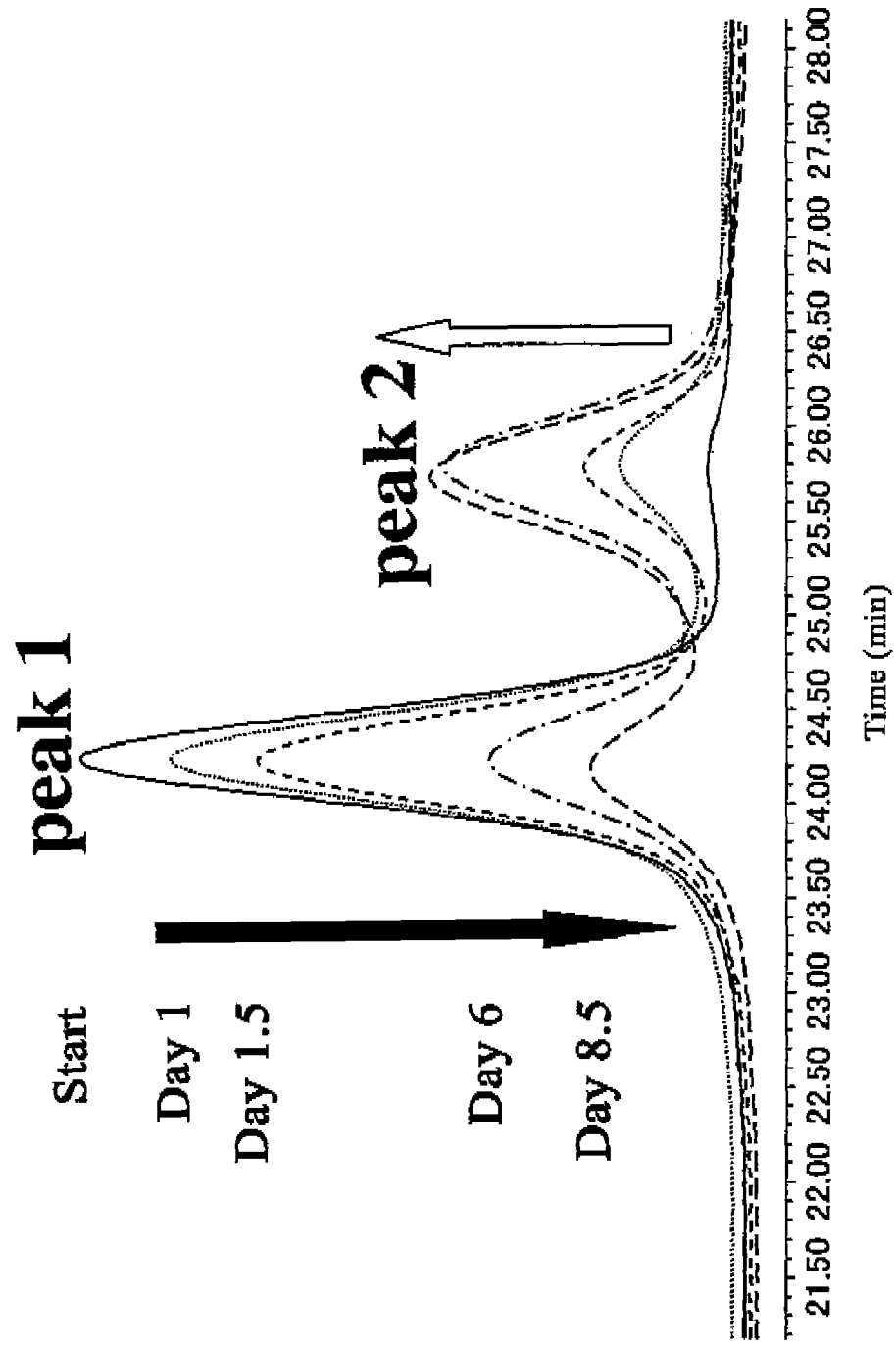
FIG. 32 shows a chronological increase of peak 2 in anion exchange chromatography analysis using samples of VB223 sc(Fv)2 peak 1 incubated in 20 mM sodium acetate/150 mM NaCl (pH 6.0) at 40° C.
Figure 33:
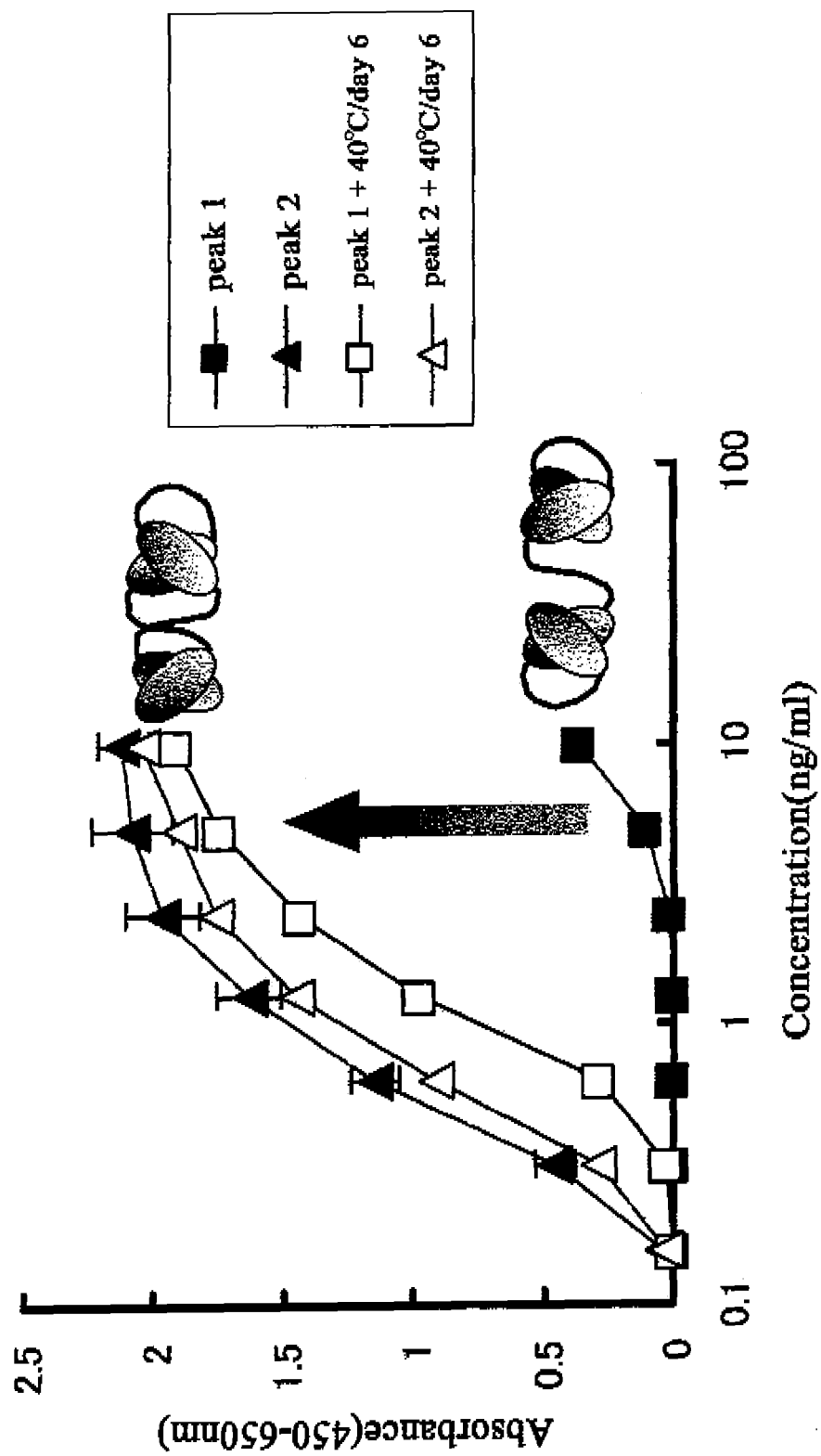
FIG. 33 shows a graph assaying the agonistic activity of peak 1 and peak 2 of VB22B sc(Fv)2, and the samples incubated at 40° C. for 6 days. The graph also confirms activity increase by isomerization of peak 1 to peak 2.

Each of the single chain diabody (peak 2) and bivalent scFv (peak 1) purified from VB22B sc(Fv)2 was incubated at 40° C. with the conditions of 20 mM sodium acetate/150 mM NaCl (pH 6.0). The ratio of peak 1 and peak 2 was determined by the anion exchange chromatography method described in Example 1. The result showed that the peak area of peak 1 decreased, and in turn the peak area of peak 2 increased, as shown in FIG. 32. The agonistic activity of the sample prepared by incubating peak 1 for 6 days under the same condition was assayed by the method described in Example 1. As shown in FIG. 33, the agonistic activity drastically increased as compared to the sample before incubation. As described in Example 1, the activity of peak 1 was significantly lower than that of the single chain diabody peak 2. Thus, the bivalent scFv peak 1 was found to undergo structure conversion (the structural isomer isomerizes) to become peak 2 of the single chain diabody with higher activity through incubation in 20 mM sodium acetate/150 mM NaCl (pH 6.0) at 40° C. Thus, the finding described above showed that the content ratio of peak 2 can be increased by exposing a mixture of the bivalent scFv and single chain diabody at appropriate conditions which allows the conversion of the bivalent scFv of peak1 into the single chain diabody of peak2. By using the method of isomerizing peak 1 to peak 2, the single chain diabody of peak 2 can be prepared with a high yield by isomerizing peak 1 to peak 2 in a mixture in which peak 1 and peak 2 had been produced by the cells.

Example 10

Figure 34:
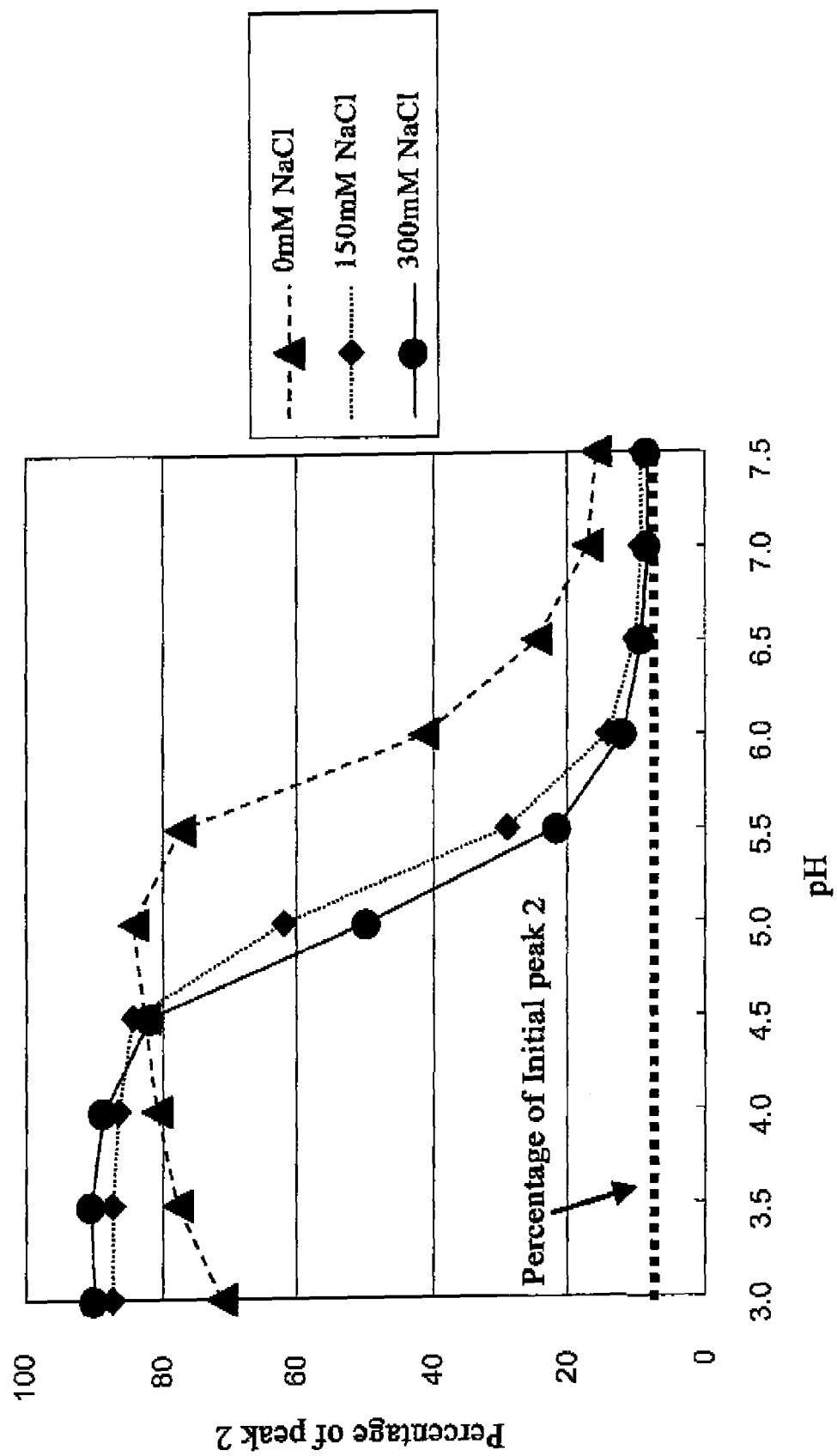
FIG. 34 shows isomerization of hVB22B u2-wz4 sc(Fv)2 peak 1 to peak 2 by incubating peak 1 at 25° C. for 10 days under various conditions.

Method for Obtaining Single Chain Diabody Type of hVB22B sc(Fv)2 with a High Yield The bivalent scFv (peak 1) purified from hVB22B u2-wz4 sc(Fv)2 in Example 4 was incubated at 25° C. for 10 days under 30 types of conditions in total: 20 mM sodium citrate, and 0, 150, or 300 mM NaCl at pH 3.0, 3.5, 4.0, 4.5, 5.0, 5.5, 6.0, 6.5, 7.0, or 7.5. The ratio of peak 1 and peak 2 was determined by the cation exchange chromatography method shown in Example 1. The result showed that the abundance ratio of peak 2 increased in comparison with that before incubation, as shown in FIG. 34. This finding showed that, in hVB22B u2-wz4 sc(Fv)2, the bivalent scFv of peak 1 was also structurally converted into the single chain diabody peak 2. The isomerization rate was found to become greater as pH and salt concentration decrease. By using the method of isomerizing peak 1 to peak 2, a high yield of single chain diabody of peak 2 can be obtained by isomerizing peak 1 to peak 2 in a mixture in which peak 1 to peak 2 had been produced by the cells.

INDUSTRIAL APPLICABILITY

The present invention provides methods for separating and obtaining the two types of structural isomers in sc(Fv)2 compositions, methods for identifying the structures of the separated two types of structural isomers, and methods for quantitatively analyzing the two types of structural isomers. The present invention also provides methods for increasing the percentage of a specific structural isomer in sc(Fv)2 compositions by adjusting linker lengths. The present invention further provides methods for controlling the formation of the structural isomers by modifying the amino acids in the variable regions. Use of these methods described above allows the production of pharmaceutical compositions comprising specific structural isomers of sc(Fv)2 as active ingredients and to provide pharmaceutical compositions with activity higher than previous compositions. Furthermore, the present invention enables the provision of sc(Fv)2s as pharmaceutical compositions, in which the structural isomer content ratio of the sc(Fv)2s has been controlled by standardization tests, which are essential in developing pharmaceuticals.

The invention claimed is:

1. A pharmaceutical composition comprising a monospecific sc(Fv)2 that comprises four variable regions V1 to V4 in order from amino terminus to carboxy terminus, a first peptide linker connecting variable regions V1 and V2, a second peptide linker connecting variable regions V2 and V3, and a third peptide linker connecting variable regions V3 and V4, wherein the length of each of the first, second, and third linkers is 15 to 30 amino acids, and wherein at least 90% of the sc(Fv)2 in the pharmaceutical composition is in the form of a single-chain diabody-type isomer, in which V1 is associated with V4 and V2 is associated with V3.

2. The pharmaceutical composition of claim 1, wherein the single-chain diabody-type isomer binds to a receptor.

3. The pharmaceutical composition of claim 1, wherein the single-chain diabody-type isomer has an agonistic activity.

4. The pharmaceutical composition of claim 1, wherein the first, second, and third linkers are each 15 amino acids in length.

5. A pharmaceutical composition comprising a monospecific sc(Fv)2 that comprises four variable regions V1 to V4 in order from amino terminus to carboxy terminus, a first peptide linker connecting variable regions V1 and V2, a second peptide linker connecting variable regions V2 and V3, and a third peptide linker connecting variable regions V3 and V4, wherein the length of each of the first, second, and third linkers is 15 to 30 amino acids, wherein at least 90% of the sc(Fv)2 in the pharmaceutical composition is in the form of a single-chain diabody-type isomer, in which V1 is associated with V4 and V2 is associated with V3, and wherein the single-chain diabody-type isomer of the sc(Fv)2 has greater activity than a bivalent scFv-type isomer of the sc(Fv)2.

6. The pharmaceutical composition of claim 5, wherein the single-chain diabody-type isomer binds to a receptor.

7. The pharmaceutical composition of claim 5, wherein the single-chain diabody-type isomer has an agonistic activity.

8. The pharmaceutical composition of claim 5, wherein the first, second, and third linkers are each 15 amino acids in length.

9. The pharmaceutical composition of claim 1, wherein at least 95% of the sc(Fv)2 in the pharmaceutical composition is in the form of the single-chain diabody-type isomer.

10. The pharmaceutical composition of claim 5, wherein at least 95% of the sc(Fv)2 in the pharmaceutical composition is in the form of the single-chain diabody-type isomer.

11. The pharmaceutical composition of claim 1, wherein the first, second, and third linkers are each 20 amino acids in length.

12. The pharmaceutical composition of claim 1, wherein the first, second, and third linkers are each 30 amino acids in length.

13. The pharmaceutical composition of claim 5, wherein the first, second, and third linkers are each 20 amino acids in length.

14. The pharmaceutical composition of claim 5, wherein the first, second, and third linkers are each 30 amino acids in length.

* * * * *

SEQUENCE LISTING

```
<160> NUMBER OF SEQ ID NOS: 21

<210> SEQ ID NO 1
<211> LENGTH: 15
<212> TYPE: PRT
<213> ORGANISM: Artificial
<220> FEATURE:
<223> OTHER INFORMATION: An artificially synthesized linker sequence

<400> SEQUENCE: 1

Gly Gly Gly Gly Ser Gly Gly Gly Gly Ser Gly Gly Gly Gly Ser
1               5                   10                  15
```

```
<210> SEQ ID NO 2
<211> LENGTH: 8
<212> TYPE: PRT
<213> ORGANISM: Artificial
<220> FEATURE:
<223> OTHER INFORMATION: An artificially synthesized flag sequence

<400> SEQUENCE: 2

Asp Tyr Lys Asp Asp Asp Asp Lys
1               5

<210> SEQ ID NO 3
<211> LENGTH: 1572
<212> TYPE: DNA
<213> ORGANISM: Mus musculus

<400> SEQUENCE: 3
atggaatggc ctttgatctt tctcttcctc ctgtcaggaa ctgcaggtgt ccactcccag      60
gttcagctgc agcagtctgg acctgagctg gtgaagcctg gggcctcagt gaagatttcc    120
tgcaaggctt ctggctatgc attcactaac tcctggatga actgggtgaa gcagaggcct    180
ggaaagggtc ttgagtggat tggacggatt tatcctggag atggagaaac tatctacaat    240
gggaaattca gggtcaaggc cacactgact gcagacaaat cctccagcac agcctacatg    300
gatatcagca gcctgacatc tgaggactct gcggtctact tctgtgcaag aggctatgat    360
gattactcgt ttgcttactg gggccaaggg actctggtca ctgtctctgc aggtggtggt    420
ggttcgggtg gtggtggttc gggtggtggc ggatcggata ttgtgatgac tcaggctgca    480
ccctctatac ctgtcactcc tggagagtca gtatccatct cctgtaggtc tagtaagagt    540
ctcctgcata gtaatggcaa cacttacttg tattggttcc tgcagaggcc aggccagtct    600
cctcaactcc tgatatatcg gatgtccaac cttgcctcag gagtcccaga taggttcagt    660
ggcagtgggt caggaactgc tttcacactg agaatcagta gagtggaggc tgaggatgtg    720
ggtgtttatt actgtatgca acatatagaa tatccttta cgttcggatc ggggaccaag    780
ctggaaataa aaggaggtgg tggatcgggt ggtggtggtt cggaggcgg tggatcgcag    840 gttcagctgc agcagtctgg acctgagctg gtgaagcctg gggcctcagt gaagatttcc    900
tgcaaggctt ctggctatgc attcactaac tcctggatga actgggtgaa gcagaggcct    960
ggaaagggtc ttgagtggat tggacggatt tatcctggag atggagaaac tatctacaat   1020
gggaaattca gggtcaaggc cacactgact gcagacaaat cctccagcac agcctacatg   1080
gatatcagca gcctgacatc tgaggactct gcggtctact tctgtgcaag aggctatgat   1140
gattactcgt ttgcttactg gggccaaggg actctggtca ctgtctctgc aggtggtggt   1200
ggttcgggtg gtggtggttc gggtggtggc ggatcggata ttgtgatgac tcaggctgca   1260
ccctctatac ctgtcactcc tggagagtca gtatccatct cctgtaggtc tagtaagagt   1320
ctcctgcata gtaatggcaa cacttacttg tattggttcc tgcagaggcc aggccagtct   1380
cctcaactcc tgatatatcg gatgtccaac cttgcctcag gagtcccaga taggttcagt   1440
ggcagtgggt caggaactgc tttcacactg agaatcagta gagtggaggc tgaggatgtg   1500
ggtgtttatt actgtatgca acatatagaa tatccttta cgttcggatc ggggaccaag   1560
ctggaaataa aa                                                        1572

<210> SEQ ID NO 4
<211> LENGTH: 1572
```

<212> TYPE: DNA
<213> ORGANISM: Mus musculus

<400> SEQUENCE: 4

```
atggactgga cctggaggtt cctctttgtg gtggcagcag ctacaggtgt ccagtcccag     60
gtgcagctgg tgcagtctgg acctgaggtg aagaagcctg gggcctcagt gaaggtctcc    120
tgcaaggctt ctggatacac cttcaccaac tcctggatga actgggtgag gcagaggcct    180
ggaaagggtc ttgagtggat tggacggatt tatcctggag atggagaaac tatctacaat    240
gggaaattca gggtcagagt cacgattacc gcggacgaat ccacgagcac agcctacatg    300
caactgagca gcctgagatc tgaggacacg gccgtgtatt actgtgcgag aggctatgat    360
gattactcgt ttgcttactg gggccaggga accacggtca ccgtctcttc aggtggtggt    420
ggatccggag gtggtggatc gggtggtgga ggatcggata ttgtgatgac tcagtctcca    480
ctctccctgc ccgtcacccc tggagagccg gcctccatct cctgcaggtc tagtaagagt    540
ctcctgcata gtaatggcaa cacttacttg tattggttcc tgcagaagcc agggcagtct    600
ccacagctcc tgatctatcg gatgtccaac cttgcctcag ggtccctga caggttcagt     660
ggcagtggat caggcacaga ttttacactg aaaatcagca gagtggaggc tgaggatgtt    720
ggggtttatt actgcatgca acatatagaa tatccttta cgttcggcca agggaccaaa     780
ctggaaatca aggaggtgg tggatcgggt ggtggtggtt cggaggcgg tggatcgcag      840
gtgcagctgg tgcagtctgg acctgaggtg aagaagcctg gggcctcagt gaaggtctcc    900
tgcaaggctt ctggatacac cttcaccaac tcctggatga actgggtgag gcagaggcct    960
ggaaagggtc ttgagtggat tggacggatt tatcctggag atggagaaac tatctacaat   1020
gggaaattca gggtcagagt cacgattacc gcggacgaat ccacgagcac agcctacatg   1080
caactgagca gcctgagatc tgaggacacg gccgtgtatt actgtgcgag aggctatgat   1140
gattactcgt ttgcttactg gggccaggga accacggtca ccgtctcttc aggtggtggt   1200
ggatccggag gtggtggatc gggtggtgga ggatcggata ttgtgatgac tcagtctcca   1260
ctctccctgc ccgtcacccc tggagagccg gcctccatct cctgcaggtc tagtaagagt   1320
ctcctgcata gtaatggcaa cacttacttg tattggttcc tgcagaagcc agggcagtct   1380
ccacagctcc tgatctatcg gatgtccaac cttgcctcag ggtccctga caggttcagt    1440
ggcagtggat caggcacaga ttttacactg aaaatcagca gagtggaggc tgaggatgtt   1500
ggggtttatt actgcatgca acatatagaa tatccttta cgttcggcca agggaccaaa    1560
ctggaaatca aa                                                      1572
```

<210> SEQ ID NO 5
<211> LENGTH: 1572
<212> TYPE: DNA
<213> ORGANISM: Mus musculus

<400> SEQUENCE: 5

```
atggactgga cctggaggtt cctctttgtg gtggcagcag ctacaggtgt ccagtcccag     60
gtgcagctgg tgcagtctgg acctgaggtg aagaagcctg gggcctcagt gaaggtctcc    120
tgcaaggctt ctggatacac cttcaccaac tcctggatga actgggtgag ggagaggcct    180
ggaaagggtc ttgagtggat tggacggatt tatcctggag atggagaaac tatctacaat    240
gggaaattca gggtcagagt cacgattacc gcggacgaat ccacgagcac agcctacatg    300
caactgagca gcctgagatc tgaggacacg gccgtgtatt actgtgcgag aggctatgat    360
```

```
gattactcgt tgcttactg gggccaggga accacggtca ccgtctcttc aggtggtggt      420
ggatccggag gtggtggatc gggtggtgga ggatcggata ttgtgatgac tcagtctcca      480
ctctccctgc ccgtcacccc tggagagccg gcctccatct cctgcaggtc tagtaagagt      540
ctcctgcata gtaatggcaa cacttacttg tattggttcc tggagaagcc agggcagtct      600
ccacagctcc tgatctatcg gatgtccaac cttgcctcag gggtccctga caggttcagt      660
ggcagtggat caggcacaga ttttacactg aaaatcagca gagtggaggc tgaggatgtt      720
ggggtttatt actgcatgca acatatagaa tatccttta cgttcggcca agggaccaaa       780
ctggaaatca aggaggtgg tggatcgggt ggtggtggtt cggggaggcg gtggatcgcag       840 gtgcagctgg tgcagtctgg acctgaggtg aagaagcctg ggcctcagt gaaggtctcc        900 tgcaaggctt ctggatacac cttcaccaac tcctggatga actgggtgag gaagaggcct        960
ggaaagggtc ttgagtggat tggacggatt tatcctggag atggagaaac tatctacaat        1020
gggaaattca gggtcagagt cacgattacc gcggacgaat ccacgagcac agcctacatg        1080
caactgagca gcctgagatc tgaggacacg gccgtgtatt actgtgcgag aggctatgat        1140
gattactcgt ttgcttactg gggccaggga accacggtca ccgtctcttc aggtggtggt        1200
ggatccggag gtggtggatc gggtggtgga ggatcggata ttgtgatgac tcagtctcca        1260
ctctccctgc ccgtcacccc tggagagccg gcctccatct cctgcaggtc tagtaagagt        1320
ctcctgcata gtaatggcaa cacttacttg tattggttcc tgaagaagcc agggcagtct        1380
ccacagctcc tgatctatcg gatgtccaac cttgcctcag gggtccctga caggttcagt        1440
ggcagtggat caggcacaga ttttacactg aaaatcagca gagtggaggc tgaggatgtt        1500
ggggtttatt actgcatgca acatatagaa tatccttta cgttcggcca agggaccaaa        1560
ctggaaatca aa                                                          1572
```

<210> SEQ ID NO 6
<211> LENGTH: 524
<212> TYPE: PRT
<213> ORGANISM: Mus musculus

<400> SEQUENCE: 6

```
Met Asp Trp Thr Trp Arg Phe Leu Phe Val Val Ala Ala Ala Thr Gly
 1               5                  10                  15

Val Gln Ser Gln Val Gln Leu Val Gln Ser Gly Pro Glu Val Lys Lys
             20                  25                  30

Pro Gly Ala Ser Val Lys Val Ser Cys Lys Ala Ser Gly Tyr Thr Phe
         35                  40                  45

Thr Asn Ser Trp Met Asn Trp Val Arg Glu Arg Pro Gly Lys Gly Leu
     50                  55                  60

Glu Trp Ile Gly Arg Ile Tyr Pro Gly Asp Gly Glu Thr Ile Tyr Asn
 65                  70                  75                  80

Gly Lys Phe Arg Val Arg Val Thr Ile Thr Ala Asp Glu Ser Thr Ser
                 85                  90                  95

Thr Ala Tyr Met Gln Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
        115                 120                 125

Gln Gly Thr Thr Val Thr Val Ser Ser Gly Gly Gly Gly Ser Gly Gly
    130                 135                 140

Gly Gly Ser Gly Gly Gly Gly Ser Asp Ile Val Met Thr Gln Ser Pro
145                 150                 155                 160
```

Leu Ser Leu Pro Val Thr Pro Gly Glu Pro Ala Ser Ile Ser Cys Arg
            165                 170                 175

Ser Ser Lys Ser Leu Leu His Ser Asn Gly Asn Thr Tyr Leu Tyr Trp
        180                 185                 190

Phe Leu Glu Lys Pro Gly Gln Ser Pro Gln Leu Leu Ile Tyr Arg Met
            195                 200                 205

Ser Asn Leu Ala Ser Gly Val Pro Asp Arg Phe Ser Gly Ser Gly Ser
        210                 215                 220

Gly Thr Asp Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
            245                 250                 255

Gln Gly Thr Lys Leu Glu Ile Lys Gly Gly Gly Ser Gly Gly Gly
        260                 265                 270

Gly Ser Gly Gly Gly Ser Gln Val Gln Leu Val Gln Ser Gly Pro
        275                 280                 285

Glu Val Lys Lys Pro Gly Ala Ser Val Lys Val Ser Cys Lys Ala Ser
        290                 295                 300

Gly Tyr Thr Phe Thr Asn Ser Trp Met Asn Trp Val Arg Lys Arg Pro
305                 310                 315                 320

Gly Lys Gly Leu Glu Trp Ile Gly Arg Ile Tyr Pro Gly Asp Gly Glu
            325                 330                 335

Thr Ile Tyr Asn Gly Lys Phe Arg Val Arg Val Thr Ile Thr Ala Asp
            340                 345                 350

Glu Ser Thr Ser Thr Ala Tyr Met Gln Leu Ser Ser Leu Arg Ser Glu
        355                 360                 365

Asp Thr Ala Val Tyr Tyr Cys Ala Arg Gly Tyr Asp Asp Tyr Ser Phe
        370                 375                 380

Ala Tyr Trp Gly Gln Gly Thr Thr Val Thr Val Ser Ser Gly Gly Gly
385                 390                 395                 400

Gly Ser Gly Gly Gly Gly Ser Gly Gly Gly Gly Ser Asp Ile Val Met
            405                 410                 415

Thr Gln Ser Pro Leu Ser Leu Pro Val Thr Pro Gly Glu Pro Ala Ser
            420                 425                 430

Ile Ser Cys Arg Ser Ser Lys Ser Leu Leu His Ser Asn Gly Asn Thr
            435                 440                 445

Tyr Leu Tyr Trp Phe Leu Lys Lys Pro Gly Gln Ser Pro Gln Leu Leu
        450                 455                 460

Ile Tyr Arg Met Ser Asn Leu Ala Ser Gly Val Pro Asp Arg Phe Ser
465                 470                 475                 480

Gly Ser Gly Ser Gly Thr Asp Phe Thr Leu Lys Ile Ser Arg Val Glu
            485                 490                 495

Ala Glu Asp Val Gly Val Tyr Tyr Cys Met Gln His Ile Glu Tyr Pro
            500                 505                 510

Phe Thr Phe Gly Gln Gly Thr Lys Leu Glu Ile Lys
        515                 520

<210> SEQ ID NO 7
<211> LENGTH: 1572
<212> TYPE: DNA
<213> ORGANISM: Mus musculus

<400> SEQUENCE: 7
atggactgga cctggaggtt cctctttgtg gtggcagcag ctacaggtgt ccagtcccag      60

-continued

```
gtgcagctgg tgcagtctgg acctgaggtg aagaagcctg ggcctcagt gaaggtctcc      120 tgcaaggctt ctggatacac cttcaccaac tcctggatga actgggtgag ggagaggcct      180
ggaaagggtc ttgagtggat tggacggatt tatcctggag atggagaaac tatctacaat      240
gggaaattca gggtcagagt cacgattacc gcggacgaat ccacgagcac agcctacatg      300
caactgagca gcctgagatc tgaggacacg gccgtgtatt actgtgcgag aggctatgat      360
gattactcgt ttgcttactg gggccaggga accacggtca ccgtctcttc aggtggtggt      420
ggatccggag gtggtggatc gggtggtgga ggatcggata ttgtgatgac tcagtctcca      480
ctctccctgc ccgtcacccc tggagagccg gcctccatct cctgcaggtc tagtaagagt      540
ctcctgcata gtaatggcaa cacttacttg tattggttcc tgaagaagcc agggcagtct      600
ccacagctcc tgatctatcg gatgtccaac cttgcctcag ggtccctga caggttcagt       660 ggcagtggat caggcacaga ttttacactg aaaatcagca gagtggaggc tgaggatgtt      720
ggggtttatt actgcatgca acatatagaa tatccttta cgttcggcca agggaccaaa        780
ctggaaatca aggaggtgg tggatcgggt ggtggtggtt cgggaggcgg tggatcgcag        840
gtgcagctgg tgcagtctgg acctgaggtg aagaagcctg ggcctcagt gaaggtctcc        900 tgcaaggctt ctggatacac cttcaccaac tcctggatga actgggtgag gagaggcct        960 ggaaagggtc ttgagtggat tggacggatt tatcctggag atggagaaac tatctacaat       1020
gggaaattca gggtcagagt cacgattacc gcggacgaat ccacgagcac agcctacatg       1080
caactgagca gcctgagatc tgaggacacg gccgtgtatt actgtgcgag aggctatgat       1140
gattactcgt ttgcttactg gggccaggga accacggtca ccgtctcttc aggtggtggt       1200
ggatccggag gtggtggatc gggtggtgga ggatcggata ttgtgatgac tcagtctcca       1260
ctctccctgc ccgtcacccc tggagagccg gcctccatct cctgcaggtc tagtaagagt       1320
ctcctgcata gtaatggcaa cacttacttg tattggttcc tggagaagcc agggcagtct       1380
ccacagctcc tgatctatcg gatgtccaac cttgcctcag ggtccctga caggttcagt        1440 ggcagtggat caggcacaga ttttacactg aaaatcagca gagtggaggc tgaggatgtt       1500
ggggtttatt actgcatgca acatatagaa tatccttta cgttcggcca agggaccaaa        1560
ctggaaatca aa                                                           1572
```

<210> SEQ ID NO 8
<211> LENGTH: 524
<212> TYPE: PRT
<213> ORGANISM: Mus musculus

<400> SEQUENCE: 8

```
Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Glu Arg Pro Gly Lys Gly Leu
    50                  55                  60

Glu Trp Ile Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95
```

```
Thr Ala Tyr Met Gln Leu Ser Ser Leu Arg Ser Glu Asp Thr Ala Val
            100                 105                 110
Tyr Tyr Cys Ala Arg Gly Tyr Asp Asp Tyr Ser Phe Ala Tyr Trp Gly
        115                 120                 125
Gln Gly Thr Thr Val Thr Val Ser Ser Gly Gly Gly Gly Ser Gly Gly
    130                 135                 140
Gly Gly Ser Gly Gly Gly Gly Ser Asp Ile Val Met Thr Gln Ser Pro
145                 150                 155                 160
Leu Ser Leu Pro Val Thr Pro Gly Glu Pro Ala Ser Ile Ser Cys Arg
                165                 170                 175
Ser Ser Lys Ser Leu Leu His Ser Asn Gly Asn Thr Tyr Leu Tyr Trp
            180                 185                 190
Phe Leu Lys Lys Pro Gly Gln Ser Pro Gln Leu Leu Ile Tyr Arg Met
        195                 200                 205
Ser Asn Leu Ala Ser Gly Val Pro Asp Arg Phe Ser Gly Ser Gly Ser
    210                 215                 220
Gly Thr Asp Phe Thr Leu Lys Ile Ser Arg Val Glu Ala Glu Asp Val
225                 230                 235                 240
Gly Val Tyr Tyr Cys Met Gln His Ile Glu Tyr Pro Phe Thr Phe Gly
                245                 250                 255
Gln Gly Thr Lys Leu Glu Ile Lys Gly Gly Gly Gly Ser Gly Gly Gly
            260                 265                 270
Gly Ser Gly Gly Gly Gly Ser Gln Val Gln Leu Val Gln Ser Gly Pro
        275                 280                 285
Glu Val Lys Lys Pro Gly Ala Ser Val Lys Val Ser Cys Lys Ala Ser
    290                 295                 300
Gly Tyr Thr Phe Thr Asn Ser Trp Met Asn Trp Val Arg Lys Arg Pro
305                 310                 315                 320
Gly Lys Gly Leu Glu Trp Ile Gly Arg Ile Tyr Pro Gly Asp Gly Glu
                325                 330                 335
Thr Ile Tyr Asn Gly Lys Phe Arg Val Arg Val Thr Ile Thr Ala Asp
            340                 345                 350
Glu Ser Thr Ser Thr Ala Tyr Met Gln Leu Ser Ser Leu Arg Ser Glu
        355                 360                 365
Asp Thr Ala Val Tyr Tyr Cys Ala Arg Gly Tyr Asp Asp Tyr Ser Phe
    370                 375                 380
Ala Tyr Trp Gly Gln Gly Thr Thr Val Thr Val Ser Ser Gly Gly Gly
385                 390                 395                 400
Gly Ser Gly Gly Gly Gly Ser Gly Gly Gly Gly Ser Asp Ile Val Met
                405                 410                 415
Thr Gln Ser Pro Leu Ser Leu Pro Val Thr Pro Gly Glu Pro Ala Ser
            420                 425                 430
Ile Ser Cys Arg Ser Ser Lys Ser Leu Leu His Ser Asn Gly Asn Thr
        435                 440                 445
Tyr Leu Tyr Trp Phe Leu Glu Lys Pro Gly Gln Ser Pro Gln Leu Leu
    450                 455                 460
Ile Tyr Arg Met Ser Asn Leu Ala Ser Gly Val Pro Asp Arg Phe Ser
465                 470                 475                 480
Gly Ser Gly Ser Gly Thr Asp Phe Thr Leu Lys Ile Ser Arg Val Glu
                485                 490                 495
Ala Glu Asp Val Gly Val Tyr Tyr Cys Met Gln His Ile Glu Tyr Pro
            500                 505                 510
Phe Thr Phe Gly Gln Gly Thr Lys Leu Glu Ile Lys
```

```
              515                 520

<210> SEQ ID NO 9
<211> LENGTH: 4
<212> TYPE: PRT
<213> ORGANISM: Artificial
<220> FEATURE:
<223> OTHER INFORMATION: An artificially synthesized linker sequence

<400> SEQUENCE: 9

Gly Gly Gly Ser
1

<210> SEQ ID NO 10
<211> LENGTH: 4
<212> TYPE: PRT
<213> ORGANISM: Artificial
<220> FEATURE:
<223> OTHER INFORMATION: An artificially synthesized linker sequence

<400> SEQUENCE: 10

Ser Gly Gly Gly
1

<210> SEQ ID NO 11
<211> LENGTH: 5
<212> TYPE: PRT
<213> ORGANISM: Artificial
<220> FEATURE:
<223> OTHER INFORMATION: An artificially synthesized linker sequence

<400> SEQUENCE: 11

Gly Gly Gly Gly Ser
1               5

<210> SEQ ID NO 12
<211> LENGTH: 5
<212> TYPE: PRT
<213> ORGANISM: Artificial
<220> FEATURE:
<223> OTHER INFORMATION: An artificially synthesized linker sequence

<400> SEQUENCE: 12

Ser Gly Gly Gly Gly
1               5

<210> SEQ ID NO 13
<211> LENGTH: 6
<212> TYPE: PRT
<213> ORGANISM: Artificial
<220> FEATURE:
<223> OTHER INFORMATION: An artificially synthesized linker sequence

<400> SEQUENCE: 13

Gly Gly Gly Gly Gly Ser
1               5

<210> SEQ ID NO 14
<211> LENGTH: 6
<212> TYPE: PRT
<213> ORGANISM: Artificial
<220> FEATURE:
<223> OTHER INFORMATION: An artificially synthesized linker sequence

<400> SEQUENCE: 14

Ser Gly Gly Gly Gly Gly
1               5
```

<210> SEQ ID NO 15
<211> LENGTH: 7
<212> TYPE: PRT
<213> ORGANISM: Artificial
<220> FEATURE:
<223> OTHER INFORMATION: An artificially synthesized linker sequence

<400> SEQUENCE: 15

Gly Gly Gly Gly Gly Gly Ser
1               5

<210> SEQ ID NO 16
<211> LENGTH: 7
<212> TYPE: PRT
<213> ORGANISM: Artificial
<220> FEATURE:
<223> OTHER INFORMATION: An artificially synthesized linker sequence

<400> SEQUENCE: 16

Ser Gly Gly Gly Gly Gly Gly
1               5

<210> SEQ ID NO 17
<211> LENGTH: 5
<212> TYPE: PRT
<213> ORGANISM: Artificial
<220> FEATURE:
<223> OTHER INFORMATION: An artificially synthesized linker sequence

<400> SEQUENCE: 17

Gly Gly Pro Gly Ser
1               5

<210> SEQ ID NO 18
<211> LENGTH: 516
<212> TYPE: PRT
<213> ORGANISM: Artificial
<220> FEATURE:
<223> OTHER INFORMATION: An artificially synthesized scFv sequence

<400> SEQUENCE: 18

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Arg
            20                  25                  30

Pro Ser Gln Thr Leu Ser Leu Thr Cys Thr Val Ser Gly Tyr Ser Ile
        35                  40                  45

Thr Ser Asp His Ala Trp Ser Trp Val Arg Gln Pro Pro Gly Arg Gly
    50                  55                  60

Leu Glu Trp Ile Gly Tyr Ile Ser Tyr Ser Gly Ile Thr Thr Tyr Asn
65                  70                  75                  80

Pro Ser Leu Lys Ser Arg Val Thr Met Leu Arg Asp Thr Ser Lys Asn
                85                  90                  95

Gln Phe Ser Leu Arg Leu Ser Ser Val Thr Ala Ala Asp Thr Ala Val
            100                 105                 110

Tyr Tyr Cys Ala Arg Ser Leu Ala Arg Thr Thr Ala Met Asp Tyr Trp
        115                 120                 125

Gly Gln Gly Ser Leu Val Thr Val Ser Ser Gly Gly Gly Gly Ser Gly
    130                 135                 140

Gly Gly Gly Ser Gly Gly Gly Gly Ser Asp Ile Gln Met Thr Gln Ser
145                 150                 155                 160

-continued

```
Pro Ser Ser Leu Ser Ala Ser Val Gly Asp Arg Val Thr Ile Thr Cys
            165                 170                 175

Arg Ala Ser Gln Asp Ile Ser Ser Tyr Leu Asn Trp Tyr Gln Gln Lys
        180                 185                 190

Pro Gly Lys Ala Pro Lys Leu Leu Ile Tyr Tyr Thr Ser Arg Leu His
    195                 200                 205

Ser Gly Val Pro Ser Arg Phe Ser Gly Ser Gly Ser Gly Thr Asp Phe
210                 215                 220

Thr Phe Thr Ile Ser Ser Leu Gln Pro Glu Asp Ile Ala Thr Tyr Tyr
225                 230                 235                 240

Cys Gln Gln Gly Asn Thr Leu Pro Tyr Thr Phe Gly Gln Gly Thr Lys
            245                 250                 255

Val Glu Ile Lys Gly Gly Gly Gly Ser Gly Gly Gly Gly Ser Gly Gly
        260                 265                 270

Gly Gly Ser Gln Val Gln Leu Gln Glu Ser Gly Pro Gly Leu Val Arg
    275                 280                 285

Pro Ser Gln Thr Leu Ser Leu Thr Cys Thr Val Ser Gly Tyr Ser Ile
290                 295                 300

Thr Ser Asp His Ala Trp Ser Trp Val Arg Gln Pro Pro Gly Arg Gly
305                 310                 315                 320

Leu Glu Trp Ile Gly Tyr Ile Ser Tyr Ser Gly Ile Thr Thr Tyr Asn
            325                 330                 335

Pro Ser Leu Lys Ser Arg Val Thr Met Leu Arg Asp Thr Ser Lys Asn
        340                 345                 350

Gln Phe Ser Leu Arg Leu Ser Ser Val Thr Ala Ala Asp Thr Ala Val
    355                 360                 365

Tyr Tyr Cys Ala Arg Ser Leu Ala Arg Thr Thr Ala Met Asp Tyr Trp
370                 375                 380

Gly Gln Gly Ser Leu Val Thr Val Ser Gly Gly Gly Gly Ser Gly Gly
385                 390                 395                 400

Gly Gly Ser Gly Gly Gly Ser Asp Ile Gln Met Thr Gln Ser
            405                 410                 415

Pro Ser Ser Leu Ser Ala Ser Val Gly Asp Arg Val Thr Ile Thr Cys
        420                 425                 430

Arg Ala Ser Gln Asp Ile Ser Ser Tyr Leu Asn Trp Tyr Gln Gln Lys
    435                 440                 445

Pro Gly Lys Ala Pro Lys Leu Leu Ile Tyr Tyr Thr Ser Arg Leu His
450                 455                 460

Ser Gly Val Pro Ser Arg Phe Ser Gly Ser Gly Ser Gly Thr Asp Phe
465                 470                 475                 480

Thr Phe Thr Ile Ser Ser Leu Gln Pro Glu Asp Ile Ala Thr Tyr Tyr
            485                 490                 495

Cys Gln Gln Gly Asn Thr Leu Pro Tyr Thr Phe Gly Gln Gly Thr Lys
        500                 505                 510

Val Glu Ile Lys
    515
```

<210> SEQ ID NO 19
<211> LENGTH: 1548
<212> TYPE: DNA
<213> ORGANISM: Artificial
<220> FEATURE:
<223> OTHER INFORMATION: An artificially synthesized scFv sequence

<400> SEQUENCE: 19

-continued

```
atgggatgga gctgtatcat cctcttcttg gtagcaacag ctacaggtgt ccactcccag      60
gtccaactgc aggagagcgg tccaggtctt gtgagaccta gccagaccct gagcctgacc     120
tgcaccgtgt ctggctactc aattaccagc gatcatgcct ggagctgggt tcgccagcca     180
cctggacgag gtcttgagtg gattggatac attagttata gtggaatcac aacctataat     240
ccatctctca aatccagagt gacaatgctg agagacacca gcaagaacca gttcagcctg     300
agactcagca gcgtgacagc cgccgacacc gcggtttatt attgtgcaag atccctagct     360
cggactacgg ctatggacta ctggggtcaa ggcagcctcg tcacagtctc ctccggaggt     420
ggtggtagtg gaggtggtgg tagtggaggt ggtggtagtg acatccagat gacccagagc     480
ccaagcagcc tgagcgccag cgtgggcgac agagtgacca tcacctgtag agccagccag     540
gacatcagca gttacctgaa ttggtaccag cagaagccag gaaaggctcc aaagctgctg     600
atctactaca cctccagact gcactctggt gtgccaagca gattcagcgg tagcggtagc     660
ggtaccgact tcaccttcac catcagcagc ctccagccag aggacatcgc tacctactac     720
tgccaacagg gtaacacgct tccatacacg ttcggccaag gaccaaggt ggaaatcaaa     780 ggtggtggtg gttctggcgg cggcggctcc ggtggtggtg gatctcaggt ccaactgcag     840
gagagcggtc caggtcttgt gagacctagc cagaccctga gcctgacctg caccgtgtct     900
ggctactcaa ttaccagcga tcatgcctgg agctgggttc gccagccacc tggacgaggt     960
cttgagtgga ttggatacat tagttatagt ggaatcacaa cctataatcc atctctcaaa    1020
tccagagtga caatgctgag agacaccagc aagaaccagt tcagcctgag actcagcagc    1080
gtgacagccg ccgacaccgc ggtttattat tgtgcaagat ccctagctcg gactacggct    1140
atggactact ggggtcaagg cagcctcgtc acagtctcct caggaggagg aggatctgga    1200
ggaggaggat ctggaggagg aggatccgac atccagatga cccagagccc aagcagcctg    1260
agcgccagcg tgggcgacag agtgaccatc acctgtagag ccagccagga catcagcagt    1320
tacctgaatt ggtaccagca gaagccagga aaggctccaa agctgctgat ctactacacc    1380
tccagactgc actctggtgt gccaagcaga ttcagcggta gcggtagcgg taccgacttc    1440
accttcacca tcagcagcct ccagccagag gacatcgcta cctactactg ccaacagggt    1500
aacacgcttc catacacgtt cggccaaggg accaaggtgg aaatcaaa                 1548
```

<210> SEQ ID NO 20
<211> LENGTH: 8
<212> TYPE: PRT
<213> ORGANISM: Artificial
<220> FEATURE:
<223> OTHER INFORMATION: An artificially synthesized linker sequence

<400> SEQUENCE: 20

Gly Gly Gly Gly Ser Gly Gly Ser
1               5

<210> SEQ ID NO 21
<211> LENGTH: 12
<212> TYPE: PRT
<213> ORGANISM: Artificial
<220> FEATURE:
<223> OTHER INFORMATION: An artificially synthesized linker sequence

<400> SEQUENCE: 21

Gly Gly Gly Gly Ser Gly Gly Gly Gly Ser Gly Ser
1               5                   10